US012280376B2

(12) United States Patent
Chiu et al.

(10) Patent No.: US 12,280,376 B2
(45) Date of Patent: Apr. 22, 2025

(54) DEVICES AND SYSTEMS FOR DROPLET GENERATION AND METHODS FOR GENERATING DROPLETS

(71) Applicant: University of Washington, Seattle, WA (US)

(72) Inventors: Daniel Chiu, Seattle, WA (US); Li Wu, Seattle, WA (US); Yuling Qin, Seattle, WA (US)

(73) Assignee: University of Washington, Seattle, WA (US)

( * ) Notice: Subject to any disclaimer, the term of this patent is extended or adjusted under 35 U.S.C. 154(b) by 887 days.

(21) Appl. No.: 17/424,397

(22) PCT Filed: Feb. 4, 2020

(86) PCT No.: PCT/US2020/016521
§ 371 (c)(1),
(2) Date: Jul. 20, 2021

(87) PCT Pub. No.: WO2020/163283
PCT Pub. Date: Aug. 13, 2020

(65) Prior Publication Data
US 2022/0118454 A1   Apr. 21, 2022

Related U.S. Application Data

(60) Provisional application No. 62/802,579, filed on Feb. 7, 2019.

(51) Int. Cl.
*B01L 3/00* (2006.01)

(52) U.S. Cl.
CPC ... *B01L 3/502784* (2013.01); *B01L 3/502715* (2013.01); *B01L 2300/0645* (2013.01);
(Continued)

(58) Field of Classification Search
CPC ............ C12Q 1/6844; G01N 15/1404; G01N 15/1459; G01N 35/109; G01N 35/1009;
(Continued)

(56) References Cited

U.S. PATENT DOCUMENTS 3,380,584 A * 4/1968 Fulwyler ................. H03M 1/00
341/142
3,741,726 A * 6/1973 Mitchell ................ G01N 33/49
494/10
(Continued)

OTHER PUBLICATIONS

Yusof, A. et al., 2011 IEEE 24th International Conference on Micro Electro Mechanical Systems 2011, 1059-1062 (Year: 2011).*
(Continued)

*Primary Examiner* — Arlen Soderquist
(74) *Attorney, Agent, or Firm* — Christensen O'Connor Johnson Kindness PLLC

(57) ABSTRACT

Devices and systems for droplet generation and methods for generating droplets are described. In an embodiment, the devices and systems include a capillary configured to eject a droplet, such as in response to a voltage applied to an end of the capillary. In an embodiment, the devices and systems include a moveable stage configured to carry a multi-well plate and move the stage relative to the capillary such that the ejected droplet is selectively received by a well of the multi-well plate carried by the moveable stage.

86 Claims, 32 Drawing Sheets

(52) U.S. Cl.
CPC .................. *B01L 2300/0663* (2013.01); *B01L 2300/0829* (2013.01); *B01L 2300/0838* (2013.01)

(58) Field of Classification Search
CPC ......... B01L 3/502784; B01L 3/502715; B01L 3/0265
USPC ..................................................... 422/502
See application file for complete search history.

(56) References Cited

U.S. PATENT DOCUMENTS

| | | | | |
|---|---|---|---|---|
| 4,667,830 | A * | 5/1987 | Nozaki, Jr. | B07C 5/3427 209/579 |
| 5,785,926 | A * | 7/1998 | Seubert | B01L 3/02 73/864.22 |
| 5,958,342 | A * | 9/1999 | Gamble | B82Y 30/00 422/65 |
| 6,121,048 | A * | 9/2000 | Zaffaroni | B01J 19/0046 506/40 |
| 2002/0073787 | A1* | 6/2002 | Eigen | G01N 15/10 73/863 |
| 2002/0158196 | A1* | 10/2002 | Berggren | H01J 49/0454 250/288 |
| 2003/0150739 | A1 | 8/2003 | Morozov et al. | |
| 2003/0189167 | A1* | 10/2003 | Schultz | H01J 49/167 250/281 |
| 2004/0101445 | A1 | 5/2004 | Shvets et al. | |
| 2008/0017736 | A1* | 1/2008 | Lee | B41J 2/06 239/690.1 |
| 2008/0286751 | A1* | 11/2008 | Renaud | B01L 3/0268 435/5 |
| 2010/0285573 | A1* | 11/2010 | Leck | C12M 25/01 435/288.4 |
| 2012/0286176 | A1 | 11/2012 | Rajyaguru et al. | |
| 2013/0095469 | A1* | 4/2013 | Koltay | G01N 15/1404 435/286.4 |
| 2013/0236901 | A1 | 9/2013 | Potier et al. | |
| 2013/0308756 | A1 | 11/2013 | Bogan et al. | |
| 2016/0129443 | A1* | 5/2016 | Tovar | G01N 15/1484 506/40 |
| 2018/0133715 | A1* | 5/2018 | Craig | G01N 15/1484 |
| 2020/0376488 | A1* | 12/2020 | Wu | G01N 21/17 |

OTHER PUBLICATIONS

Gross, A. et al., Journal of Laboratory Automation 2013, 18, 504-518. (Year: 2013).*
Kasukurti, A. et al., Lab on a Chip 2014, 14, 4673-4679 with 2 pages of supplementary information. (Year: 2014).*
Schoendube, J. et al., Biomicrofluidics 2015, 9, paper 014117, 9 pages. (Year: 2015).*
Desta, I. T. et al., SLAS Technology 2017, 22, 431-436 with 4 pages of supporting information. (Year: 2017).*
Abate, A.R. and Weitz, D.A.., "Single-layer membrane valves for elastomeric microfluidic devices," Appl. Phys. Lett., 92:243509, 2008.
Abatemarco, J. et al., "RNA-aptamers-in-droplets (RAPID) high-throughput screening for secretory phenotypes," Nat. Commun., 8:332, DOI: 10.1038/s41467-017-00425-7, 2017.
Ahn, B. et al., "Concurrent droplet charging and sorting by electrostatic actuation," Biomicrofluidics, 3:044102, 2009.
Ahn, K. et al., "Dielectrophoretic manipulation of drops for high-speed microfluidic sorting devices," Appl. Phys. Lett., 88:024104, 2006.
Baroud, C.N. et al., "Thermocapillary valve for droplet production and sorting," Phys. Rev. E, 75:046302, 2007.
Basova, E.Y. and Foret, F.., "Droplet microfluidics in (bio)chemical analysis," Analyst, 140:22-38, 2015.
Bonner, W.A. et al., "Fluorescence Activated Cell Sorting," Rev. Sci. Instrum., 43(3):404-409, 1972.

Burrell, R.A. and Swanton, C., "Tumour heterogeneity and the evolution of polyclonal drug resistance," Mol. Oncol., 8(6):1095-1111, 2014.
Cao, Z. et al., "Droplet sorting based on the number of encapsulated particles using a solenoid valve," Lab Chip, 13:171-178, 2013.
Clark, I.C. and Abate, A.R., "Finding a helix in a haystack: nucleic acid cytometry with droplet microfluidics," Lab Chip, 17(12):2032-2045, 2017.
Cole, R.H. et al., "Printed droplet microfluidics for on demand dispensing of picoliter droplets and cells," Proc. Natl. Acad. Sci. USA, 114(33):8728-8733, 2017.
Gielen, F. et al., "Ultrahigh-throughput-directed enzyme evolution by absorbance-activated droplet sorting (AADS)," Proc. Natl. Acad. Sci. USA, 113(47):E7383-E7389, 2016.
Guo, M.T. et al., "Droplet microfluidics for high-throughput biological assays," Lab Chip, 12(12):2146-2155, 2012.
Heath, J.R. et al., "Single-cell analysis tools for drug discovery and development," Nat. Rev. Drug Discov., 15(3):204-216, 2016.
Kim, S.C. et al., "Single-Cell RT-PCR in Microfluidic Droplets with Integrated Chemical Lysis," Anal. Chem., 90(2):1273-1279, 2018.
Klein, A.M. et al., "Droplet barcoding for single-cell transcriptomics applied to embryonic stem cells," Cell, 161(5):1187-1201, 2015.
Lan, F., et al., "Single-cell genome sequencing at ultra-high-throughput with microfluidic droplet barcoding," Nat. Biotechnol., 35(7):640-646, 2017.
Lim, S.W. and Abate, A.R., "Ultrahigh-throughput sorting of microfluidic drops with flow cytometry," Lab Chip, 13:4563-4572, 2013.
Liu, D. et al., "Controlled Generation of Double Emulsions in Air," Anal. Chem., 85(13):6190-6194, 2013.
Loscertales, I.G. et al., "Micro/Nano Encapsulation via Electrified Coaxial Liquid Jets," Science, 295(5560):1695-1698, 2002.
Ma, Z. et al., "Fluorescence activated cell sorting via a focused traveling surface acoustic beam," Lab Chip, 17:3176-3185, 2017.
Marusyk, A. and Polyak, K.., "Tumor heterogeneity: causes and consequences," Biochim. Biophys. Acta, 1805 (1):105-117, 2010.
Novak, R. et al., "Single-Cell Multiplex Gene Detection and Sequencing with Microfluidically Generated Agarose Emulsions," Angew. Chem. Int. Ed., 50(2):390-395, 2011.
Pekin, D. et al., "Quantitative and sensitive detection of rare mutations using droplet-based microfluidics," Lab Chip, 11(13):2156-2166, 2011.
Qin, Y. et al., "A Fluorescence-Activated Single-Droplet Dispenser for High Accuracy Single-Droplet and Single-Cell Sorting and Dispensing," Anal. Chem., 91(10):6815-6819, 2019.
Romero, P.A. et al., "Dissecting enzyme function with microfluidic-based deep mutational scanning," Proc. Natl. Acad. Sci. USA, 112(23):7159-7164, 2015.
Shibue, T. and Weinberg, R.A., "EMT, CSCs, and drug resistance: the mechanistic link and clinical implications," Nat. Rev. Clin. Oncol., 14(10:611-629, 2017.
Shim, J.-u. et al., "Ultrarapid Generation of Femtoliter Microfluidic Droplets for Single-Molecule-Counting Immunoassays," ACS Nano, 7(7):5955-5964, 2013.
Swanton, C., "Intratumor Heterogeneity: Evolution through Space and Time," Cancer Research, 72(19):4875-4882, 2012.
Wang, D. and Bodovitz, S., "Single cell analysis: the new frontier in 'omics'," Trends Biotechnol., 28(6):281-290, 2010.
Xi, H.-D. et al., "Active droplet sorting in microfluidics: a review," Lab Chip, 17:751-771, 2017.
Zhang, K. et al., "On-chip manipulation of continuous picoliter-volume superparamagnetic droplets using a magnetic force," Lab Chip, 9:2992-2999, 2009.
Zhang, Q. et al., "Development of a facile droplet-based single-cell isolation platform for cultivation and genomic analysis in microorganisms," Sci. Rep., 7:41192, 2017.
Zhang, Y. et al., "Hydrodynamic dispensing and electrical manipulation of attolitre droplets," Nat. Commun., 7:12424, 2016.
Zhu, Y. et al., "Printing 2-Dimentional Droplet Array for Single-Cell Reverse Transcription Quantitative PCR Assay with a Microfluidic Robot," Sci. Rep., 5:9551, 2015.
Zhu, Z. et al., "Highly sensitive and quantitative detection of rare pathogens through agarose droplet microfluidic emulsion PCR at the single-cell level," Lab Chip, 12:3907-3913, 2012.

(56) References Cited

OTHER PUBLICATIONS

Zinchenko, A. et al., "One in a Million: Flow Cytometric Sorting of Single Cell-Lysate Assays in Monodisperse Picolitre Double Emulsion Droplets for Directed Evolution," Anal. Chem., 86(5):2526-2533, 2014.

* cited by examiner 0.9 kV 1.0 kV 1.1 kV 1.2 kV 1.25 kV 1.3 kV 1.35 kV 1.4 kV 1.45 kV

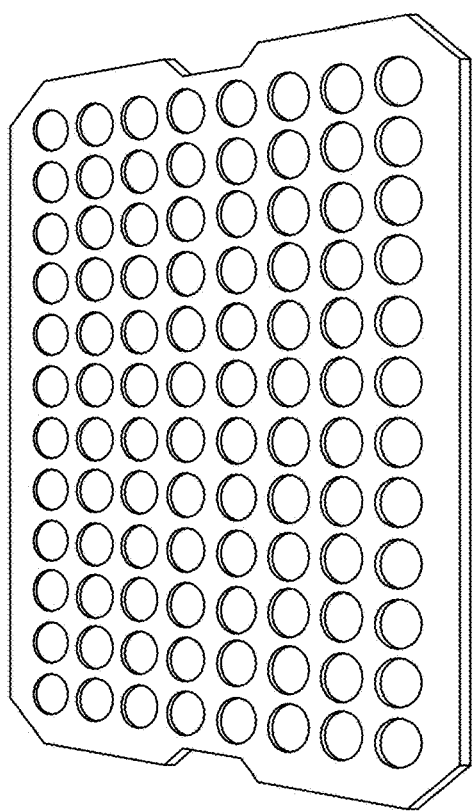
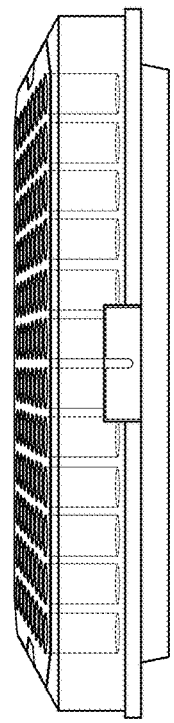
FIG. 9B
FIG. 9C
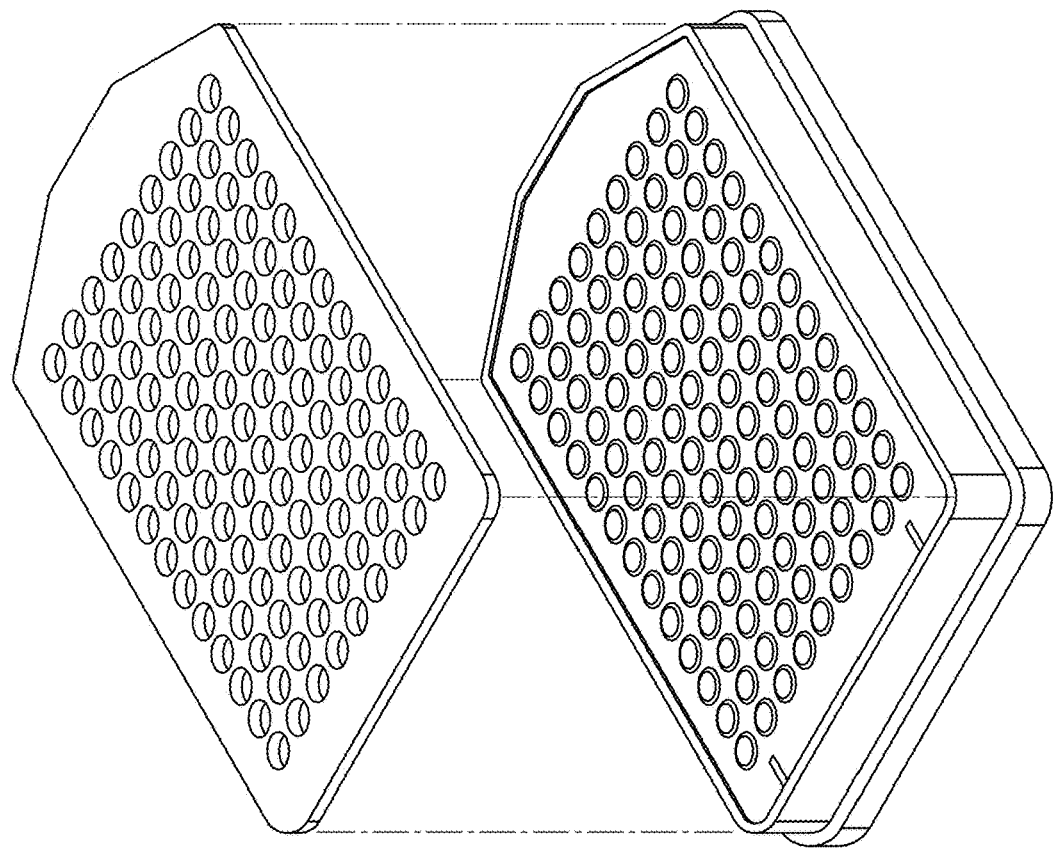
FIG. 9A

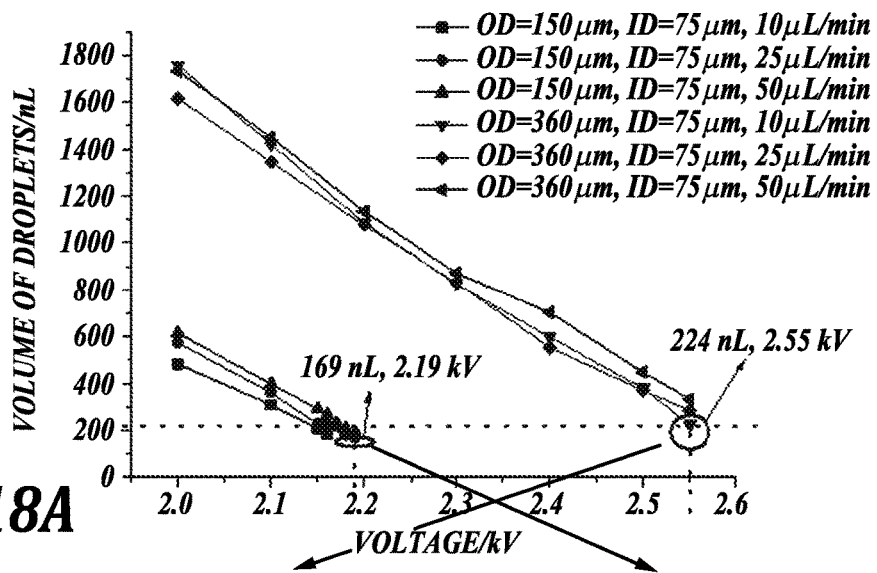
FIG. 18A
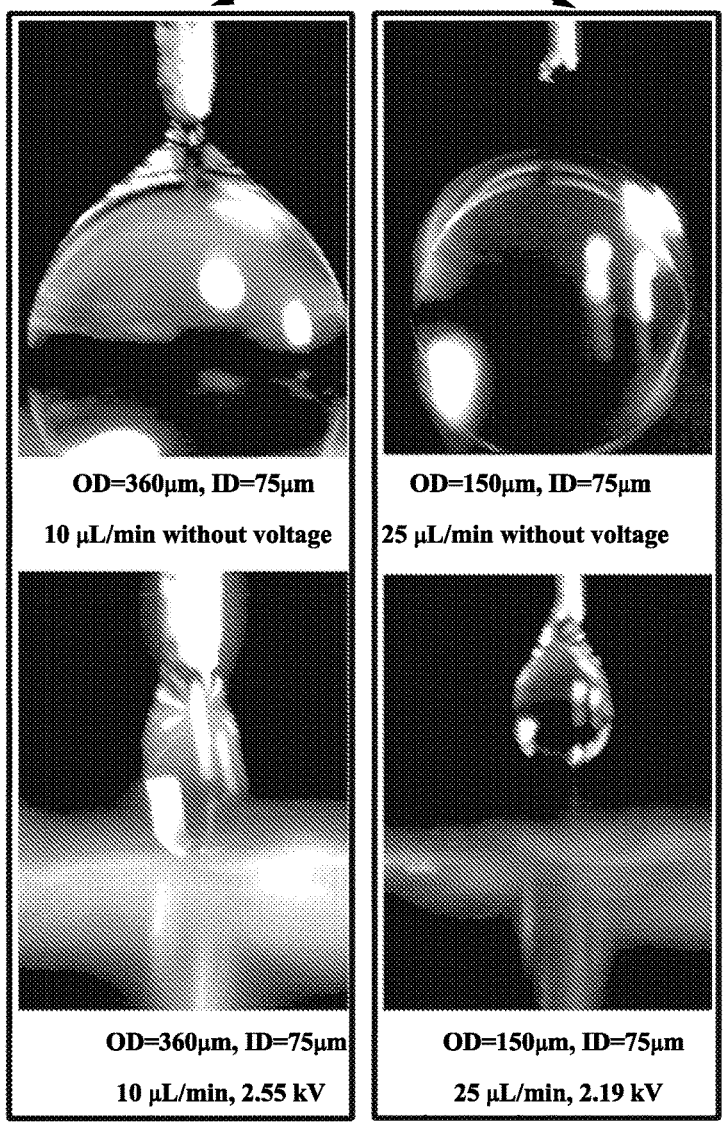
FIG. 18B  OD=360μm, ID=75μm  10 μL/min without voltage
FIG. 18C  OD=150μm, ID=75μm  25 μL/min without voltage
FIG. 18D  OD=360μm, ID=75μm  10 μL/min, 2.55 kV
FIG. 18E  OD=150μm, ID=75μm  25 μL/min, 2.19 kV

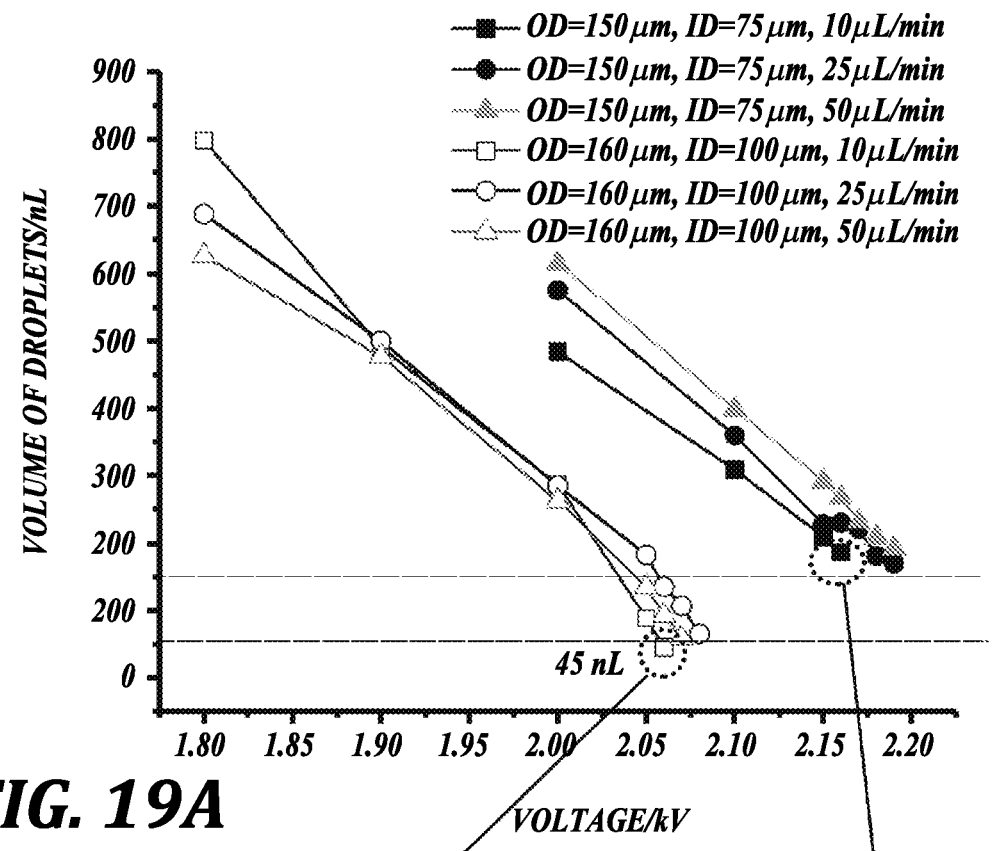
FIG. 19A
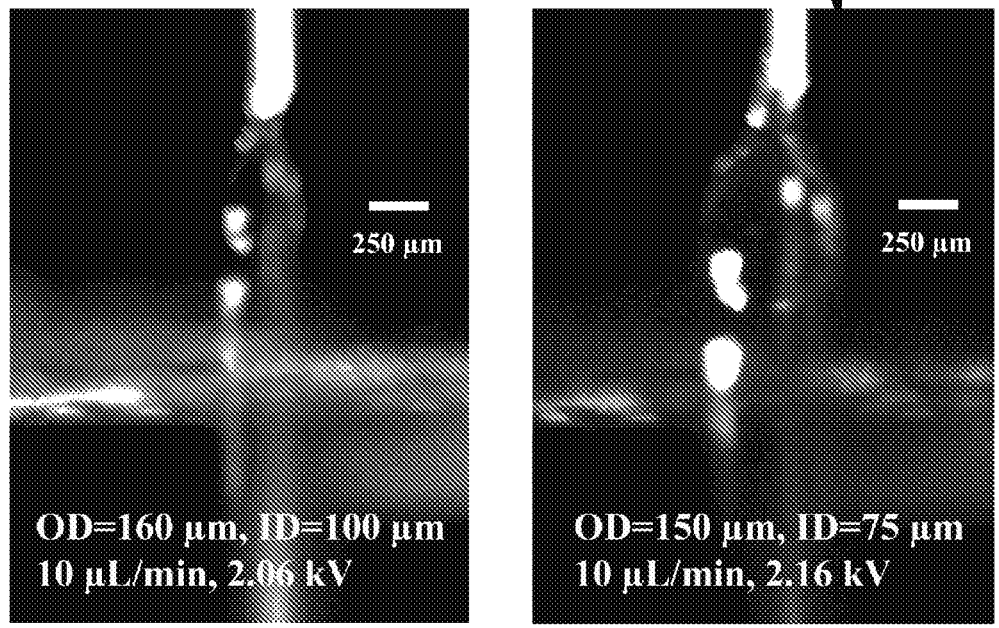
FIG. 19B　　　　　FIG. 19C

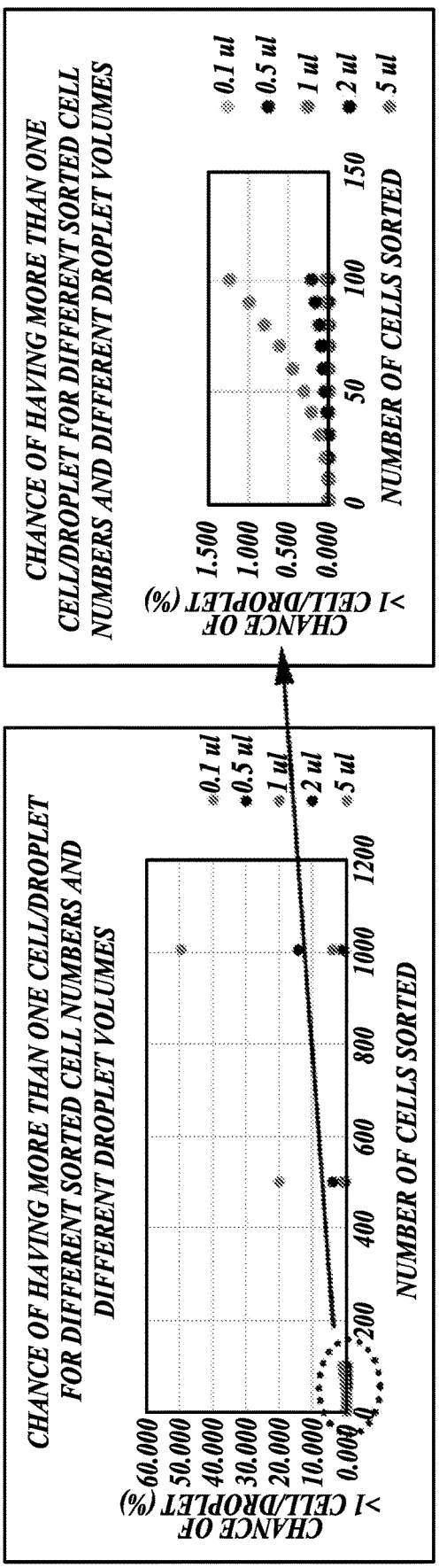
FIG. 20A
FIG. 20B
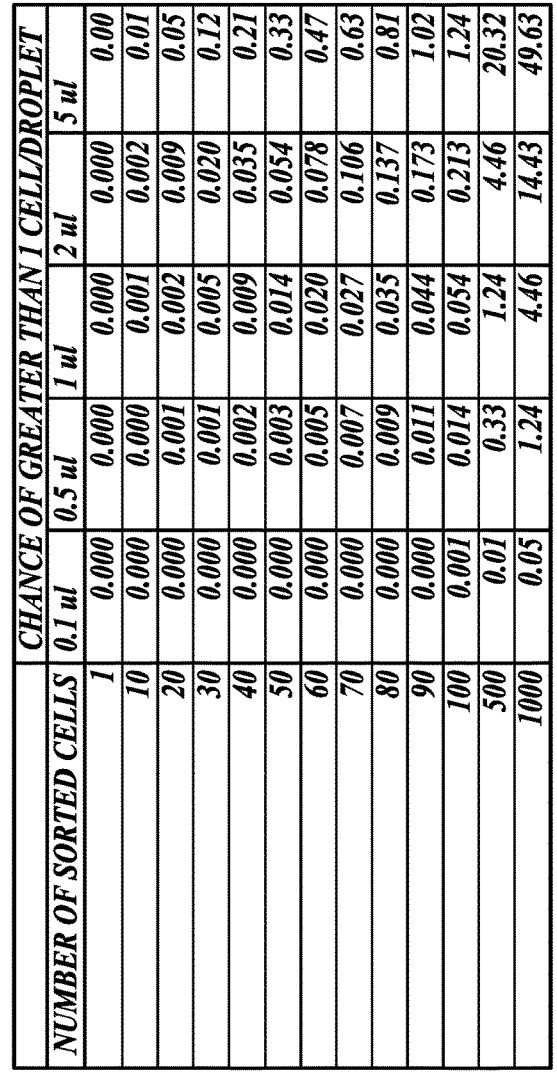
FIG. 20C
| NUMBER OF SORTED CELLS | CHANCE OF GREATER THAN 1 CELL/DROPLET | | | | |
|---|---|---|---|---|---|
| | 0.1 ul | 0.5 ul | 1 ul | 2 ul | 5 ul |
| 1 | 0.000 | 0.000 | 0.000 | 0.000 | 0.00 |
| 10 | 0.000 | 0.000 | 0.000 | 0.002 | 0.01 |
| 20 | 0.000 | 0.001 | 0.001 | 0.009 | 0.05 |
| 30 | 0.000 | 0.001 | 0.002 | 0.020 | 0.12 |
| 40 | 0.000 | 0.002 | 0.003 | 0.035 | 0.21 |
| 50 | 0.000 | 0.003 | 0.005 | 0.054 | 0.33 |
| 60 | 0.000 | 0.005 | 0.007 | 0.078 | 0.47 |
| 70 | 0.000 | 0.007 | 0.009 | 0.106 | 0.63 |
| 80 | 0.000 | 0.009 | 0.011 | 0.137 | 0.81 |
| 90 | 0.000 | 0.011 | 0.014 | 0.173 | 1.02 |
| 100 | 0.001 | 0.014 | 0.044 | 0.213 | 1.24 |
| 500 | 0.01 | 0.33 | 1.24 | 4.46 | 20.32 |
| 1000 | 0.05 | 1.24 | 4.46 | 14.43 | 49.63 |

DEVICES AND SYSTEMS FOR DROPLET GENERATION AND METHODS FOR GENERATING DROPLETS

CROSS-REFERENCES TO RELATED APPLICATIONS

This application is a U.S. National Stage of co-pending International Patent Application No. PCT/US2020/016521, filed Feb. 4, 2020, which claims the benefit of U.S. Provisional Patent Application No. 62/802,579, filed Feb. 7, 2020; the contents of each of which is hereby incorporated by reference in its entirety.

BACKGROUND

Rare subtypes within a cell population can be biologically and medically important but are often overlooked due to measurement of average cell properties. For example, intratumor cell heterogeneity plays a key role in chemo-resistance and tumor recurrence. Tumor cell subpopulations can exhibit different cell behaviors in response to drug treatment, presenting an obstacle to effective cancer therapy. To better understand tumor cell heterogeneity, measurements at the level of individual cells are important. Early developments in single-cell analysis began primarily with fluorescence-activated cell sorting (FACS), in which fluorescently-labeled cells in a fluid stream are screened and sorted for downstream applications. Although conventional FACS is an automated single-cell sorting and analysis system with high throughput and accuracy, it typically relies on antibody staining of protein biomarkers, and its inability to isolate single cells based on genetic makeup limits its flexibility. For example, isolation and recovery of an individual cell based on its nucleic-acid-sequence content, such as the cell's genotype, is difficult to achieve using existing flow cytometry techniques. In addition, conventional FACS often requires samples containing >$10^5$ cells, which limits applications in which the input cell number is low, such as in the study of rare cells.

SUMMARY

Toward that end, the present disclosure provides droplet-based devices, systems, and methods to overcome the above limitations. In an embodiment, the devices, systems, and methods of the present disclosure are suitable to encapsulate single cells in confined nanoliter-to-picoliter volume droplets. As discussed further herein, in an embodiment, such droplets include aqueous droplets within an oil emulsion, creating microreactors in which independent single-cell reactions can be performed. Droplets of interest may be sorted based on, for example, a fluorescence signal generated by a reaction, such as polymerase chain reaction (PCR), and are collected for further analysis. This technology is a valuable alternative to flow cytometry techniques that typically sort cells based on protein biomarkers, expanding the basis of cell sorting, for example, to nucleic-acid sequences and secreted biomolecules.

Additionally, wider application of droplet microfluidics-based single-cell analysis would be further facilitated by a droplet-sorting and dispensing method that is compatible with well plates and which is simple and economical to implement. Conventional fluorescence-activated cell sorting (FACS) instruments are incompatible with oil emulsions, and require re-dispensing water-in-oil emulsion droplets into water carriers to form double emulsion droplets. However, these double emulsions are highly polydisperse, limiting quantitative analysis and the types of assays that are possible.

Toward this end, the present disclosure provides, in an aspect, an automated droplet dispenser suitable to collect single droplets and single cells into well plates. In an embodiment, the device includes an automated fluorescence-activated single-droplet dispenser configured to sort and dispense single droplets or single cells with high accuracy. As described further herein, such a microfluidic fluorescence-activated single-droplet dispenser (FASD) is suitable to isolate individual droplets within an oil emulsion based on, for example, a fluorescence signal and dispense the droplets with nanoliter precision into multi-well plates for downstream analysis.

As discussed and demonstrated further herein, the devices, systems, and methods of the present disclosure provide a general approach for analyzing and dispensing microfluidic droplets carried in, for example, water or oil phases and allow analysis of samples containing small numbers of cells. Such devices, systems, and methods are suitable to achieve high-resolution cytometric detection and dispense single droplets with high efficiency and accuracy. Dispensing uniform droplets into multi-well plates allows accurate quantitative single-cell analysis.

Further, the devices and systems of the present disclosure are configured to be integrated with existing microfluidic devices to allow for sophisticated pretreatment and single-cell analysis. In an embodiment, all liquid handling operations are automated, and, in this regard, the systems and devices of the present disclosure are configured to be embedded into and/or coupled with conventionally available large-scale screening systems. Compared to previously described single droplet manipulation devices and methods, the devices, systems, and methods of the present disclosure are more automated and provide more accurate droplet dispensing, such as into multi-well plates. The devices, systems, and methods of the present disclosure are suitable to facilitate droplet microfluidics-based single-cell analysis applications, expanding the basis of cell sorting to include nucleic-acid sequences and cell secretions.

Accordingly, in aspect, the present disclosure provides a device for producing a droplet. In an embodiment, the device generally includes device for producing a droplet, the device comprising: a capillary defining a lumen, the capillary comprising: a first end coupleable to a fluid source; and a second end opposite the first end; an electrode in conductive communication with the second end of the capillary and a power source; a light source positioned to illuminate the lumen of the capillary; a photodetector positioned to absorb light from within the lumen and configured to generate an electrical signal in response to the light from within the lumen; and a controller operatively coupled to the power source and the photodetector, the controller including logic that when executed by the controller, causes the device to perform operations including: detecting the light from within the lumen based on the electrical signal from the photodetector; and applying, with the power source, a voltage to the electrode sufficient to eject a droplet from the second end of the capillary. In an embodiment, the device generally includes device for producing a droplet, the device comprising: a capillary defining a lumen, the capillary comprising: a first end coupleable to a fluid source; and a second end opposite the first end, wherein a viewing portion of the lumen of the capillary is configured for visual inspection by a user; an electrode in conductive communication with the second end of the capillary and a power source; a light source positioned to illuminate the lumen of the capillary; and a controller operatively coupled to the power source, the controller including logic that when executed by the controller, causes the device to perform operations including: applying, with the power source, a voltage to the electrode sufficient to eject a droplet from the second end of the capillary.

In another aspect, the present disclosure provides a system for generating droplets. In an embodiment, the system generally includes a fluid source; and a device comprising: a capillary defining a lumen in fluidic communication with the fluid source, the capillary comprising: a first end coupled to the fluid source; and a second end opposite the first end; an electrode in conductive communication with the second end of the capillary and a power source; a light source positioned to illuminate the lumen of the capillary; a photodetector configured to generate an optical signal in response to light emitted by the light source; and a controller operatively coupled to the power source, the photodetector, and the light source, the controller including logic that when executed by the controller, causes the device to perform operations including: detecting the light from within the lumen based on the electrical signal from the photodetector; and applying, with the power source, a voltage to the electrode sufficient to eject a droplet from the second end of the capillary.

In yet another aspect, the present disclosure provides a method for producing a droplet. In an embodiment, the method generally includes flowing a fluid through a capillary; into a lumen of the capillary; generating, with a photodetector, and applying, with a power source, a voltage to an electrode conductively coupled to a distal end of the capillary to eject a droplet from the distal end.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 9A is a schematic illustration of a 96-well plate and a multi-well plate cover, in accordance with an embodiment of the disclosure;

FIG. 9B is an image of a 96-well plate covered with a multi-well plate cover, shown here as a grounded-metallic board, to shield the electrostatic interaction between the multi-well plate and droplets ejected from a capillary, in accordance with an embodiment of the disclosure;

FIG. 9C is a side view of the multi-well plate cover of FIG. 9B;

FIG. 10C is the zoomed in soundtrack of a step in X-orientation, which takes 0.16 s, and where FIG. 10D is the enlarged soundtrack of a step in Y-orientation, which takes 0.3 s;

FIG. 18A is a graphic illustration of droplet volume as a function of voltage applied to a capillary of a device, in accordance with an embodiment of the disclosure, with varying capillary outer diameter;

FIGS. 18B-18E are a series of images of droplets generated with the capillaries described in FIG. 18A;

FIG. 19A is a graphic illustration of droplet volume as a function of applied voltage to a capillary of a device, in accordance with an embodiment of the disclosure, with varying capillary inner diameter;

FIGS. 19B and 19C are images of droplets generated with capillaries described in FIG. 19A;

FIG. 20A is a graphic illustration of a chance of a droplet ejected by a device, in accordance with an embodiment of the disclosure, containing more than one cell for different numbers of sorted cells and different droplet volumes;

FIG. 20B is a graphic illustration of the inset of FIG. 20A;

FIG. 20C a tabular representation of the data illustrated in FIGS. 20A and 20B; FIG. 21C is given to show the staining results of dead cells, using as a negative control for FIGS. 21A and 21B.

DETAILED DESCRIPTION

Figure 1A:
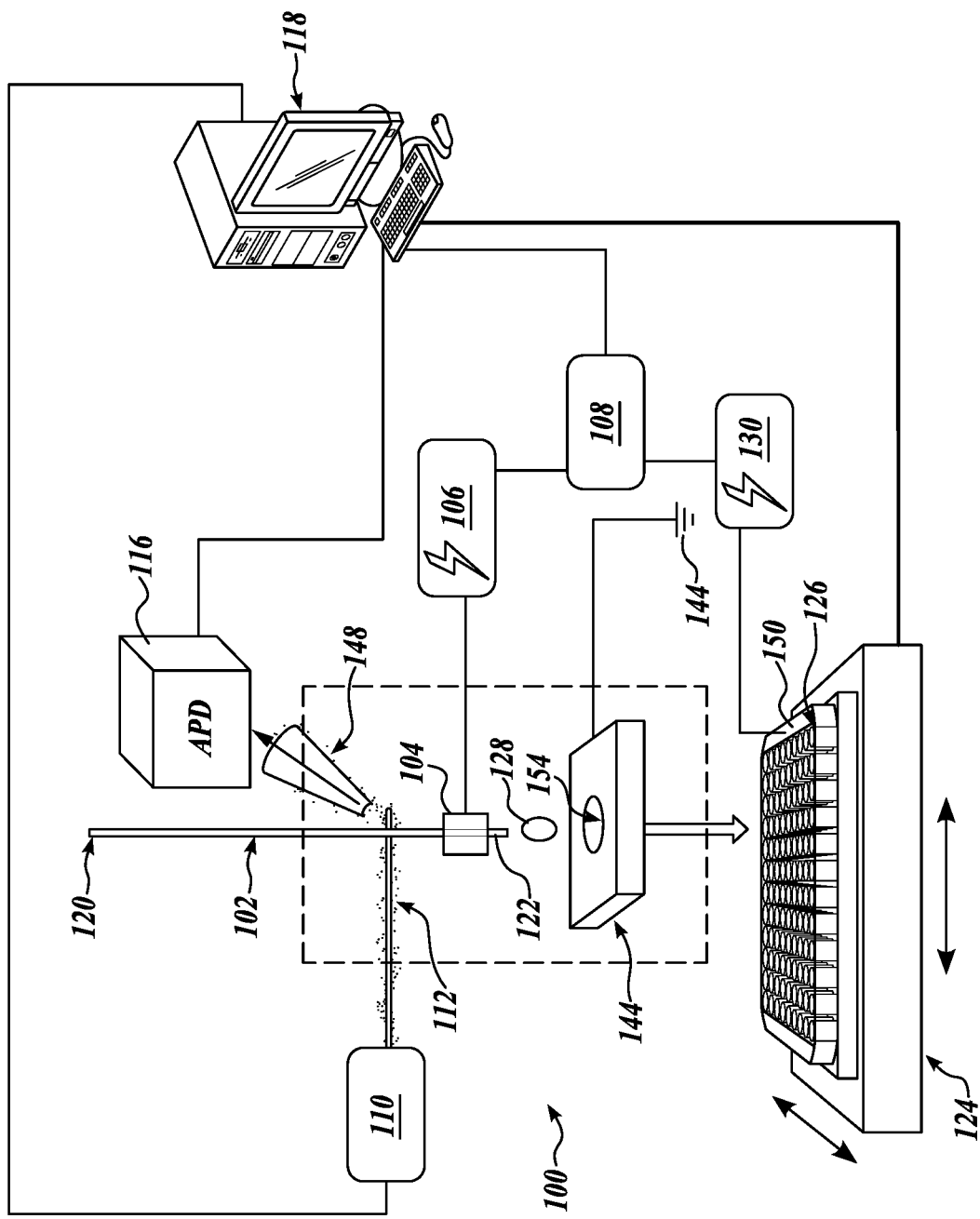
FIG. 1A is a schematic illustration of a device for producing a droplet, in accordance with an embodiment of the disclosure.

The present disclosure is generally directed to devices, systems, and methods for dispensing droplets. As discussed further herein, the devices, systems, and methods of the present disclosure eject droplets from a capillary, such as through electrohydrodynamic actuation of the capillary and fluid disposed in the capillary. Further, in certain embodiments, such devices, systems, and methods dispense such droplets in a manner suitable to sort the ejected droplets based on content of portions of the fluid disposed in the capillary, which form the droplets. Such sorting capabilities may be advantageously used to sort portions of the fluid based on the presence or absence of analytes, such as cells, cell fragments, and/or amplified nucleic acid, in the droplets. Devices In an aspect, the present disclosure provides a device for producing a droplet. As described further herein, such a device is configured to controllably produce droplets and may be coupled to a fluid source. Further, in an embodiment, the device is configured to sort droplets, such as based upon contents of the droplets.

In an embodiment, the device comprises a capillary and an electrode in conductive communication with a portion of the capillary and a power source. In this regard, the device is configured to produce a droplet, such as when a voltage is applied to the capillary. As used herein, the term "in conductive communication with" means that the subject electrical components are configured and positioned to be in electrically conductive contact with one another. The terms "electrical communication" and "conductive communication" are used interchangeably herein.

Any of the power sources disclosed herein can be a commercially available power source, or a custom fabricated power source. In some aspects, any of the power sources disclosed herein can provide direct current. In some aspects, any of the power sources disclosed herein can provide alternating current. Other types of power source can be used for any of the power sources disclosed herein, and can be determined by one of ordinary skill in the art according the specific requirements of his or her application.

In an embodiment, the electrode includes an electrically conductive material. In an embodiment, the electrically conductive material is selected from the group consisting of silver, gold, platinum, steel, iron, copper and combinations thereof.

In an embodiment, the capillary defines a lumen configured to allow passage of a fluid therethrough, such as a fluid from a fluid source coupled to the device. In an embodiment, the capillary includes a first end coupleable to a fluid source; and a second end opposite the first end.

As discussed further herein with respect to the systems of the present disclosure, the fluid source can include an aqueous fluid source. In this regard, the device may be configured to generate, for example, an aqueous droplet in air. In an embodiment, the fluid source coupleable to the device includes a droplet source. In this regard, the device may be configured to generate a double emulsion, such as an aqueous core at least partially surrounded by an immiscible oil. In some aspects, the device may comprise a junction, such as a T-junction. In some aspects, the geometry of the fluid source and junctions therein may be configured to achieve droplet emulsions by means of flow-focusing. In some aspects, the device is configured to generate droplet emulsions wherein a droplet of a first liquid is completely surrounded by a second, immiscible liquid.

As used herein, the terms "multi-phase emulsion" and "double emulsion" are used interchangeably, and include any combination of three or more fluids wherein each of the three or more fluids is immiscible with, but in physical contact with, at least one of the other fluids. As used herein, the term "fluid" means any liquid phase matter or gas phase matter. As used herein, the term "immiscible fluids" or "immiscible liquids" means two or more fluids that, under a given set of experimental conditions, do not undergo mixing or blending to an appreciable degree to form a homogeneous mixture, even when in physical contact with one another. In various embodiments, a double emulsion of droplets can be produced between three or more immiscible fluids. In some aspects, the double emulsion comprises an inner droplet comprising a first liquid, the inner droplet encapsulated in an outer droplet comprising a second liquid, the outer droplet encapsulated in a gas. As discussed further herein, such double emulsions may be suitable for analyzing lysed cells, such as by PCR, where the double emulsion is configured to contain the contents of the lysed cell and any amplified nucleic acid disposed in the double emulsion. In various embodiments, a single emulsion comprises a droplet comprising, for example, a first liquid encapsulated by a fluid, such as air or another gas. As discussed further herein, such a single emulsion may be suitable to analyze an isolated or selected intact cell (e.g. live or fixed but not lyzed) of interest disposed in the single emulsion, such as a rare cell selected from a larger population of cells.

In an embodiment, the capillary comprises a material selected from the group consisting of polydimethylsiloxane, polymethylmethacrylate, polyethylene, polyester, polytetrafluoroethylene, polycarbonate, polyvinyl chloride, fluoroethylpropylene, lexan, polystyrene, cyclic olefin copolymers, polyurethane, polyurethane methacrylate, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymers, polyvinylidene fluoride, polyamide, polyimide and combinations thereof. In an embodiment, the capillary comprises a material selected from the group consisting of inorganic materials (glass, quartz, silicon, GaAs, silicon nitride), fused silica, ceramic, glass (organic), metals and/or other materials and combinations thereof. In an embodiment, the capillary comprises a fused silica capillary. In an embodiment, the capillary is chemically modified, such as with a surface modification, such as to enhance wetting. Surface-modification chemicals may include, without limitation, silanes such as trimethylchlorosilane, hexamethyldisilazane, (Tridecafluoro-1,1,2,2-tetrahydrooctyl)trichlorosilane, chlorodimethyloctylsilane, octadecyltrichlorosilane or γ-methacryloxypropyltrimethyoxy-silane; polymers such as acrylic acid, acrylamide, dimethylacrylamide, 2-hydroxyethyl acrylate, polyvinylalcohol, poly(vinylpyrrolidone), poly(ethylene imine), polyethylene glycol, epoxy poly(dimethylacrylamide), or PEG-monomethoxyl acrylate; surfactants such as Pluronic® surfactants, poly(ethylene glycol)-based surfactants, sodium dodecylsulfate dodecyltrimethylammonium chloride, cetyltriethylammonium bromide, or Polybrene; cellulose derivatives such as hydroxypropylcellulose, or hydroxypropylmethylcellulose; amines such as ethylamine, diethylamine, triethylamine, or triethanolamine, fluorine-containing compounds such as those containing polytetrafluoroethylene or Teflon®.

In an embodiment, the second end of the capillary is in conductive communication with the electrode and with a power source. In that regard, as a voltage is applied to the electrode a droplet is ejected from the second end of the capillary, such as through electrohydrodynamic actuation of the capillary.

In an embodiment, the electrode is a positive electrode configured to draw negative charges in a fluid disposed in the capillary back toward the electrode, polarizing the fluid in the lumen of the capillary. As discussed further herein, in an embodiment, the capillary contains liquid droplets or discrete partitions that are surrounded at least in part by a second, immiscible liquid, and when the electric field is high enough, net positive charges in one or both of the liquids cause a double emulsion droplet to form at the second end of the capillary, until the double emulsion droplet is ejected from the second end of the capillary.

In an embodiment, the electrode is a negative electrode configured to draw positive charges in a fluid disposed in the capillary back toward the electrode, polarizing the fluid in the lumen of the capillary. As discussed further herein, in an embodiment, the capillary contains liquid droplets encapsulated in a second, immiscible liquid, and when the electric field is high enough, net negative charges in one or both of the liquids cause a double emulsion droplet to form at an emitter tip at the distal end of the channel, until the double emulsion droplet is ejected from the second end of the capillary.

In an embodiment, an electrical force generated by the power source is sufficient to enable precise control over various parameters of, for example, double emulsion droplets generated, including without limitation, the diameter of an inner droplet of the emulsion, the diameter of an outer droplet of the emulsion, the volume of an inner droplet of the emulsion, the number of inner droplets in each outer droplet of the emulsion, and the frequency or rate at which droplets are emitted from the emitter.

In certain embodiments, the electrical force generated by the voltage source is sufficient to generate a double emulsion droplet, wherein the diameter of the inner droplet is between 5 microns and 15 microns, between 10 microns and 30 microns, between 20 microns and 40 microns, between 30 microns and 50 microns, between 40 microns and 60 microns, between 50 microns and 70 microns, between 60 microns and 80 microns, between 70 microns and 90 microns, between 80 microns and 100 microns, between 90 microns and 110 microns, between 100 microns and 300 microns, between 200 microns and 400 microns, between 300 microns and 500 microns, between 400 microns and 600 microns, between 500 microns and 700 microns, between 600 microns and 800 microns, between 700 microns and 900 microns, or between 800 microns and 1000 microns.

In certain embodiments, the electrical force generated by the voltage source is sufficient to generate a double emulsion droplet, wherein the diameter of the outer droplet is between 5 microns and 15 microns, between 10 microns and 30 microns, between 20 microns and 40 microns, between 30 microns and 50 microns, between 40 microns and 60 microns, between 50 microns and 70 microns, between 60 microns and 80 microns, between 70 microns and 90 microns, between 80 microns and 100 microns, between 90 microns and 110 microns, between 100 microns and 300 microns, between 200 microns and 400 microns, between 300 microns and 500 microns, between 400 microns and 600 microns, between 500 microns and 700 microns, between 600 microns and 800 microns, between 700 microns and 900 microns, or between 800 microns and 1000 microns.

In an embodiment, an electrical force generated by the power source is sufficient to enable precise control over various parameters of single emulsion droplets generated, including without limitation, the diameter of the liquid droplet, the volume of the liquid droplet, and the frequency or rate at which droplets are emitted from the emitter.

In certain embodiments, the electrical force generated by the voltage source is sufficient to generate a single emulsion droplet, wherein the diameter of the liquid droplet is between 5 microns and 15 microns, between 10 microns and 30 microns, between 20 microns and 40 microns, between 30 microns and 50 microns, between 40 microns and 60 microns, between 50 microns and 70 microns, between 60 microns and 80 microns, between 70 microns and 90 microns, between 80 microns and 100 microns, between 90 microns and 110 microns, between 100 microns and 300 microns, between 200 microns and 400 microns, between 300 microns and 500 microns, between 400 microns and 600 microns, between 500 microns and 700 microns, between 600 microns and 800 microns, between 700 microns and 900 microns, or between 800 microns and 1000 microns.

In an embodiment, the devices of the present disclosure are configured to operate certain functions based upon one or more user inputs. In that regard, at least a portion of the capillary may be configured for visual inspection and/or interrogation by a user. In an embodiment, a viewing portion of the lumen of the capillary is configured for visual inspection and/or interrogation by a user. In an embodiment, the viewing portion is defined at least in part by a window of a capillary holder, as discussed further herein with respect to FIG. 1C. In an embodiment, the viewing portion is defined at least in part by an optically transmissive electrode, such as an electrode including a transparent conductive film, as discussed further herein.

In an embodiment, the device further includes a microscope or other magnifying optical component positioned to magnify the viewing portion of the lumen to generate a magnified image for receipt by the user. In this regard, a user may view contents of the lumen. In an embodiment, the device is configured to apply the voltage to the electrode, thus, for example, ejecting a droplet from the capillary, in response to an input from a user. Accordingly, in operation, a user may visually inspect and/or interrogate the lumen of the capillary and, depending upon the contents of the lumen, provide an input to the device, such as by depressing a button or other component, thereby generating a user input and ejecting a droplet from the capillary including the interrogated contents.

In an embodiment, the device is configured to manually sort droplets ejected by the device, such as in response to a user input. As discussed further herein, in an embodiment, the devices of the present disclosure include a moveable stage configured to carry a multi-well plate. In an embodiment, the moveable stage is configured to move relative to a second end of the capillary based on a user input such that a droplet ejected from the capillary is selectively received by one of the wells of the multi-well plate. In this regard, a user can direct a droplet ejected from the device to a selected well of the multi-well plate, such as when a cell or other analyte is detected in the lumen of the capillary and where the cell or other analyte is directed to the selected well.

Figure 1B:
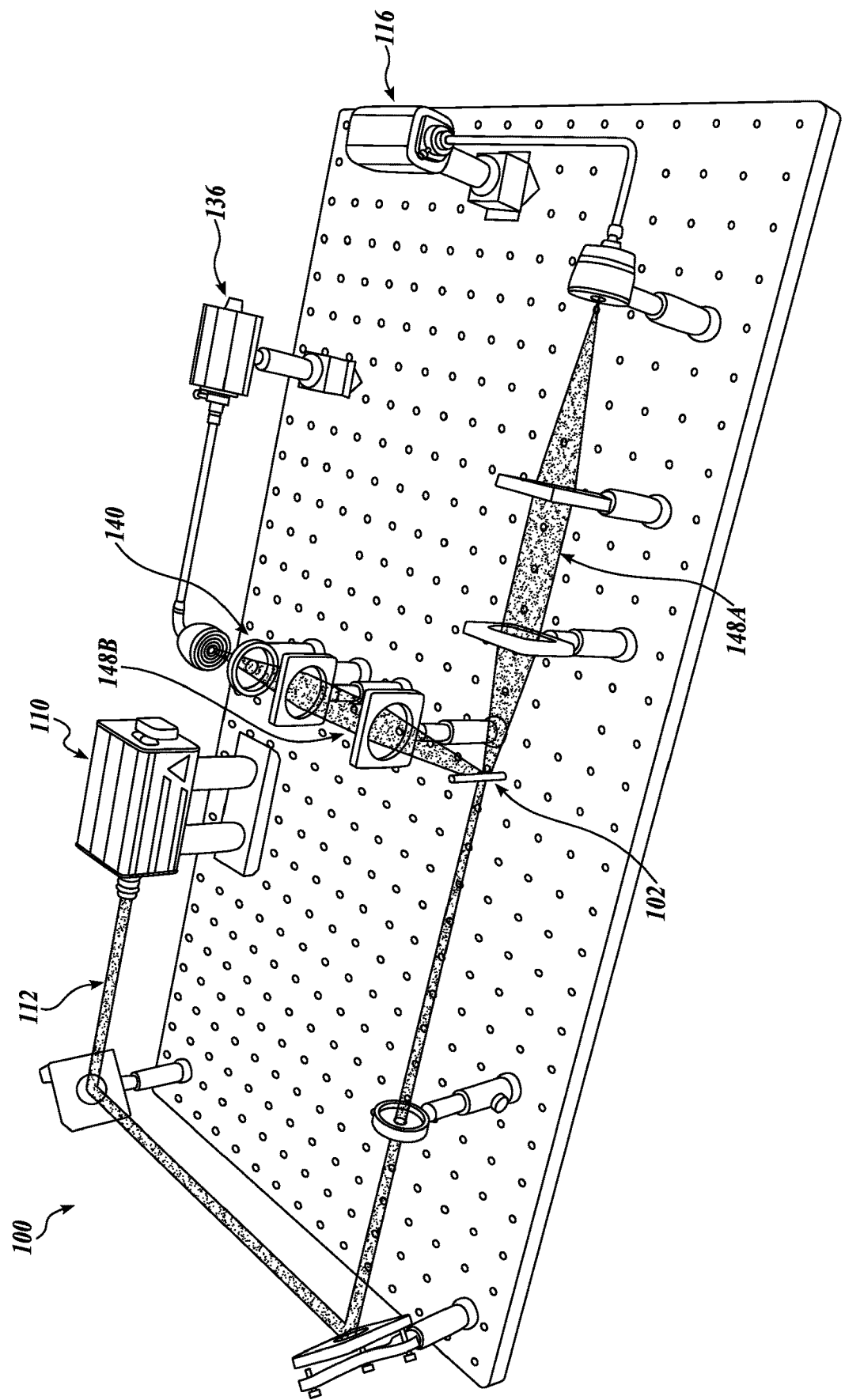
FIG. 1B is a schematic illustration of optical components of the device of FIG. 1A, in accordance with an embodiment of the disclosure.
Figure 1C:
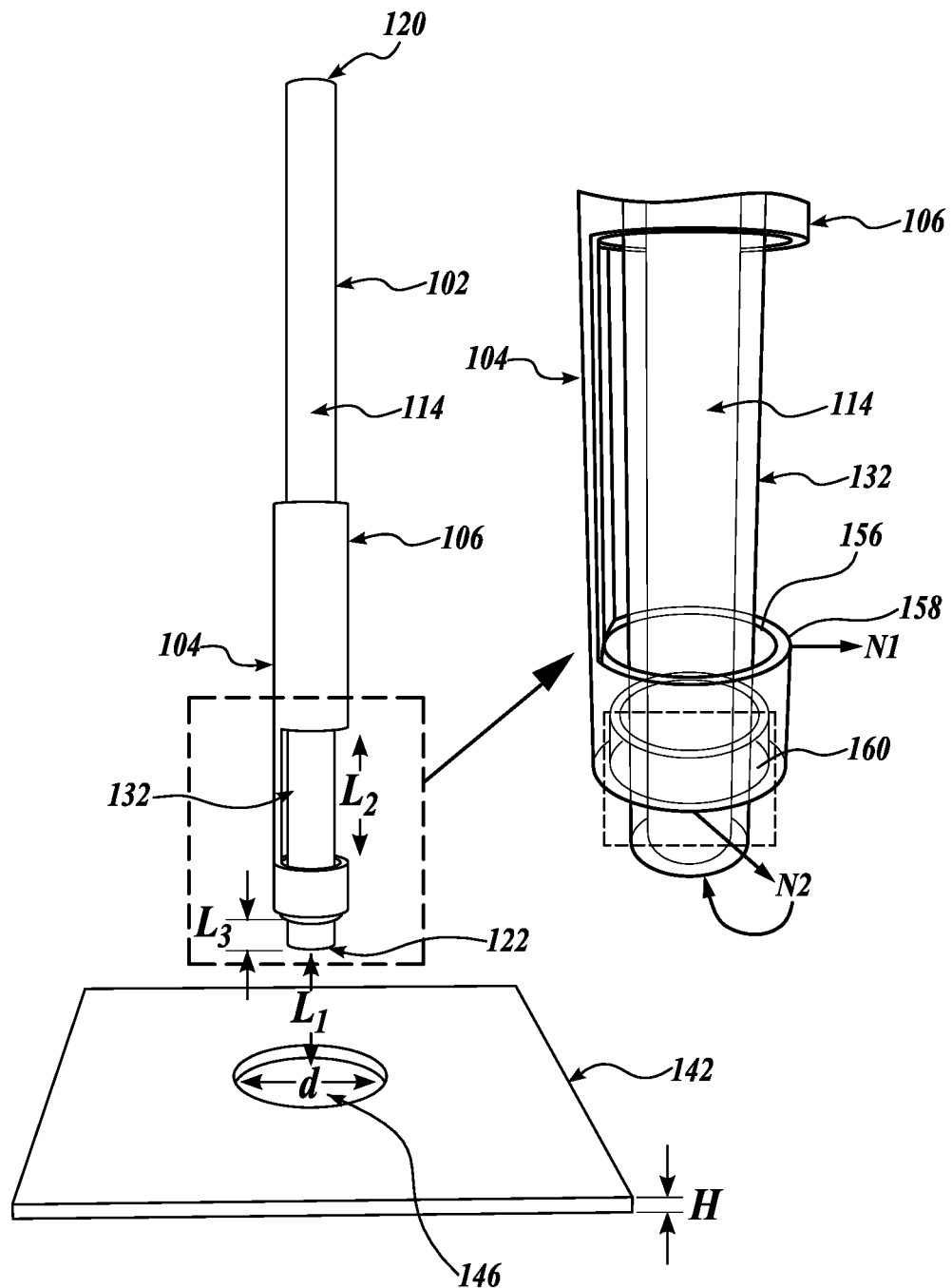
FIG. 1C is a schematic illustration of a capillary-based nozzle of the device of FIG. 1A, in accordance with an embodiment of the disclosure.

In an embodiment, the devices of the present disclosure are configured to produce droplets in a generally automated manner, such as with little or free of input from a user. In that regard, attention is directed to FIGS. 1A-1C, in which a device according to an embodiment of the disclosure is illustrated. FIG. 1A is a schematic illustration of the device. FIG. 1B is an illustration of optical components of the device. FIG. 1C is an illustration of a capillary and a capillary holder of the device of FIG. 1A.

In the illustrated embodiment, the device is shown to include a capillary, an electrode in conductive communication with the capillary and a power source; a light source positioned to illuminate the lumen of the capillary; photodetector, shown here as an avalanche photodiode (APD), and a controller, shown here as a desktop computer, operatively coupled to light source, the electrode, and the photodetector.

The capillary of the device defines a lumen and includes a first end coupleable to a fluid source; and a second end opposite the first end. As shown, the electrode is in conductive communication with the second end of the capillary and a power source. In this regard, the electrode is configured to apply a voltage to the second end of the capillary, such as a voltage sufficient to eject a droplet therefrom. While a positive voltage is shown applied to the electrode, a negative voltage applied may be applied to the electrode, such as where a different voltage is applied to another component of the device sufficient to eject a droplet from the second end of the capillary.

As above, the device includes a light source positioned to illuminate the lumen of the capillary and, in operation, contents of the lumen, such as those in a fluid disposed in the lumen. In an embodiment, the light source is a laser. In an embodiment, the light source comprises a light emitting diode. In an embodiment, the light source comprises a lamp. In an embodiment, the light source further comprises an emission filter, such as a band-pass filter.

In an embodiment, the light source emits infrared light. In an embodiment, the light source emits visible light. In some aspects, the light source emits light having a wavelength between about 200 nanometers and about 300 nanometers, about 250 nanometers and about 350 nanometers, about 300 nanometers and about 400 nanometers, about 350 nanometers and about 450 nanometers, about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, about 900 nanometers and about 1000 nanometers, about 950 nanometers and about 1050 nanometers, about 1000 nanometers and about 1100 nanometers, about 1150 nanometers and about 1250 nanometers, or about 1200 nanometers and about 1300 nanometers are used. In some aspects, the light source emits light having a wavelength between 200 nanometers and 300 nanometers, 250 nanometers and 350 nanometers, 300 nanometers and 400 nanometers, 350 nanometers and 450 nanometers, 400 nanometers and 500 nanometers, 450 nanometers and 550 nanometers, 500 nanometers and 600 nanometers, 550 nanometers and 650 nanometers, 600 nanometers and 700 nanometers, 650 nanometers and 750 nanometers, 700 nanometers and 800 nanometers, 750 nanometers and 850 nanometers, 800 nanometers and 900 nanometers, 850 nanometers and 950 nanometers, 900 nanometers and 1000 nanometers, 950 nanometers and 1050 nanometers, 1000 nanometers and 1100 nanometers, 1150 nanometers and 1250 nanometers, or 1200 nanometers and 1300 nanometers are used.

In an embodiment, the light source includes a plurality of individual light sources configured to emit light having a plurality of wavelengths, such as light configured to excite a plurality of chromophores or other light-sensitive components of one or more fluids disposed in the lumen of the capillary. In certain embodiments, such chromophores or other light-sensitive components absorb light in different wavelength ranges corresponding to emission wavelengths ranges of the plurality of light sources.

The device of FIG. 1A is shown to include a photodetector. As shown, the photodetector is positioned to absorb light from within the lumen. The photodetector is further configured to generate an electrical signal, such as for receipt by the controller, in response to the light from within the lumen. As discussed further herein, such an electrical signal may be used to trigger application of a voltage to the electrode and/or actuate sorting mechanisms for the droplets ejected by the capillary.

In an embodiment, the photodetector is selected from the group consisting of an avalanche photodiode, a silicon photomultiplier, a photomultiplier tube, a complementary-metal-oxide-semiconductor sensor, a charge coupled device sensor, and combinations thereof. In an embodiment, the photodetector is an avalanche photodiode. In an embodiment, such an avalanche photodiode is suitable to trigger or actuate functions of the device in which it is desirable to limit triggering or actuation of such functions below a threshold.

In an embodiment, the photodetector is positioned to absorb fluorescent or other light emitted from within the lumen of the capillary. In that regard, the photodetector is configured to generate an electrical signal in response to and based upon fluorescent light emitted from within the lumen of the capillary. As discussed further herein, such fluorescent light can include fluorescent light generated by a fluorophore, such as a fluorophore associated with a cell, cell portion, biological particle, nucleic acid, and the like, disposed within the lumen and excited by the light source. In an embodiment, the photodetector is positioned to absorb scattered light scattered off of a scattering source within the lumen of the capillary. In that regard, the photodetector is configured to generate an electrical in response to and based upon absorbed scattered light. In an embodiment, the photodetector is positioned to absorb forward scattered, back scatter, side scatter, or the like from within the lumen of the capillary. Such absorbed light can indicate the presence of a scattering source within the lumen of the capillary, such as a cell, portion of a cell, biological particle, and the like. As discussed further herein, such electrical signals based upon the scattered and/or fluorescent light can be used, for example, in applying voltages to the electrodes, manipulating stages of the device, and sorting droplets ejected from the second end of the capillary.

As shown in FIG. 1A, the device includes a single photodetector positioned to absorb light from within the lumen of the capillary. In an embodiment, the device includes two or more photodetectors positioned to absorb light from within the lumen of the capillary. In an embodiment, the device includes a first photodetector positioned to absorb scattered light scattered off of a scattering source within the lumen of the capillary and a second photodetector positioned to absorb fluorescent light emitted from within the lumen of the capillary. In that regard, the device is configured to generate an electrical signal based upon absorbed scattered light and a second electrical signal configured to generate a second electrical signal based upon absorbed fluorescent light.

As shown in FIG. 1B, the first photodetector, APD1, is positioned for detecting forward scatter of objects within the lumen of the capillary, such as a single cell carried in the lumen for scatter-triggered single-cell dispensing; and the second photodetector, APD2, is positioned for fluorescence detection to trigger fluorescence-activated sorting and dispensing events. In this regard, in an embodiment, individual photodetectors can be configured to assist in the performance of distinct functions, such as dispensing or ejecting droplets and sorting of such droplets once dispensed or ejected. For example, in an embodiment, a voltage is applied to the electrode to eject a droplet from the capillary based on an electrical signal based on scattered light absorbed by a photodetector and the moveable stage is moved relative to the second end of the capillary based on an electrical signal based on fluorescent light absorbed by another photodetector.

Figures 13A, 13B:
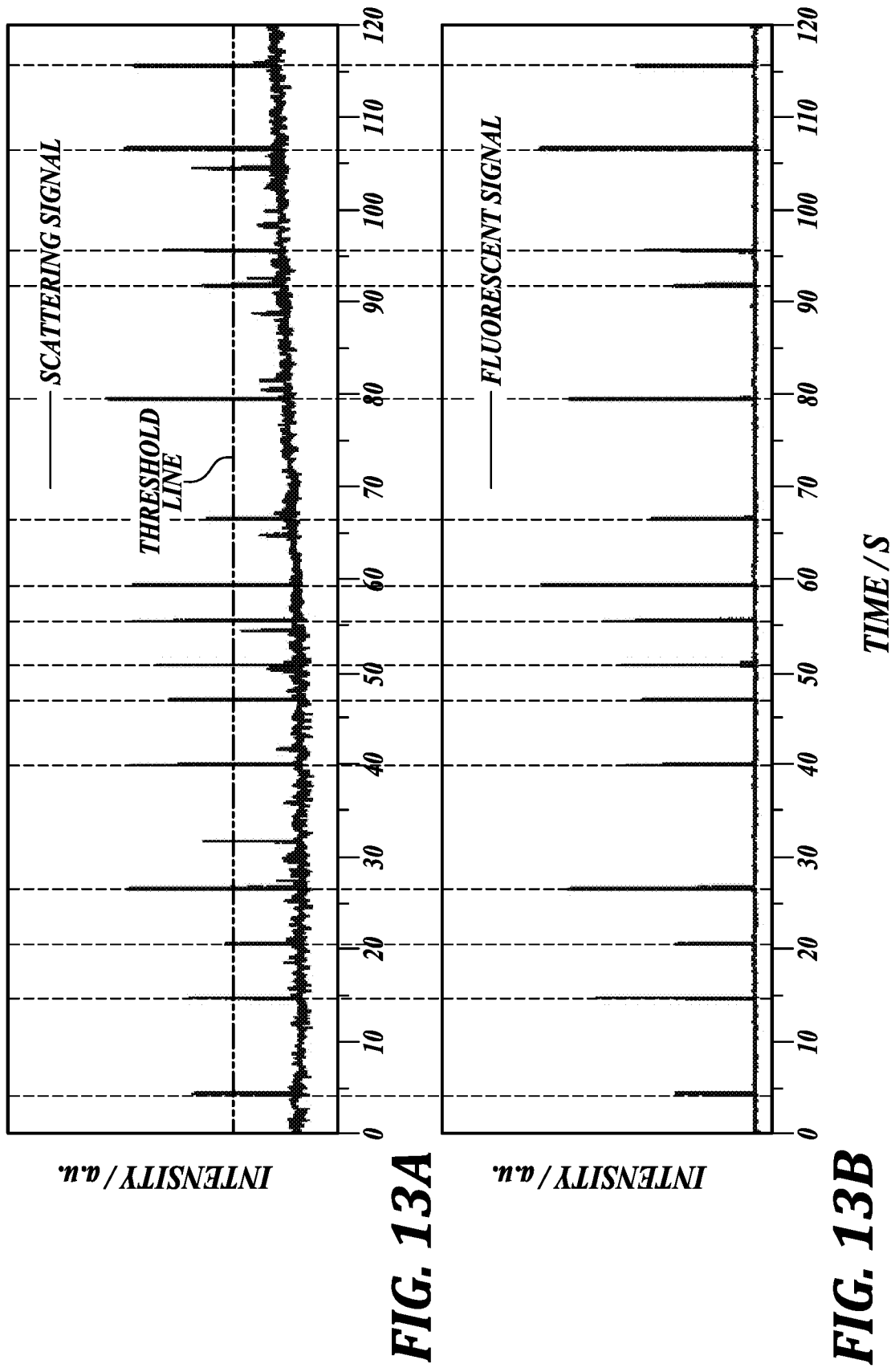
FIGS. 13A and 13B illustrate a comparison of scatter signal-activated dispensing and fluorescence-activated sorting, where a segment of the APD trace showing the scattering signal (13A) and fluorescence signal (13B) from the cells.

FIGS. 13A and 13B illustrate a comparison of scatter signal-activated dispensing and fluorescence-activated sorting, where a segment of the APD trace showing the scattering signal (13A) and fluorescence signal (13B) from the cells. K562 cells were labeled with the membrane dye FM1-43 and illuminated within the lumen of the capillary with light configured to fluoresce the FM1-43. As shown, the scattering signals over a threshold line generally correspond in time to fluorescent signals. The two unpaired peaks in FIG. 13A were from the dust in cell sample, which may cause the false-positive dispensing. In this regard, scattering signals and fluorescent signals can be used in conjunction to eject a droplet containing an analyte and sort the droplet containing the analyte.

As shown, the device further includes a controller operatively coupled to the photodetector, the light source, and the moveable stage. The controller can include a processor and a machine-readable storage medium. As shown, the controller is a desktop computer; however, other controllers, such as a laptop controller, a tablet, a mobile phone, and the like, are possible. In an embodiment, the controller includes logic that when executed by the controller, causes the device to perform operations. In an embodiment, the operations include detecting the light from within the lumen based on the electrical signal from the photodetector. As discussed further herein, in an embodiment, such an electrical signal is indicative of the presence of an analyte disposed in the lumen of the capillary and may be used to induce ejection droplets from the capillary and to sort droplets ejected from the second end of the capillary containing the analyte.

While analyte detection is described herein with respect to optical detection, it will be understood that other detection schemes are possible. Such detection schemes can include, for example, detection schemes based on electrical characteristics, such as electrical impedance or electrical conductance, of objects or fluid passing through the capillary. Such detection schemes may be suitable, for example, to detect cells, biological particles, portions of cells, droplets, and the like passing through the capillary and sorting droplets ejected from the capillary based such detection.

In an embodiment, the operations include applying, with the power source, a voltage to the electrode sufficient to eject a droplet from the second end of the capillary. In an embodiment, the voltage applied to the electrode is in a range of about 0.1 kV to about 10.0 kV. In an embodiment, the voltage applied to the electrode is in a range of about 0.9 kV to about 3.0 kV. In an embodiment, the voltage applied to the electrode is sufficient to eject an aqueous droplet from the second end of the capillary, such as where the device is coupled to an aqueous fluid source. In that regard, in an embodiment, the voltage applied to the electrode is in a range of about 1.5 kV to about 3.0 kV. In an embodiment, the voltage applied to the second end of the capillary is sufficient to eject a water-in-oil emulsion from the second end of the capillary, such as where the device is coupled to a fluid droplet source. In that regard, in an embodiment, the voltage applied to the electrode is in a range of about 0.9 kV to about 1.5 kV.

In an embodiment, the voltage applied to the electrode is in a range of about 0.1 kV to about 1.0 kV. In an embodiment, the voltage applied to the electrode is in a range of about 1.0 kV to about 2.0 kV. In an embodiment, the voltage applied to the electrode is in a range of about 2.0 kV to about 3.0 kV. In an embodiment, the voltage applied to the electrode is in a range of about 3.0 kV to about 4.0 kV. In an embodiment, the voltage applied to the electrode is in a range of about 4.0 kV to about 5.0 kV. In an embodiment, the voltage applied to the electrode is in a range of about 5.0 kV to about 6.0 kV. In an embodiment, the voltage applied to the electrode is in a range of about 6.0 kV to about 7.0 kV. In an embodiment, the voltage applied to the electrode is in a range of about 7.0 kV to about 8.0 kV. In an embodiment, the voltage applied to the electrode is in a range of about 8.0 kV to about 9.0 kV. In an embodiment, the voltage applied to the electrode is in a range of about 9.0 kV to about 10.0 kV.

In an embodiment, the power source is configured to apply an alternating current to the electrode. In an embodiment, the peak voltage applied with an alternative current is a range of about 0.1 kV to about 1.0 kV. In an embodiment, the peak voltage applied to the electrode is in a range of about 1.0 kV to about 2.0 kV. In an embodiment, the peak voltage applied to the electrode is in a range of about 2.0 kV to about 3.0 kV. In an embodiment, the peak voltage applied to the electrode is in a range of about 3.0 kV to about 4.0 kV. In an embodiment, the peak voltage applied to the electrode is in a range of about 4.0 kV to about 5.0 kV. In an embodiment, the peak voltage applied to the electrode is in a range of about 5.0 kV to about 6.0 kV. In an embodiment, the peak voltage applied to the electrode is in a range of about 6.0 kV to about 7.0 kV. In an embodiment, the peak voltage applied to the electrode is in a range of about 7.0 kV to about 8.0 kV. In an embodiment, the peak voltage applied to the electrode is in a range of about 8.0 kV to about 9.0 kV. In an embodiment, the peak voltage applied to the electrode is in a range of about 9.0 kV to about 10.0 kV.

In an embodiment, such a voltage is applied constantly to eject, for example, a steady stream of droplets from the capillary. As discussed further herein, such a steady stream of droplets can be sorted based on contents of individual droplets. In an embodiment, the voltage is applied periodically, such as based one or more electrical signals from one or more photodetectors or based on a user input.

As above, in an embodiment, the voltage is sufficient to eject the droplet through electrohydrodynamic actuation. As used herein, the term "electrohydrodynamic actuation" refers to the use of an electrical field and/or electrical potential to generate the flow of or force on one or more liquids. In some aspects of the disclosure, electrohydrodynamic actuation provides a mechanism for the controlled generation of droplets in a gas phase, such as for ejecting droplets from the capillary into air.

Such electrohydrodynamic actuation is suitable to provide a controllable force exerting on the droplet. As discussed further herein, such controllable force may be used to tailor droplet size and a frequency at which droplets are emitted from the second end of the capillary. FIGS. 15A-15H are COMSOL® simulations of spatial electric-field distribution around capillary, in accordance with an embodiment of the disclosure. The voltage difference between the capillary (positive voltage) and, for example, an electrically conductive plate (grounded) accelerates the droplet downward toward the hole. Likewise, are graphic illustrations of flow rate of a fluid through a capillary as a function of voltage applied to the capillary at various capillary inner diameters. As shown, as a greater voltage is applied to the capillary flow rate of fluid through the capillary increases.

In an embodiment, the device includes a stage configured to carry a multi-well plate comprising two or more wells; and a source of motion configured to move the stage relative to the second end of the capillary. In an embodiment, the source of motion is configured to move the stage such that stage is positioned to accept a droplet ejected from the capillary. In an embodiment, the source of motion is configured to move the stage orthogonally relative a central axis of the lumen of the capillary, as illustrated in FIG. 1A. In this regard, the device is configured to selectively eject droplets from the second end of the capillary into the wells of the multi-well plate. In an embodiment, the controller includes logic that when executed by the controller, causes the device to perform operations including moving the stage with the source of motion relative to the second end of the capillary such that the second end of the capillary is positioned to eject the droplet for receipt by one of the two or more wells based upon an electrical signal from one of the one or more photodetectors. In this regard, the device is configured to selectively eject droplets into a multi-well plate carried by the stage based upon light from within the lumen of the capillary. Accordingly, in operation, the device may be used to sort droplets ejected from the second end of the capillary based upon the contents of such droplets, including for examples cells, cells portions, biological particles, and nucleic acid disposed therein.

In an embodiment, the controller includes logic that when executed by the controller, causes the device to perform operations including moving the stage with the source of motion relative to the second end of the capillary such that the second end of the capillary is positioned to eject the droplet for receipt by one of the two or more wells when the electrical signal is at or above a threshold. In this regard, in an embodiment, the device is configured to eject a droplet into one of the two or more wells of the multi-well plate when an analyte of interest is disposed within the droplet as discussed further herein with respect to FIGS. 3B and 4B. Such a selected droplet, such as a droplet including a selected cell, cell portion, biological particle, amplified nucleic acid, and the like, may be further analyzed. Correspondingly, in an embodiment, the controller includes logic that when executed by the controller, causes the device to perform operations including moving the stage with the source of motion relative to the second end of the capillary such that the second end of the capillary is positioned to eject the droplet for receipt by another of the two or more wells when the electrical signal is below the threshold. In this regard, droplets that do not include analytes of interest are ejected into another well, such as a waste well, in order to isolate such droplets from the selected droplets. See, for example, FIG. 3A. While sorting functions are described herein with respect to a moveable stage, it will be understood that droplets ejected from the second of the capillary can be directed into one well or another through application of an electric field. Such an electric field may be suitable to deflect or otherwise change a trajectory of a droplet ejected from the second end of the capillary such that the ejected droplet is configured to be received by a well of a multi-well plate carried by the stage. The electric field can be applied through one or more device components in conductive communication with the power source, such as the electrically conductive plate.

In an embodiment, the threshold is a predetermined threshold. In this regard, the device is configured, for example, to eject a droplet into a selected well for further analysis when an electrical signal from the photodetector is at or above a predetermined level indicative of an analyte within the capillary of the lumen. In an embodiment, the predetermined threshold is variable. Accordingly, in an embodiment, the controller is configured to vary the threshold based upon one or more previous measurements of electrical signals generated by the photodetector.

Figure 4C:
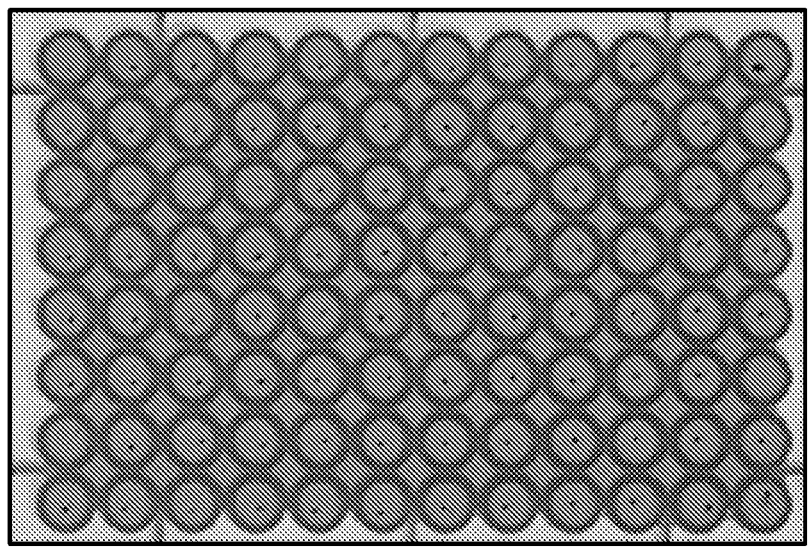
FIG. 4C is a fluorescence image of a 96-well plate showing the successful dispensing results, in accordance with an embodiment of the disclosure.
Figure 5A:
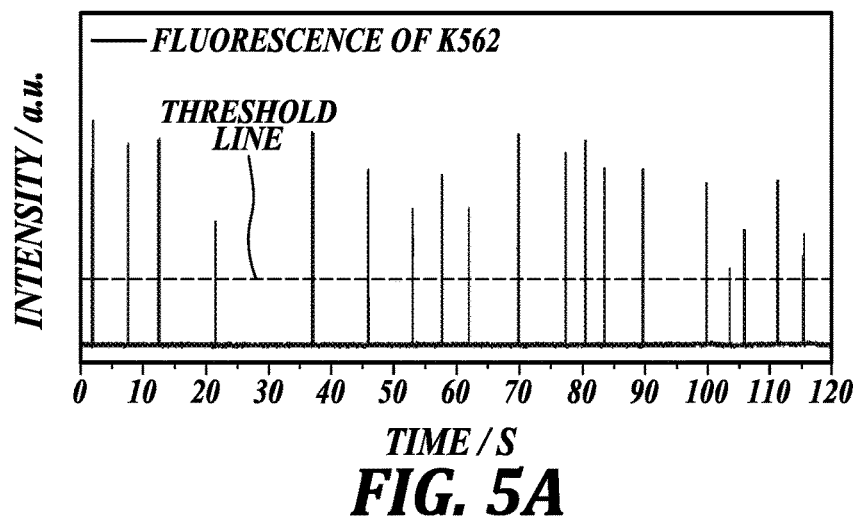
FIG. 5A is a segment of an APD trace from K562 cells labeled with the membrane dye FM1-43.
Figure 5B:
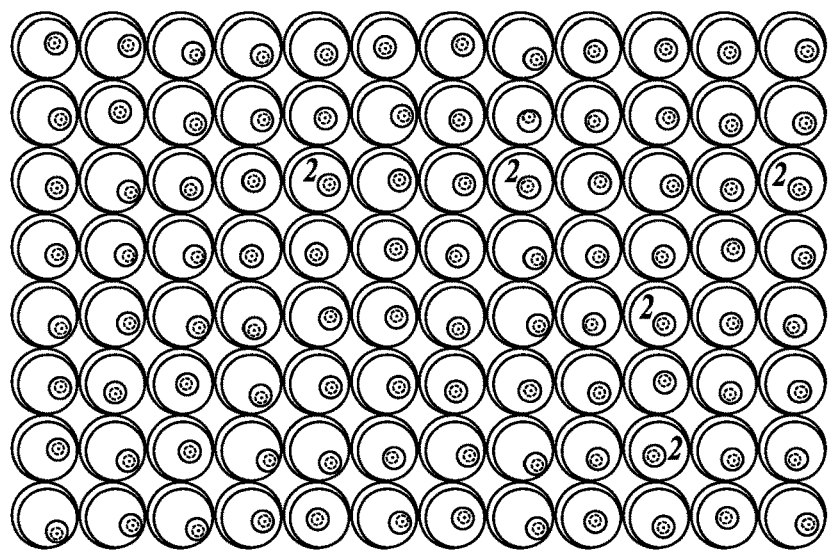
FIG. 5B is a fluorescence image of a 96-well plate showing the successful single-cell dispensing results, in accordance with an embodiment of the disclosure.
Figure 5C:
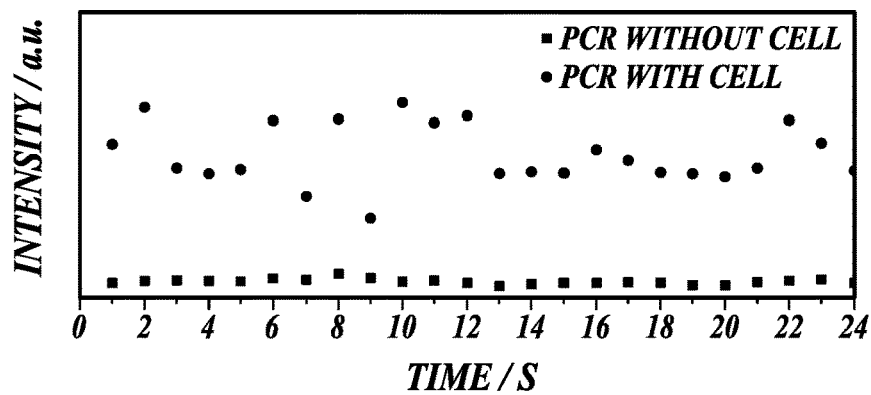
FIG. 5C graphically illustrates PCR-amplification results of Flt3 gene in single K562 cell in well plate, where the signal of wells containing single cell was well-separated from those without cells, in accordance with an embodiment of the disclosure.
Figure 6A:
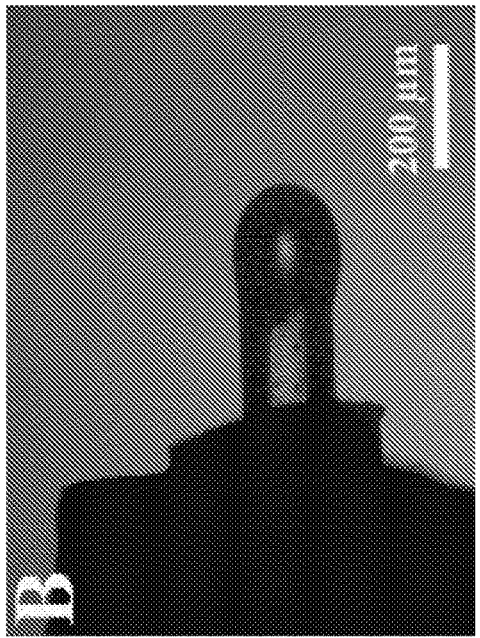
FIGS. 6A-6D are a series images showing high-voltage-controlled generation of oil droplets in the air from a capillary of a device, in accordance with an embodiment of the disclosure, where a voltage applied is 1.4 kV and a flow rate of oil is 10 μL/min.
Figure 6B:
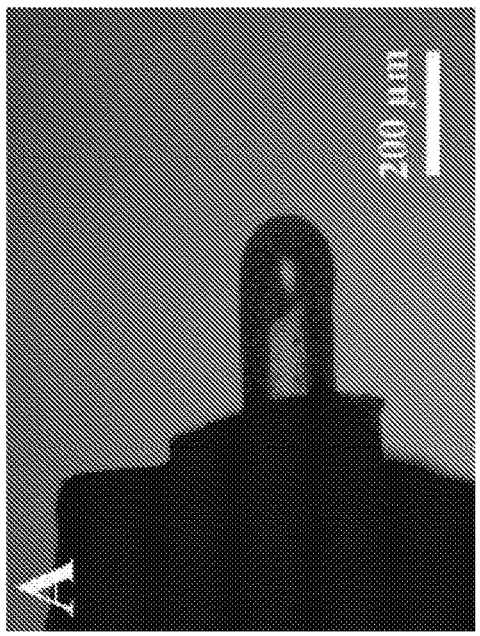
Figure 6C:
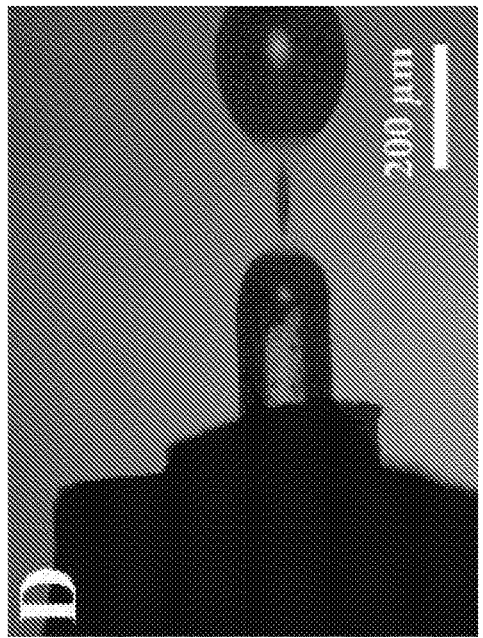
Figure 6D:
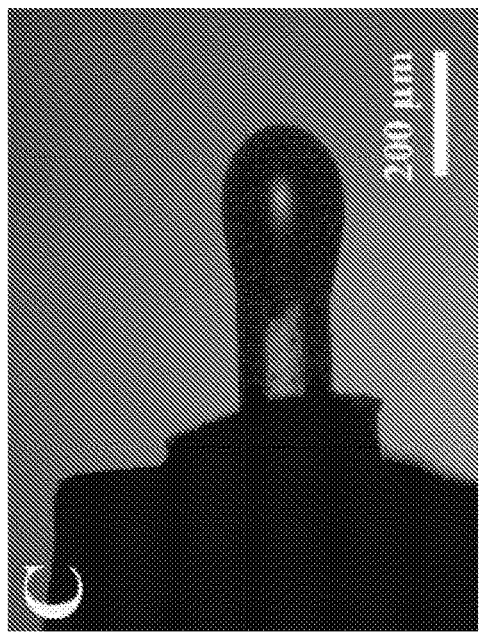
Figure 7A:
FIGS. 7A-7G are a series of images of discrete partitions having different specific volumes generated by adjusting a flow rate of injected oil and water, in accordance with an embodiment of the disclosure.
Figure 7B:
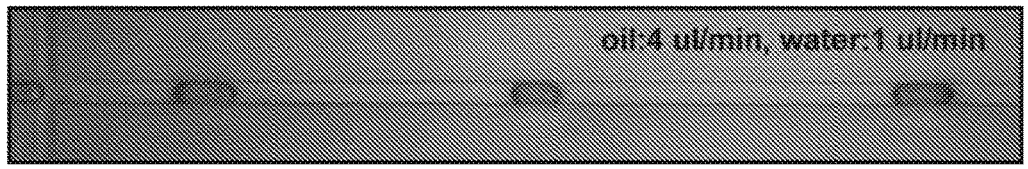
Figure 7C:
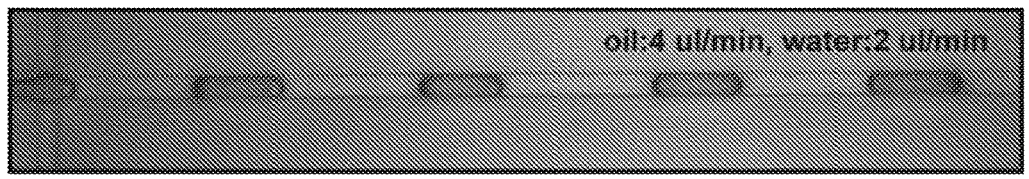
Figure 7D:
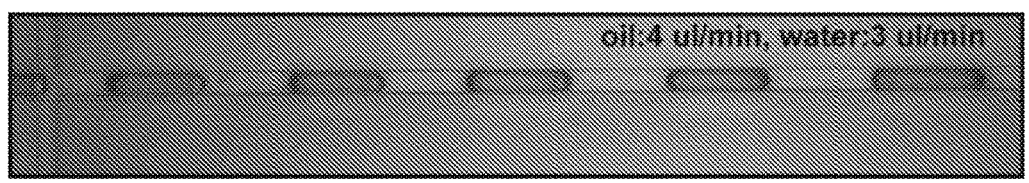
Figure 7E:
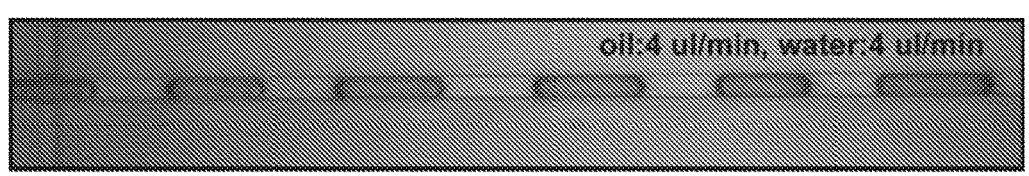
Figure 7F:
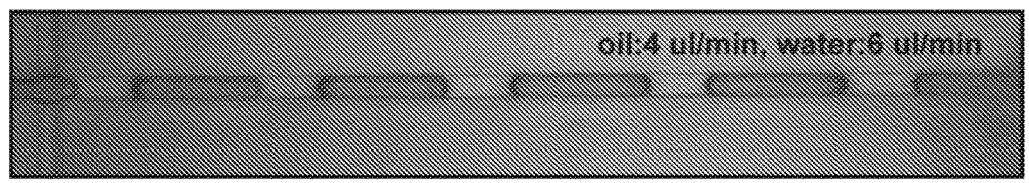
Figure 7G:
Figure 10A:
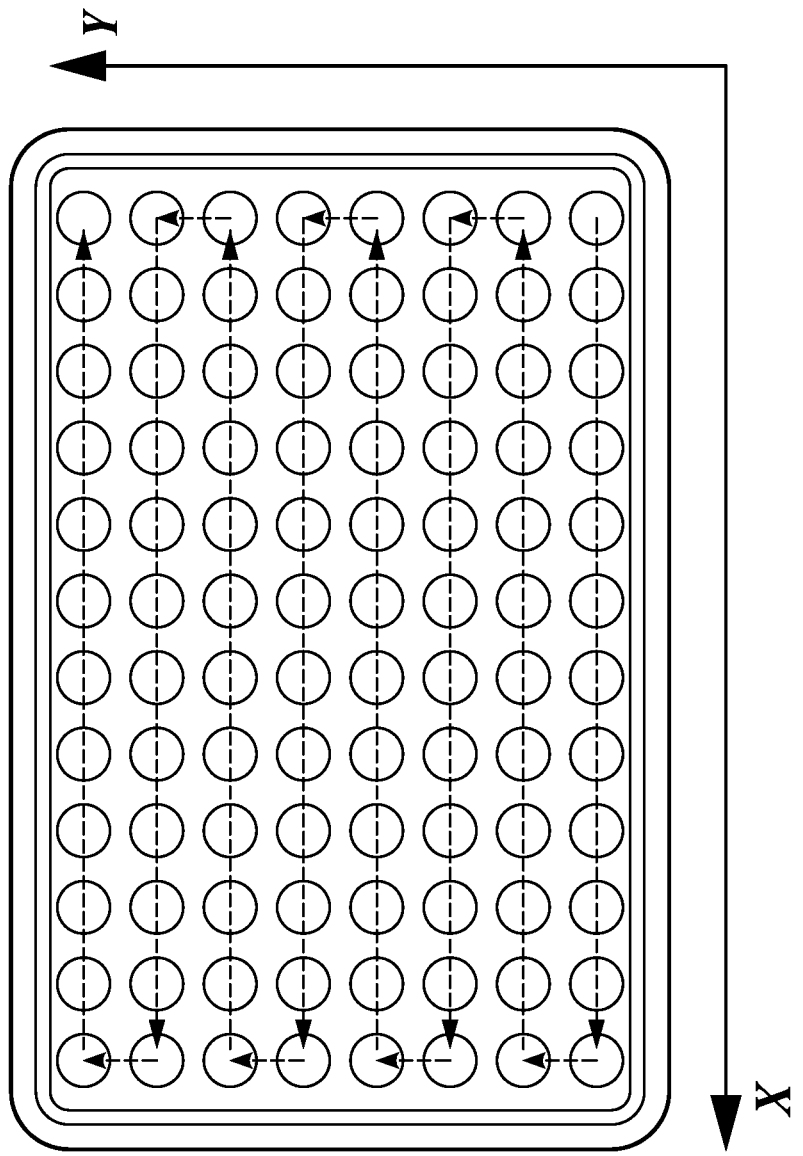
FIG. 10A graphically illustrates an example path of a second end of a capillary of a device, in accordance with an embodiment of the disclosure, relative to portions of a 96-well plate.

In an embodiment, the controller further includes logic that when executed by the controller, causes the device to perform operations including moving the stage with the source of motion relative to the second end of the capillary such that droplets ejected from the second end of the capillary are individually received by the two or more wells. In this regard, the device is configured, for example, to move the stage relative to the second end of the capillary in an ordered manner to emit a single droplet into each of the wells of the multi-well plate carried by the stage. While moveable stages are discussed herein, it will be understood that other configurations are possible, such as where the second end of the capillary is configured to move relative to the stage. In this regard, the stage may be stationary or may also be configured to move relative to the second end of the capillary. Such a configuration is also suitable to perform the soring functions described further herein. As shown in FIG. 10A, in an embodiment, the device is configured to raster the stage relative to the second end of the capillary to eject droplets from the capillary for individual receipt by the wells of the multi-well plate. Likewise, as shown in FIGS. 4C and 5C, in an embodiment, the device is configured to eject a single droplet containing a single cell into wells of the multi-well plate. Such cells individually disposed within the wells of the multi-well plate may be individually analyzed after ejection from the capillary. In an embodiment, sorting ejected droplets includes coordination of two or more of a droplet ejection rate, transit time on an ejected droplet between the second end of the capillary and a multi-well plate, and a rate at which the stage moves.

In an embodiment, the stage is conductively coupled to the power source. (See for example, FIG. 4A. In this regard, a voltage may be applied by the power source to the stage to apply an electric force to droplets generated at the second end of the capillary and to further electrohydrodynamic actuation of such droplets. Accordingly, in an embodiment, the device includes a second electrode coupled to the power source and disposed on the stage to contact a surface of the multi-well plate when the multi-well plate is carried by the stage. Further, in an embodiment, the controller is operatively coupled to the electrode and further includes logic that when executed by the controller, causes the device to perform operations including: applying a voltage to the second electrode different than the voltage applied to electrode. While a negative voltage is shown applied to the second electrode FIG. 4A, it will understood that other voltages, such as a positive voltage, are possible depending upon a voltage applied, for example, to the electrode in conductive communication with the capillary.

As discussed further herein with respect to FIGS. 9A-9C, the devices described herein may include a multi-well plate cover. Such a multi-well plate cover can be in conductive communication with the power source or an electrical ground. In this regard, the device is configured to direct droplets toward the wells of the multi-well plate and/or disperse static charge of the multi-well plate. Likewise, in an embodiment, the device includes a wire or other conductive member configured to contact a surface of the multi-well plate configured to face the second end of the capillary. Such a wire or other conductive member may be conductively coupled to the power source or an electrical ground.

In an embodiment, and as shown in FIG. 1C, the device includes a capillary holder configured to carry the capillary. In an embodiment, the capillary holder is a portion of the electrode in conductive communication with the second end of the capillary. In this regard, the capillary holder may comprise electrically conductive materials. In an embodiment, the capillary holder comprises an outer tube; an inner tube coaxially carried by the outer tube; and a conductive spacer conductively coupling the inner tube and the outer tube. In an embodiment, the outer tube and the inner tube comprise electrically conductive materials suitable to transmit a voltage from the power source to the second end of the capillary, such as a voltage sufficient to eject a droplet therefrom.

As shown in FIG. 1C, the capillary holder defines an illumination window shaped to expose an illumination portion of the capillary to light emitted from the light source. Accordingly, such an illumination window is suitably shaped for interrogating the illumination portion of the capillary and contents of the lumen within the illumination window. The illumination window is suitable for illumination with a light source, such as to excite a chromophore and/or for interrogating the lumen through visual inspection by a user. In an embodiment, a height of the illumination window is in a range of about 1 µm to about 300 µm. In an embodiment, a height of the illumination window is in a range of about 5 µm to about 100 µm. In an embodiment, a height of the illumination window is in a range of about 10 µm to about 50 µm.

In an embodiment, the electrode comprises a transparent conductive film. Such a transparent conductive film is suitable to apply a voltage to the second end of the capillary to eject a droplet therefrom. Further, because the transparent conductive film is optically transmissive, it is suitable to optically interrogate the lumen of the capillary, such as by illuminating a portion of the lumen and detecting light from within the lumen of the capillary. In an embodiment, the transparent conductive film comprises a transparent conductor selected from the group consisting of indium tin oxide, a silver wire, fluorine tin oxide, doped zinc oxide, graphene, carbon nanotubes, poly(3,4-ethylenedioxythiophene), poly (3,4-ethylenedioxythiophene):poly(styrene sulfonate), poly (4,4-dioctyl cyclopentadithiophene), and combinations thereof.

The devices described herein are configured to eject droplets of variable size and volume. Such droplet sizes and volumes can be varied based upon manipulation of a number of device parameters. In an embodiment, the device is configured to eject a droplet configured to carry a single cell or the contents of a single cell or a small group of cells. As discussed further herein with respect to FIGS. 18A-18E and 19A-19C, such device parameters can include, for example, a voltage applied to the capillary, capillary inner diameter, capillary outer diameter, a distance between the second end of the capillary and an edge of the electrode, flow rate, and the like.

In an embodiment, the device is configured to eject droplets having an average diameter in a range of about 10 µm to about 2 mm. In an embodiment, the device is configured to eject droplets having an average diameter in a range of about 50 µm to about 1 mm. In an embodiment, the device is configured to eject droplets having an average diameter in a range of about 150 µm to about 350 µm. In an embodiment, the device is configured to eject droplets having an average diameter in a range of about 200 µm to about 300 µm. In an embodiment, the device is configured to eject droplets having an average diameter in a range of about 20 µm to about 200 µm. In an embodiment, the device is configured to eject droplets having an average diameter in a range of about 50 µm to about 150 µm.

In an embodiment, the device is configured to eject droplets having an average volume in a range of about 0.1 nL to about 500 nL. In an embodiment, the device is configured to eject droplets having an average volume in a range of about 1 nL to about 250 nL. In an embodiment, the device is configured to eject droplets having an average volume in a range of about 10 nL to about 500 nL. In an embodiment, the device is configured to eject droplets having an average volume in a range of about 50 nL to about 100 nL. In an embodiment, the device is configured to eject droplets having an average volume in a range of about 20 nL to about 200 nL. In an embodiment, the device is configured to eject droplets having an average volume in a range of about 50 nL to about 150 nL.

Generally, a larger distance between the second end of the capillary and the edge of the electrode (shown in FIG. 1C as distance L3) generates larger droplets. Accordingly, where smaller droplets may be desirable, such as when generating droplets meant to contain a single cell, a length of capillary extending past the electrode, such as may be determined by the distance between the second end of the capillary and the edge of the electrode, will be relatively small. When the distance between the second end of the capillary and an edge of the electrode is relatively small, a capillary holder, when present, may be configured to define a viewing window as a portion of the capillary extending past the electrode may be too small to interrogate. In an embodiment, a distance between the second end of the capillary and an edge of the electrode is in a range of about 1 μm to about 100 μm. In an embodiment, the distance between the second end of the capillary and the edge of the electrode is in a range of about 1 μm to about 10 μm. In an embodiment, the distance between the second end of the capillary and the edge of the electrode is in a range of about 1 μm to about 5 μm.

As shown in FIGS. 18A-18E relatively larger outer diameter of the capillary generally produces larger droplets. Accordingly, where smaller droplets may be desirable, such as when generating droplets meant to contain a single cell, the outer diameter may be relatively smaller. In an embodiment, an outer diameter of the capillary is in a range of about 100 μm to about 400 μm. In an embodiment, the outer diameter of the capillary is in a range of about 150 μm to about 360 μm. In an embodiment, the outer diameter of the capillary is in a range of about 150 μm to about 200 μm. In an embodiment, the outer diameter of the capillary is in a range of about 300 μm to about 400 μm.

In an embodiment, an inner diameter of the capillary is in a range of about 30 μm to about 150 μm. In an embodiment, the inner diameter of the capillary is in a range of about 50 μm to about 100 μm. In an embodiment, the inner diameter of the capillary is in a range of about 70 μm to about 90 μm.

Referring back to FIGS. 1A and 1C, the illustrated device is shown to include an electrically conductive plate defining an aperture. A shown, the aperture is positioned and sized to receive a droplet ejected from the second end of the capillary. In this regard, a droplet ejected from the capillary is configured to pass through the aperture.

In an embodiment, a potential difference between the electrode and the electrically conductive plate is configured to eject a droplet from the second end of the capillary. In this regard, the device may be configured to apply an electric force to fluid disposed in the capillary and to eject a droplet through application of an electric field to the second end of the capillary to polarize liquid disposed in the lumen of the capillary, resulting in an electric force between the droplet and the electrically conductive plate.

In an embodiment, the electrically conductive plate is in conductive communication with the power source. In an embodiment, the electrically conductive plate is in conductive communication with an electrical ground.

In an embodiment, a distance between the second end of the capillary and a surface of the electrically conductive plate is in a range of about 1 μm and about 300 μm. In an embodiment, the distance between the second end of the capillary and a surface of the electrically conductive plate is in a range of about 1 μm and about 100 μm. In an embodiment, the distance between the second end of the capillary and a surface of the electrically conductive plate is in a range of about 1 μm and about 10 μm. In an embodiment, the distance between the second end of the capillary and a surface of the electrically conductive plate is in a range of about 100 μm and about 1 mm. In an embodiment, the distance between the second end of the capillary and a surface of the electrically conductive plate is in a range of about 1 mm and about 10 mm.

In an embodiment, the device includes a multi-well plate cover being electrically conductive and defining two or more apertures. When the multi-well plate cover is disposed over a multi-well plate carried by the stage, the two or more apertures of the multi-well plate cover are configured to allow passage of droplets ejected from the second end of the capillary to the two or more wells of the multi-well plate. FIGS. 9A-9C illustrate a multi-well plate cover, in accordance with an embodiment of the disclosure. As shown, apertures of the multi-well plate cover are configured to register with apertures of the multi-well plate to allow passage of droplets through the apertures of the multi-well plate cover and into wells of the multi-well plate. As illustrated in and discussed further herein with respect to FIG. 4A, the multi-well plate cover may be conductively coupled to an electrical ground. Such an electrical ground may be suitable to disperse, for example, static charge of the multi-well plate that might otherwise deflect a droplet away from a well of the multi-well plate. In this regard, a droplet ejected from the second end of the capillary is more likely to be received by a well of the multi-well plate with a multi-well plate cover disposed over a multi-well plate and in conductive communication with an electrical ground.

In an embodiment, a number of the two or more apertures of the multi-well plate cover is selected from 2, 4, 6, 12, 24, 48, 96, 384 and 1,536. In this regard, the multi-well plate cover may be configured to allow passage of droplets through the apertures and into wells of conventional multi-well plates.

In an embodiment, the device includes a pump configured to flow fluid through capillary. As above, the device is coupleable to a fluid source, such as through fluidic coupling of a first end of the capillary to the fluid. Such a pump may be configured to flow fluid from the fluid source through the lumen of the capillary. In that regard, attention is directed to FIG. 14, in which a device, in accordance with an embodiment of the disclosure is illustrated. As shown, the device includes a capillary fluidically coupled to the pump, shown here as an automated syringe pump. Flow of the fluid through the capillary and a flow rate can be controlled, at least in part, by the pump. While a syringe pump is illustrated, it will be understood that other pumps may be used. In an embodiment, the pump is selected from the group consisting of external syringe pumps, pneumatic membrane pumps, vibrating membrane pumps, vacuum devices, electrokinetic pumps piezoelectric/ultrasonic pumps, electrohydrodynamic pumps, magnetohydrodynamic pumps, and combinations thereof.

Figure 14:
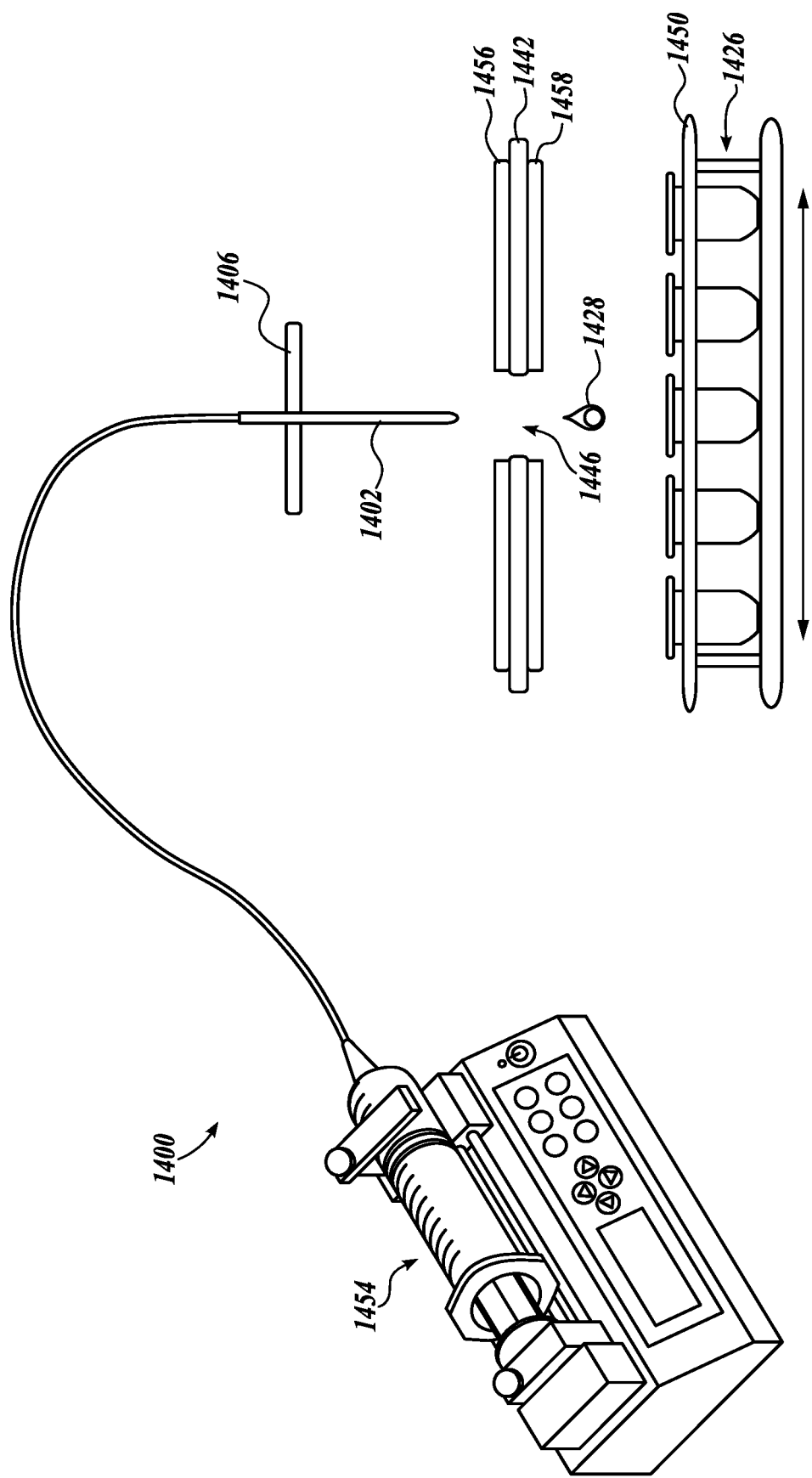
FIG. 14 is a schematic illustration of a system, in accordance with an embodiment of the disclosure.
Figure 15A:
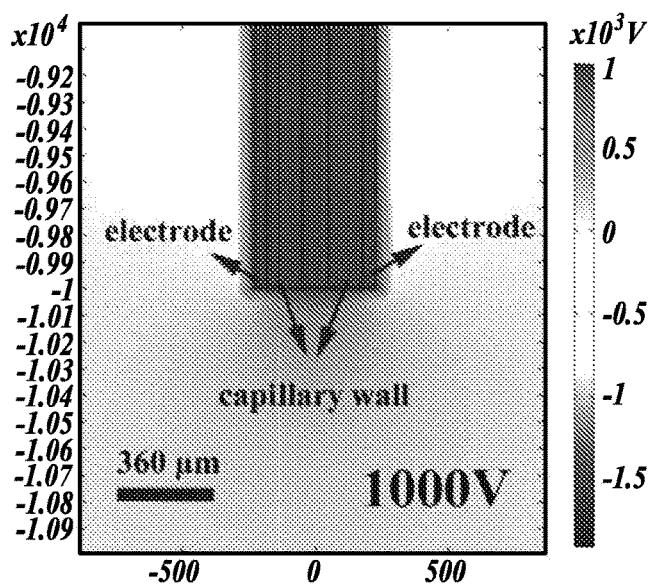
FIGS. 15A-15H are COMSOL® simulation images of spatial electric-field distribution around a capillary to which varying voltages are applied, in accordance with an embodiment of the disclosure.
Figure 15B:
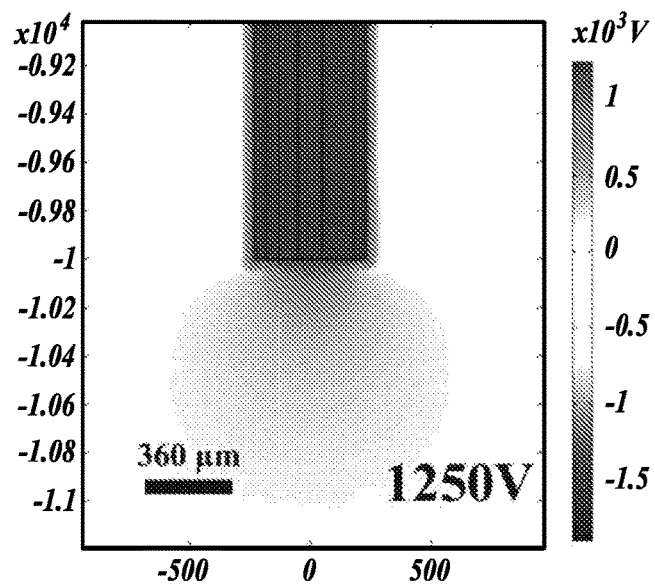
Figure 15C:
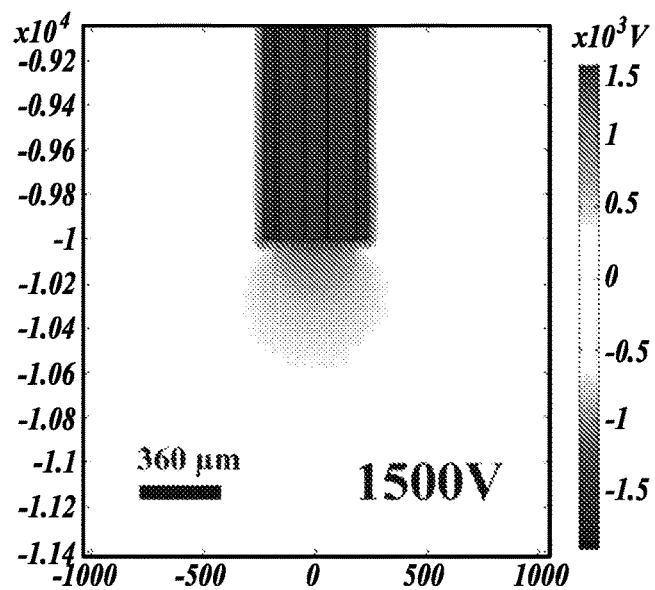
Figure 15D:
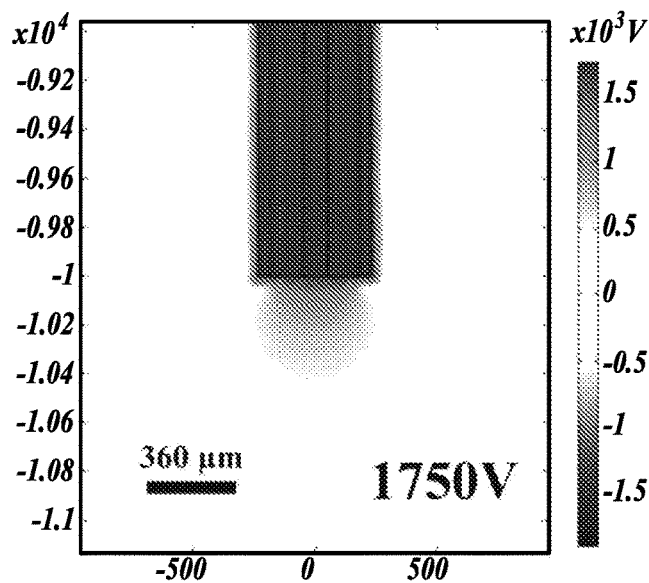
Figure 15E:
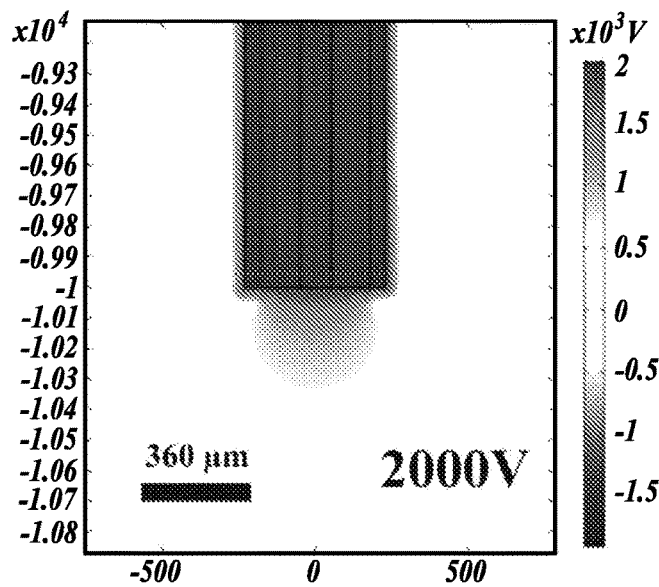
Figure 15F:
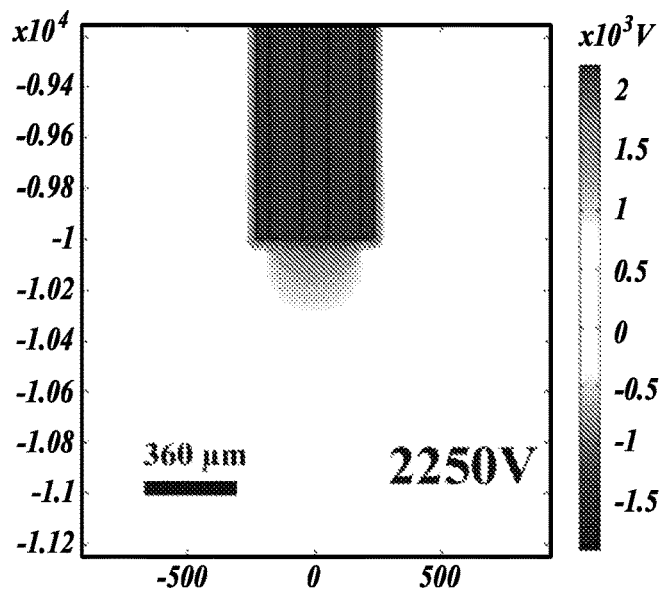
Figure 15G:
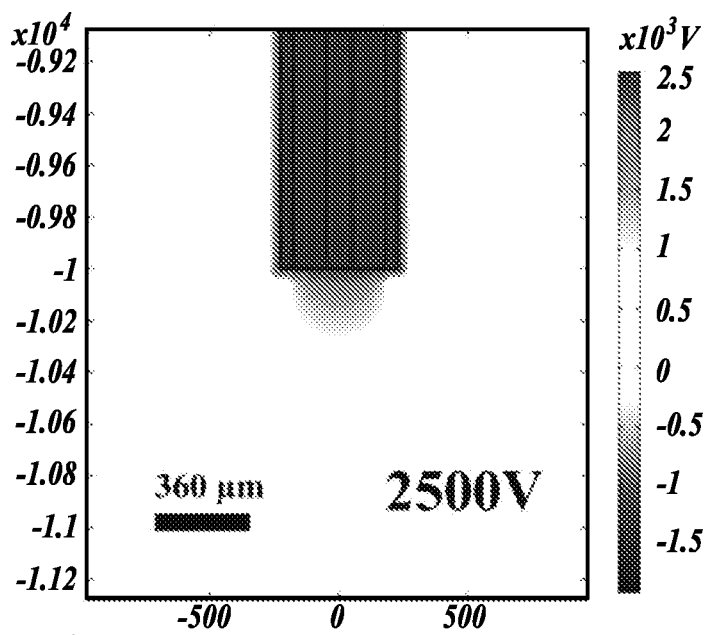
Figure 15H:
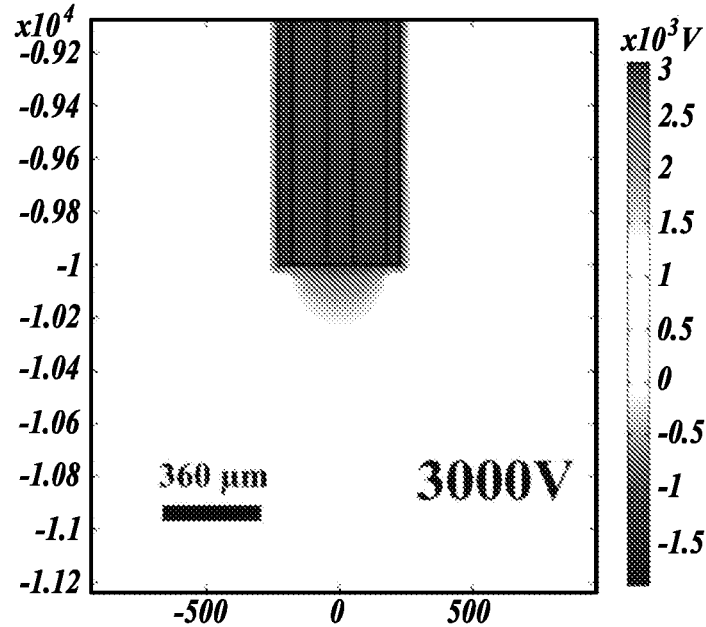
Figure 16A:
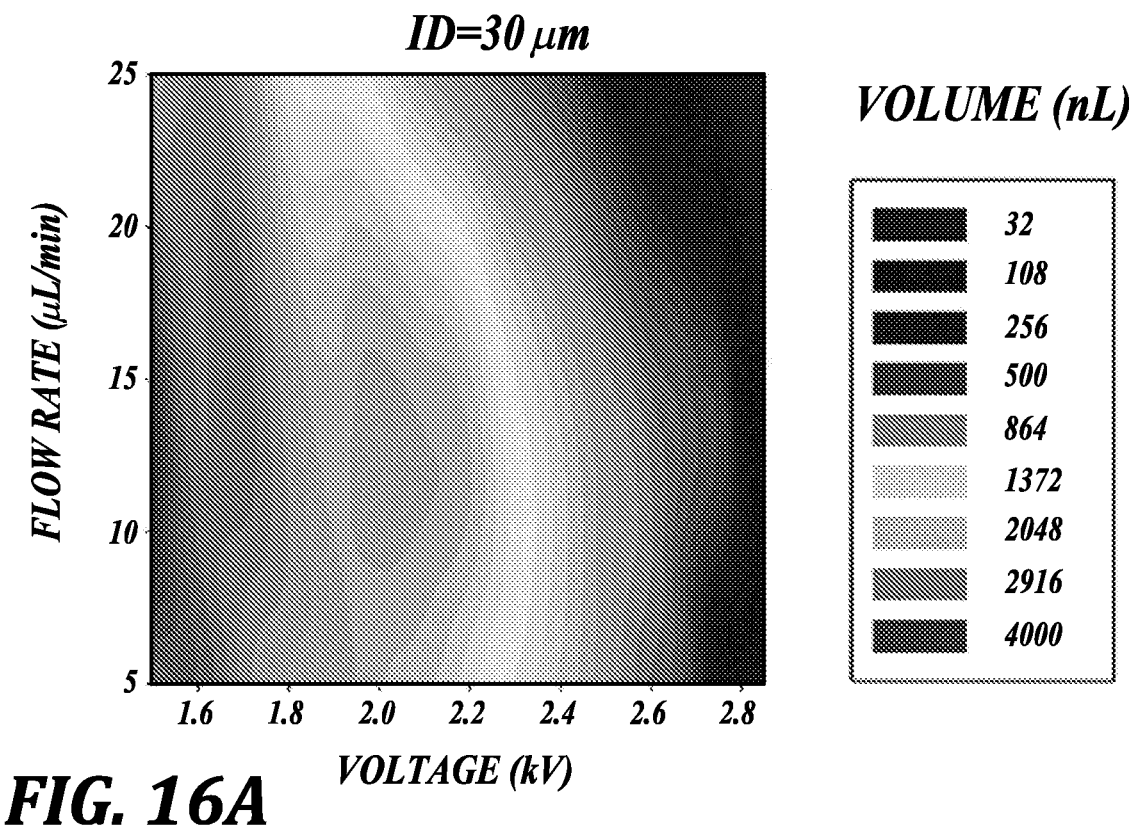
FIGS. 16A-16D are graphic illustrations of generated droplets volumes as a function of flow rate of a fluid through a capillary, voltage applied to the capillary and various capillary inner diameters.
Figure 16B:
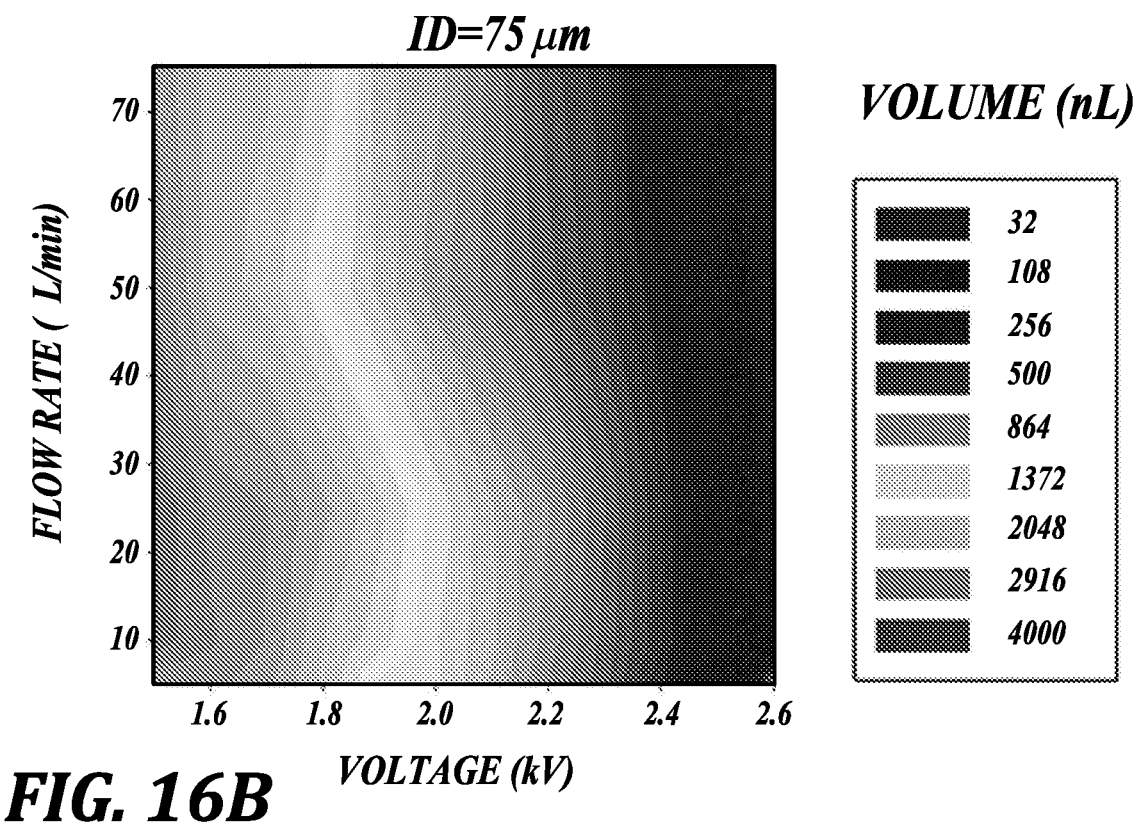
Figure 16C:
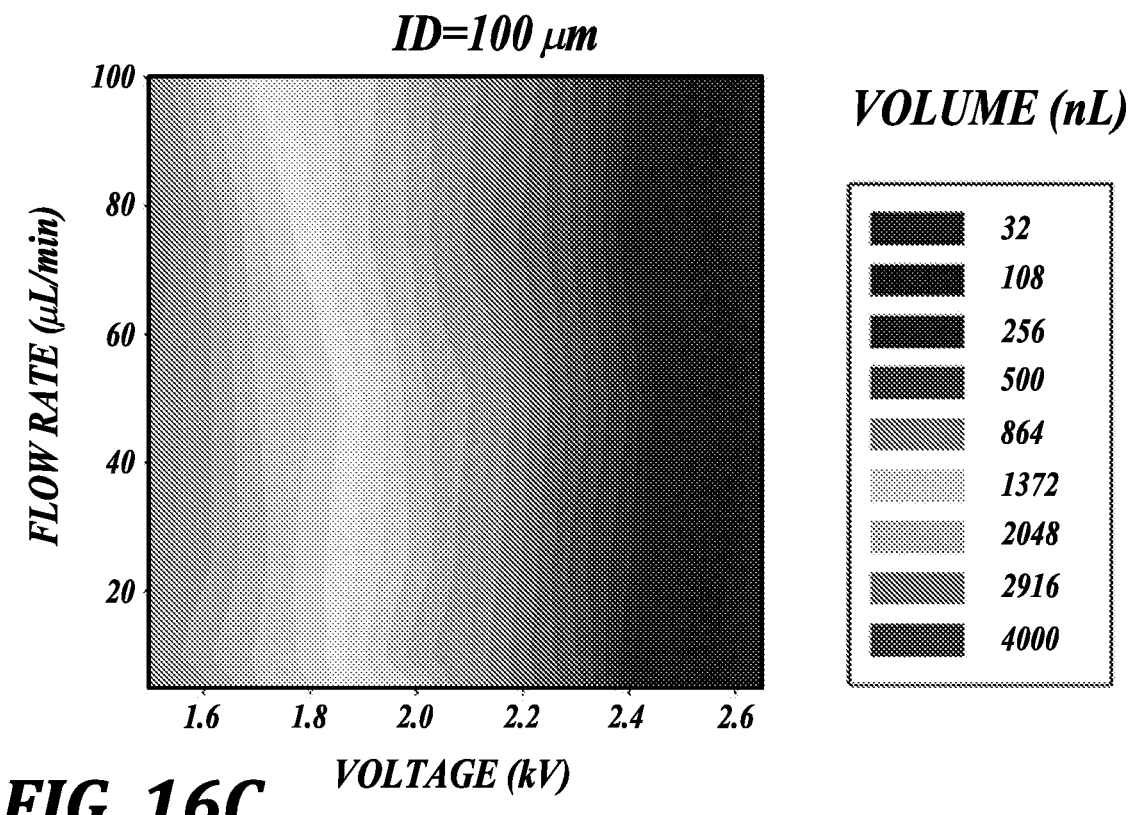
Figure 16D:
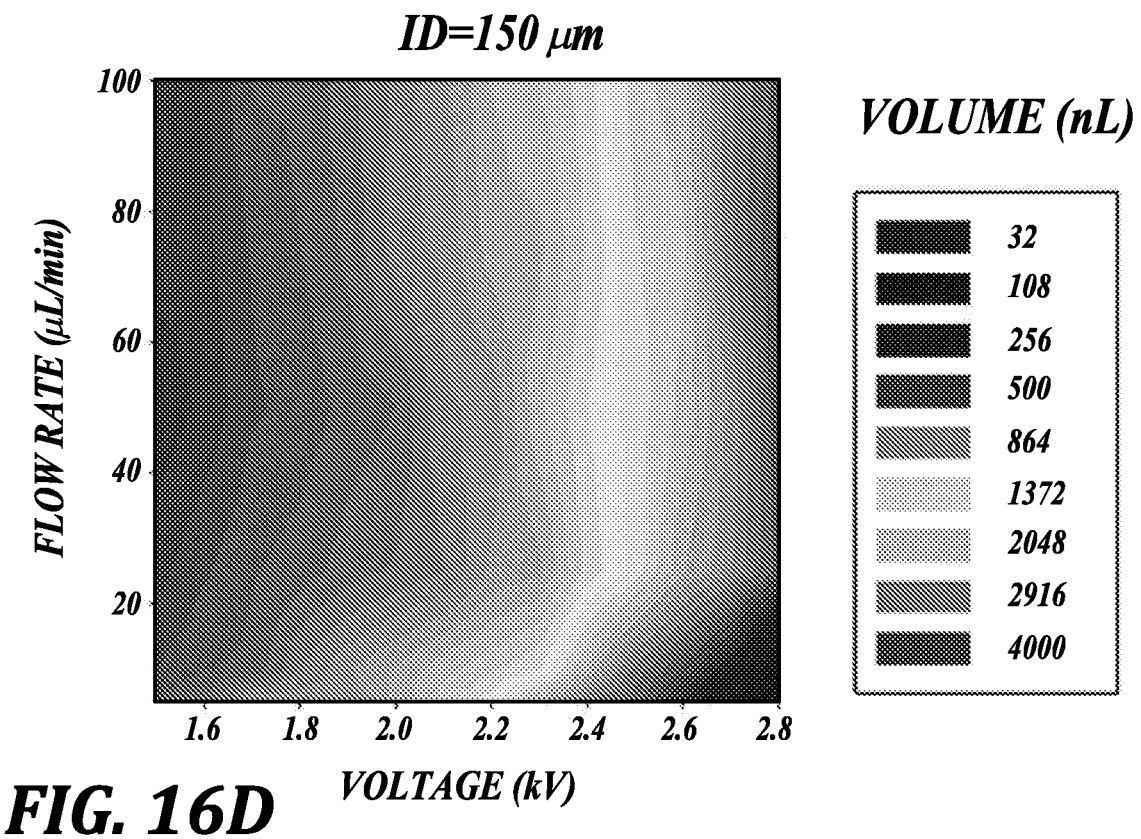

As discussed above, different voltages may be applied to various portions of the device, such as with a power source of the device, to eject droplets from the capillary. Referring still to FIG. 14, various voltages, V1-V4, are shown applied to the electrode conductively coupled to the second end of the capillary, a first portion of the electrically conductive plate facing toward the second end of the capillary, a second portion of the electrically conductive plate facing away from the second end of the capillary, and the multi-well plate. By applying different voltages to physically separate portions of the device, the device is configured to eject a droplet, shown here to encapsulate a cell, from the capillary for receipt by a multi-well plate.

As discussed further herein with respect to EXAMPLE 7, in order to coordinate droplet ejection for cell sorting, a droplet ejection rate, droplet travel time between the second end of the capillary and a well of the multi-well plate, and a rate at which the moveable stage moves may be considered. In an embodiment, a droplet ejection rate and transit time between the second end of the capillary is coordinated with movement of the moveable stage.

The devices of the present disclosure are configured to emit droplets at a variety of rates, such as in a range of about 1 Hz to about 10 kHz. In an embodiment, the device is configured to eject droplets at a rate in a range of about 5 Hz to about 1 kHz. In an embodiment, the device is configured to eject droplets at a rate in a range of about 5 Hz to about 100 Hz. In an embodiment, the device is configured to eject droplets at a rate in a range of about 10 Hz to about 20 Hz.

A transit time of an ejected droplet can vary based upon, for example, an ejected droplet velocity and a distance between the second end of the capillary and the moveable stage. FIGS. 12A-12G illustrate an example droplet transit between the capillary and a multi-well plate. In the illustrated example, the time is calculated to be around 75 ms for a droplet to be collected in 96-wellplate. For the sake of viewing, a larger droplet was generated by applying a lower high voltage of 1.0 kV. The collection time for a smaller droplet generated by 1.4 kV is shorter than the larger droplets generated by 1.0 kV.

Figure 10B:
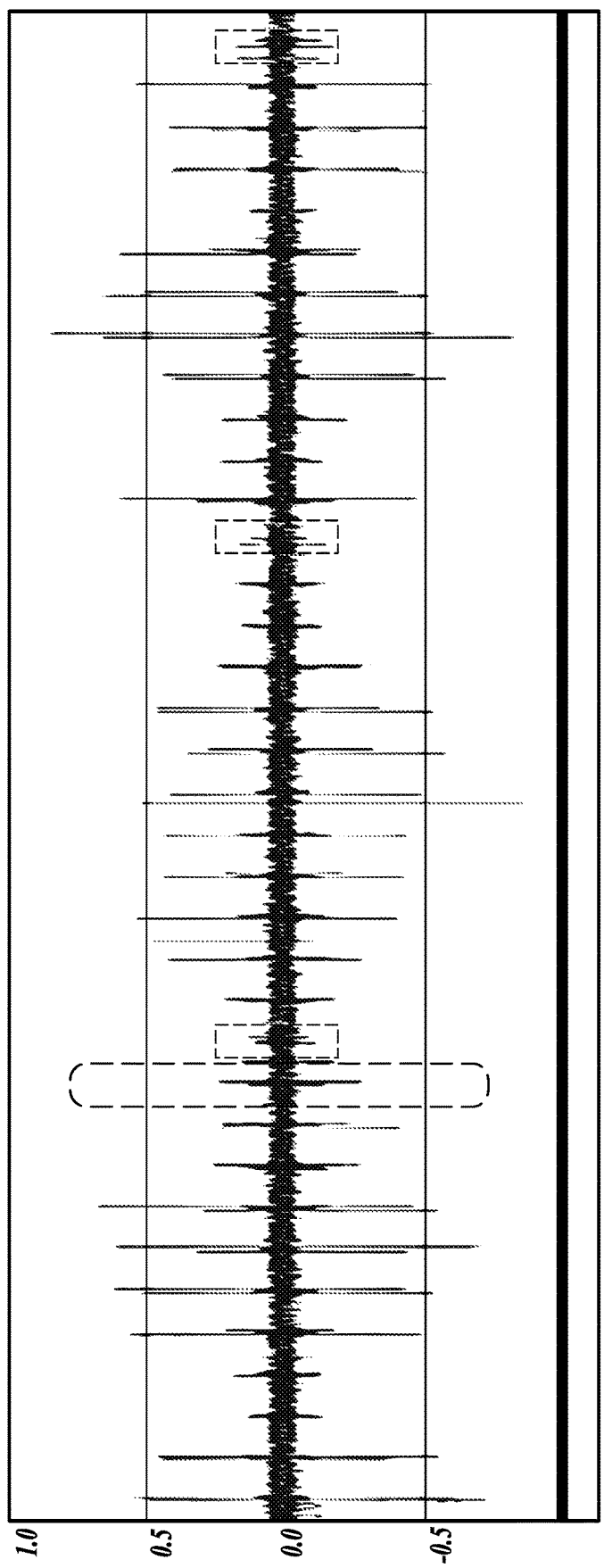
FIGS. 10B-10D are images of recorded sound of a stage moving relative to a second end of a capillary, in accordance with an embodiment of the disclosure, where
Figure 10C:
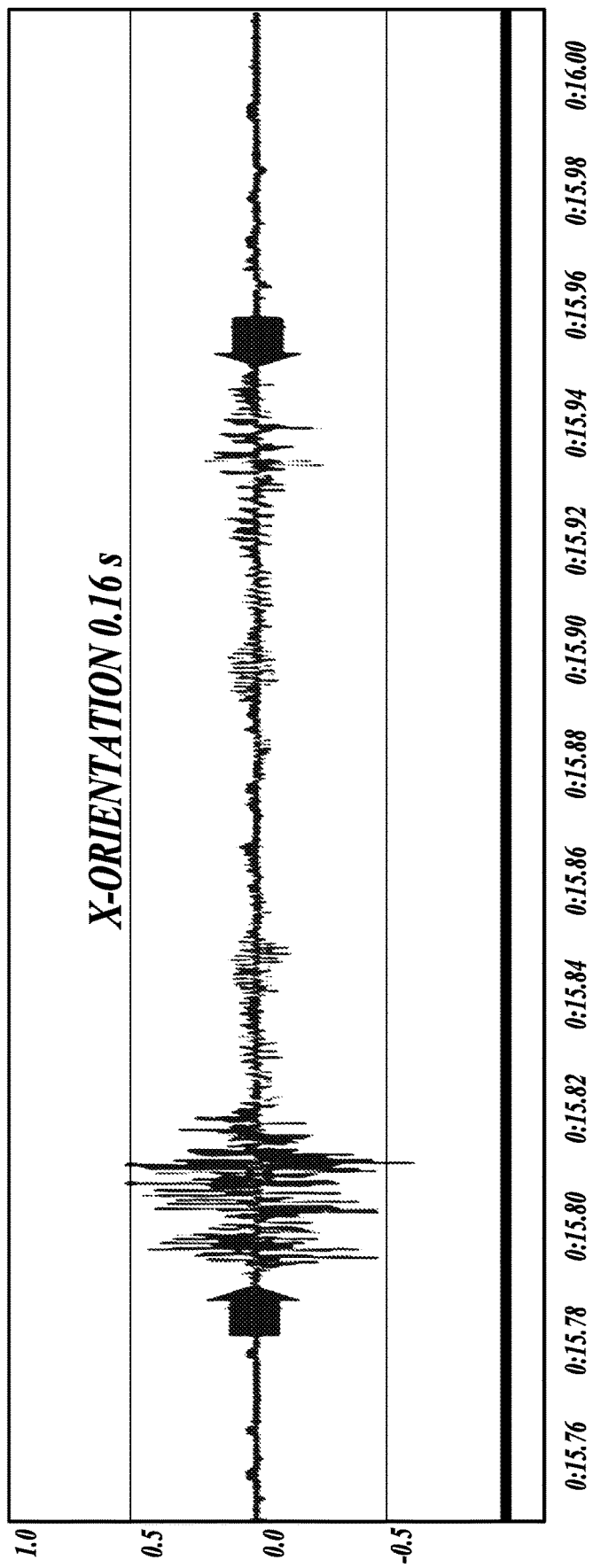
Figure 10D:
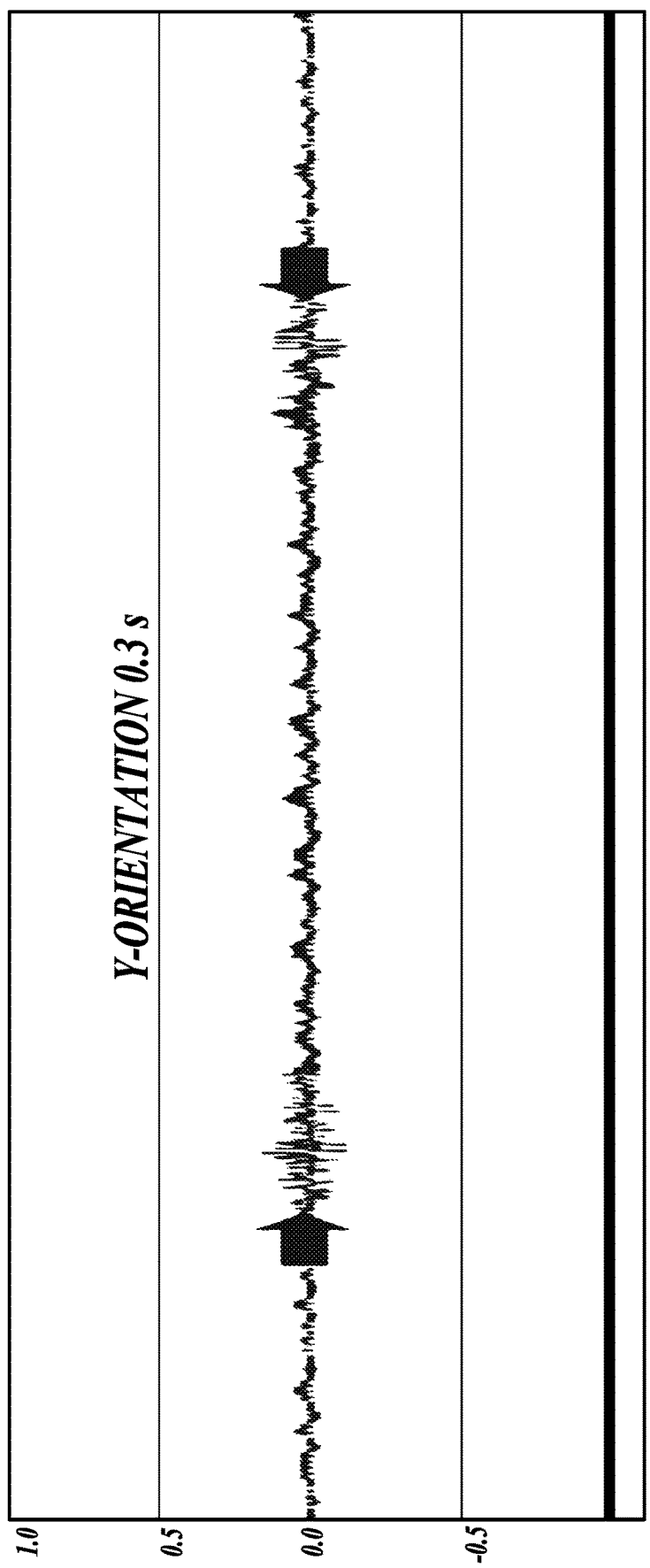
Figure 11A:
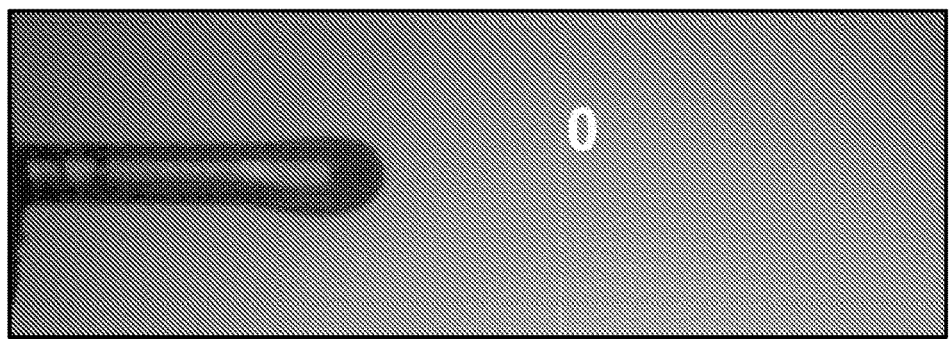
FIGS. 11A-11D are a series images showing the generation of an oil droplet from a capillary of a device, in accordance with an embodiment of the disclosure, with an applied voltage of 1.0 kV, where the time for a droplet to be generated is around 67 ms.
Figure 11B:
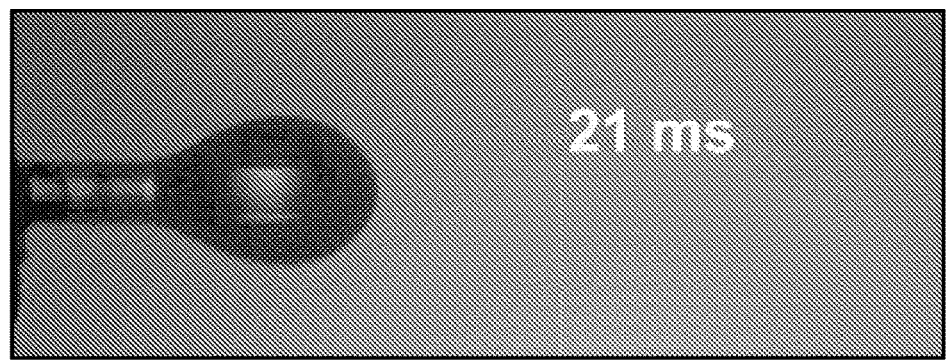
Figure 11C:
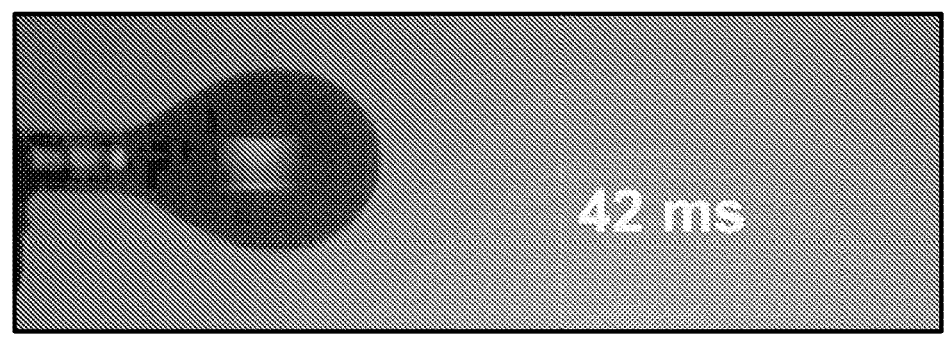
Figure 11D:
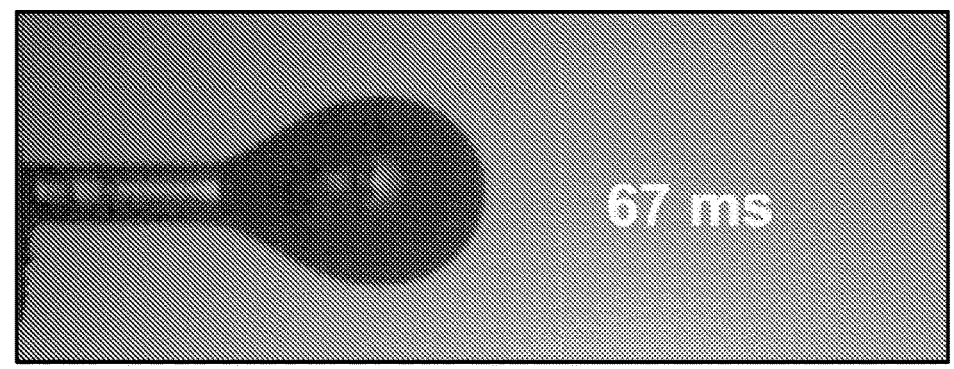
Figures 12A, 12B, 12C, 12D, 12E, 12F, 12G:
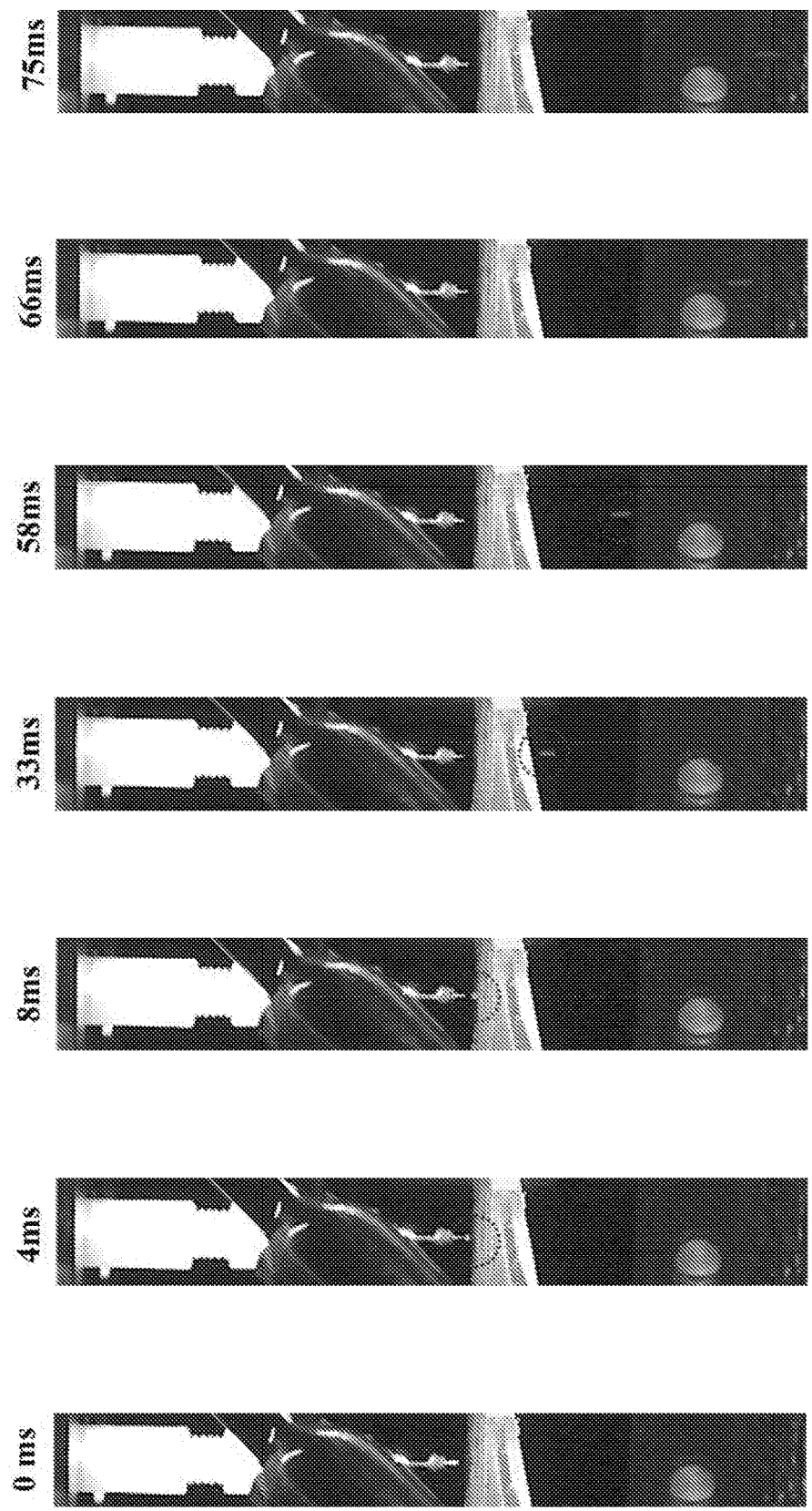
FIGS. 12A-12G are a series images showing an oil droplet falling down from an end of a capillary of a device, in accordance with an embodiment of the disclosure.

FIGS. 10B-10D are images of recorded sound of the moveable stage moving relative to the second end of the capillary. The recorded sound images illustrate example times of moving the stage from a first position to a second position. As discussed further herein with respect to EXAMPLE 7, such movement, for example as illustrated in FIG. 10A, may be coordinated with droplet ejection rates and droplet transit times to coordinate droplet sorting into various wells of the multi-well plate carried by the moveable stage.

Systems

In another aspect, the present disclosure provides systems for generating droplets. In an embodiment, the systems of the present disclosure include a fluid source and a device for generating a droplet in fluidic communication with the fluid source. In an embodiment, the device for generating a droplet is any device described herein.

In an embodiment, the system includes a fluid source and a device for generating droplets, wherein the device includes an integrated light source and photodetector. In this regard, in an embodiment, the device includes a capillary defining a lumen in fluidic communication with the fluid source, the capillary comprising: a first end coupled to the fluid source; and a second end opposite the first end; an electrode in conductive communication with the second end of the capillary and a power source; a light source positioned to illuminate the lumen of the capillary; a photodetector configured to generate an optical signal in response to light emitted by the light source; and a controller operatively coupled to the power source, the photodetector, and the light source, the controller including logic that when executed by the controller, causes the device to perform operations including: detecting the light from within the lumen based on the electrical signal from the photodetector; and applying, with the power source, a voltage to the electrode sufficient to eject a droplet from the second end of the capillary.

In an embodiment, the system includes a device configured to operate based at least in part on a user input. Accordingly, in an embodiment, the system includes a fluid source; and a device comprising: a capillary defining a lumen, the capillary comprising: a first end coupled to the fluid source; and a second end opposite the first end, wherein a viewing portion of the lumen of the capillary is configured for visual inspection by a user; an electrode in conductive communication with the second end of the capillary and a power source; a light source positioned to illuminate the lumen of the capillary; and a controller operatively coupled to the power source, the controller including logic that when executed by the controller, causes the device to perform operations including: applying, with the power source, a voltage to the electrode sufficient to eject a droplet from the second end of the capillary, wherein the device is configured to apply the voltage to the electrode based on an input from the user.

Figures 17A, 17B:
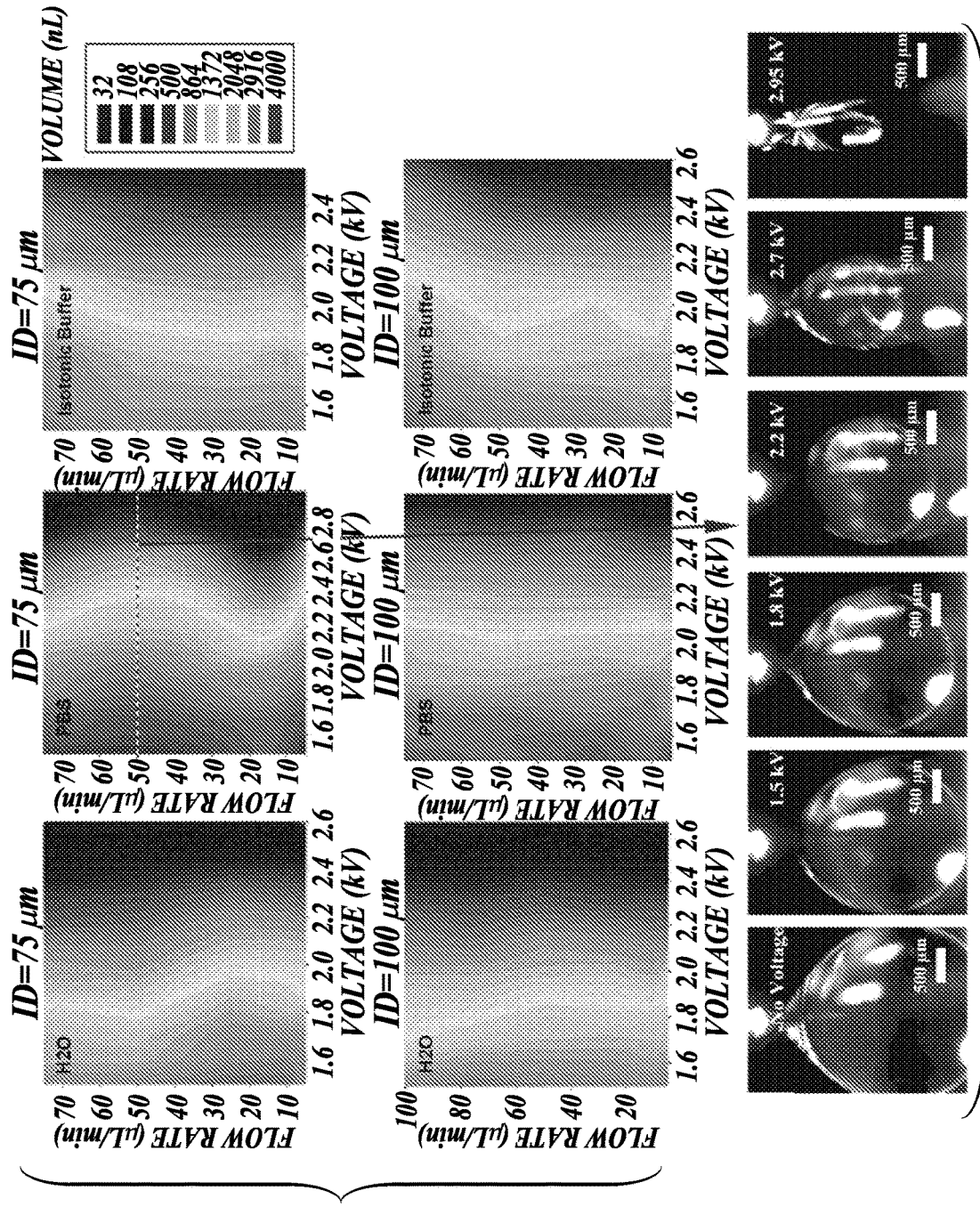
FIG. 17A is a series of graphic illustrations of generated droplets volumes as a function of flow rate, applied voltage at various capillary inner diameters and with various solutions.
FIG. 17B is a series of images of droplets generated under different applied voltages taking along a cross-section shown in FIG. 17A as a dashed line.
Figure 21A:
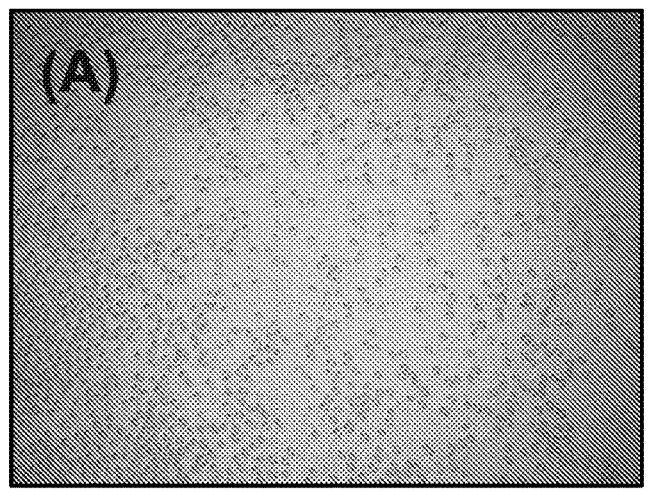
FIGS. 21A-21C are images of k562 cells dyed by trypan blue: (A) before and (B) after dispensing, and (C) after dispensing and then killed with PDA. For the sake of understanding.
Figure 21B:
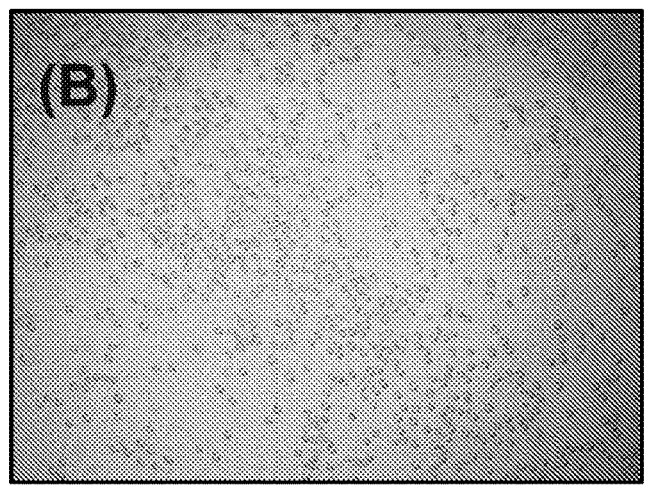
Figure 21C:
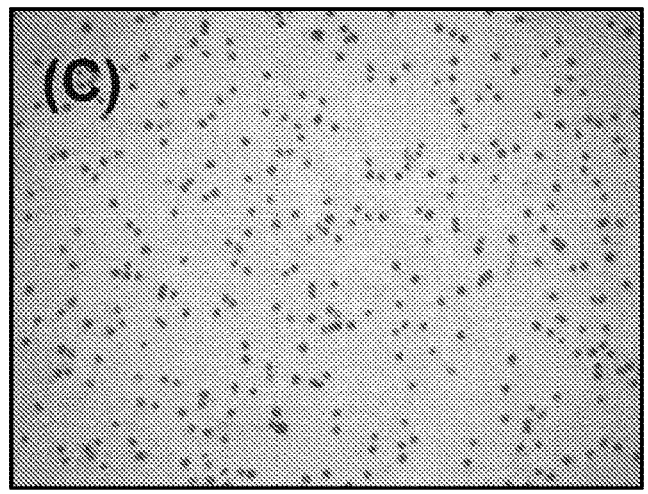

In an embodiment, the fluid source comprises an aqueous liquid. In this regard, the systems may be configured to eject an aqueous droplet from the second end of the capillary as a single emulsion. (See, for example, FIG. 17B). As used herein, a "single emulsion" refers to any combination of two fluids wherein each of the two fluids is immiscible with, but in physical contact with the other fluid. In various embodiments, a single emulsion of droplets can be produced between a liquid and gas phases. In some aspects, the single emulsion comprises an aqueous droplet encapsulated in a gas, such as air.

In an embodiment, the fluid source includes a droplet source, such as a fluid source configured to generate a discrete partition of the first liquid surrounded at least in part by the second liquid. In that regard, attention is directed to FIGS. 3A and 4A, in which systems in accordance with an embodiment of the disclosure is illustrated. As shown, the systems includes a fluid source in fluid communication with a capillary, a light source, shown here as a laser, illumination a lumen of the capillary, a power source in conductive communication with a downstream end of the capillary and a moveable stage, shown here carrying a multi-well plate.

Figure 3A:
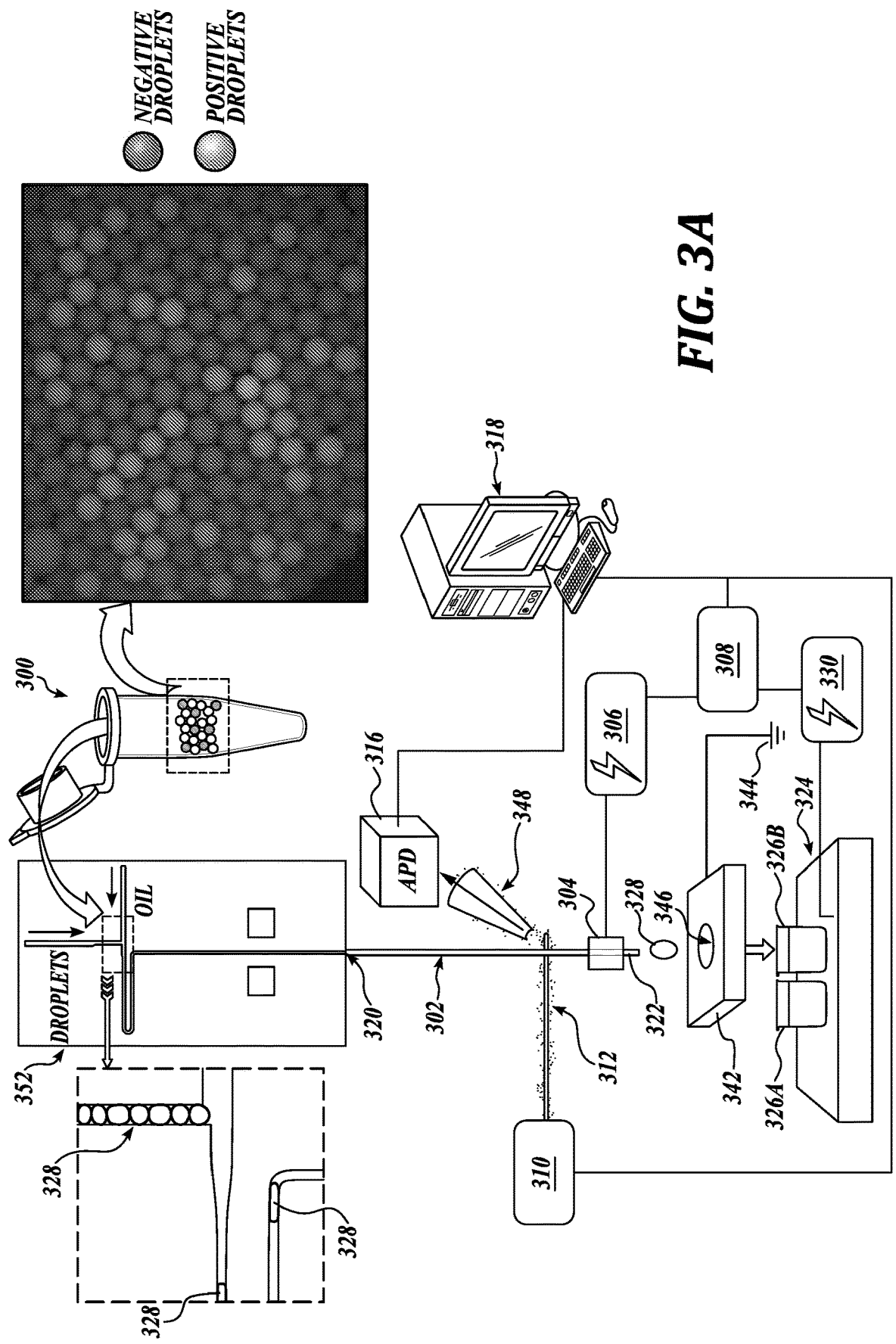
FIG. 3A is a schematic illustration of a system, in accordance with an embodiment of the disclosure, for single-droplet sorting including an inset micrograph (left) of droplets separated by an oil and an inset image (right) of polymerase chain reaction- (PCR) positive and PCR-negative droplets for analysis and sorting by the system.
Figure 4A:
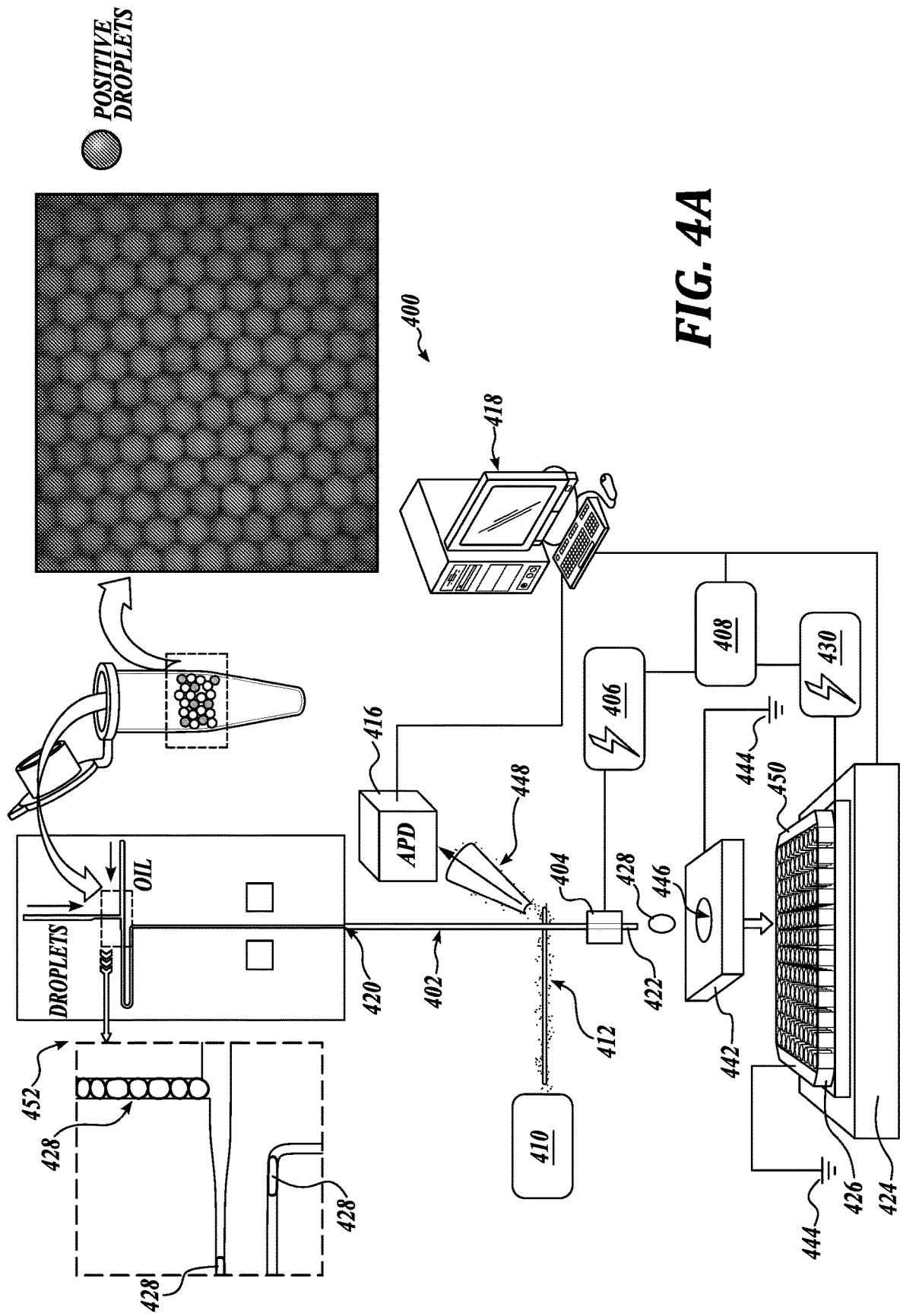
FIG. 4A is a schematic illustration of a system, in accordance with an embodiment of the disclosure.
Figure 4B:
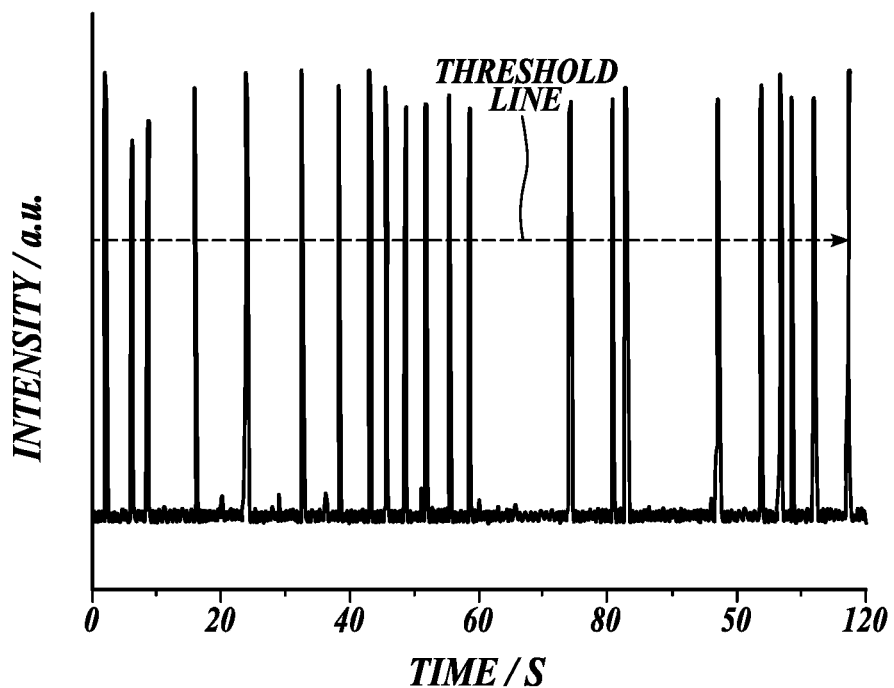
FIG. 4B is a segment of an APD trace from PCR-positive emulsion droplets showing the PCR amplification results of Flt3 gene in single K562 cell (A threshold fluorescence intensity, shown as a dashed line, was set to trigger the dispensing events)

The devices of both FIGS. 3A and 4A are shown to include a droplet source in fluidic communication with the capillary. As shown the droplets are configured to travel through the capillary and, with the application of a voltage to the second of the capillary, eject from the second end of the capillary.

In an embodiment, the fluid source comprises: a first fluidic channel comprising: a proximal end in fluidic communication with a first liquid; and a distal end in fluidic communication with the capillary; and a second fluidic channel in fluidic communication with the first fluidic channel and with a second liquid immiscible with the first liquid. Such a fluid source may be configured to generate a discrete partition. As used herein, a "discrete partition" of a first liquid is similar to a droplet in that it is surrounded by, and encapsulated in, substances other than the first liquid. However, a discrete partition is not necessarily spherical in shape and is not necessarily surrounded entirely by one other substance. For example in some aspects, a discrete partition of a first liquid is surrounded in part by a second liquid and in part by walls of a fluidic channel. In some aspects, discrete partitions are referred to herein as "plugs" and/or "compartments." (See, for example, FIGS. 7A-7G).

In an embodiment, the first liquid includes a component selected from the group consisting of buffer solutions, cerebrospinal fluid or artificial cerebrospinal fluid, blood samples, plasma samples, serum samples, solutions that contain cell lysates or secretions or bacterial lysates or secretions, and other biological samples containing proteins, bacteria, viral particles and/or cells (eukaryotic, prokaryotic, or particles thereof) among others.

In an embodiment, the first liquid includes one or more cells. In an embodiment, cells expressing a malignant phenotype, fetal cells, circulating endothelial cells, tumor cells, cells infected with a virus, cells transfected with a gene of interest, or T-cells or B-cells present in the peripheral blood of subjects afflicted with autoimmune or autoreactive disorders, or other subtypes of immune cells, or rare cells or biological particles (e.g., exosomes, mitochondria) that circulate in peripheral blood or in the lymphatic system or spinal fluids or other body fluids. The cells or biological particles can, in some circumstances, be rare in a sample and the discretization can be used, for example, to spatially isolate the cells, thereby allowing for detection of the rare cells or biological particles.

In an embodiment, the first liquid comprises an analyte to be analyzed. The analyte may comprise, without limitation, a small molecule, a drug, a toxin, a carbohydrate, a sugar, a lipid, a fatty acid, a metabolite, a polynucleotide such as DNA or RNA, an amino acid, a peptide, a polypeptide such as a protein (e.g., an antibody, a glycoprotein or an avidin protein), a cell such as a prokaryotic cell or a eukaryotic cell, a cell lysate, a cellular fraction or organelle, a biological or synthetic vesicle such as liposome, a virus or viral particle, a polymer or any combination thereof.

In an embodiment, the second liquid, which is immiscible with the first liquid, is an oil, but it does not need to be an oil. Potential liquids that can serve as the second liquid include but are not limited to, fluorocarbon based oils, silicon compound based oils, hydrocarbon based oils such as mineral oil and hexadecane, vegetable based oils, ionic liquids, an aqueous liquid that is immiscible with the first liquid, or that forms a physical barrier with the first liquid.

In an embodiment, the second liquid comprises a hydrocarbon-based liquid, a fluorocarbon-based liquid, a silicone-based liquid, or a combination thereof. In some aspects, the second liquid comprises a mineral oil, a vegetable oil, a silicone oil, a fluorinated oil, a fluorinated alcohol, a Fluorinert, a Tegosoft, a perfluorinated ester, a perfluorinated ether or a combination thereof. In some aspects, the second liquid comprises perfluorohexane, perfluorodecalin, hexadecane or a combination thereof.

In an embodiment, the first liquid and/or the second liquid can comprise a fluid interface modification. Fluid interface modification elements include interface stabilizing or modifying molecules such as, but not limited to, surfactants, lipids, phospholipids, glycolipids, proteins, peptides, nanoparticles, polymers, precipitants, microparticles, or other components. In an embodiment, one or more fluid interface modification elements can be present in a fluid that will be comprised in an inner droplet. In an embodiment, one or more fluid interface modification elements can be present in a fluid that will be comprised in an outer droplet. The fluid interface modification elements present in a fluid that will be comprised in one phase of the emulsion can be the same or different from the fluid interface modification elements present in a fluid that will be comprised in another phase of the emulsion.

In an embodiment, of the present disclosure, the fluid interface modification element can be used to prevent coalescence of neighboring emulsion droplets, leading to long-term emulsion stability. In some aspects, fluid interface modification elements can have some other or additional important role, such as providing a biocompatible surface within droplets, which may or may not also contribute to emulsion stability. In some aspects, the components can play a role in controlling transport of components between the fluids or between droplets. In some aspects, surfactants can be included to, e.g., improve stability of the droplets and/or to facilitate droplet formation.

Suitable surfactants can include, but are not limited to, non-ionic surfactants, ionic surfactants, silicone-based surfactants, fluorinated surfactants or a combination thereof. Non-ionic surfactants can include, for example, sorbitan monostearate (Span 60), octylphenoxyethoxyethanol (Triton X-100), polyoxyethylenesorbitan monooleate (Tween 80) and sorbitan monooleate (Span 80). Silicone-based surfactants can include, for example, ABIL WE 09 surfactant. Other types of surfactants generally well known in the art can similarly be used. Additional examples of fluid interface modification elements include without limitation ABIL EM90, TEGOSOFT DEC, bovine serum albumin, sorbitans, polysorbates (e.g., PEG-ylated sorbitan such as TWEEN 20), sodium dodecylsulfate, 1H,1H,2H,2H-perfluorooctanol, monolein, oleic acid, phospholipids, and Pico-Surf, among others.

In an embodiment, the surfactant can be present at a variety of concentrations or ranges of concentrations, such as approximately 0.01%, 0.1%, 0.25%, 0.5%, 1%, 5%, or 10% by weight.

Figure 8B:
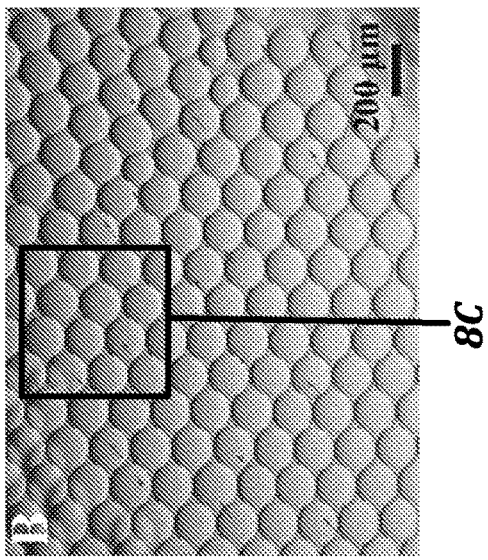
FIG. 8B is an optical micrograph of droplets, in accordance with an embodiment of the disclosure, generated by the flow channel of FIG. 8A, where the arrows indicate a single cell in a droplet.
Figure 8C:
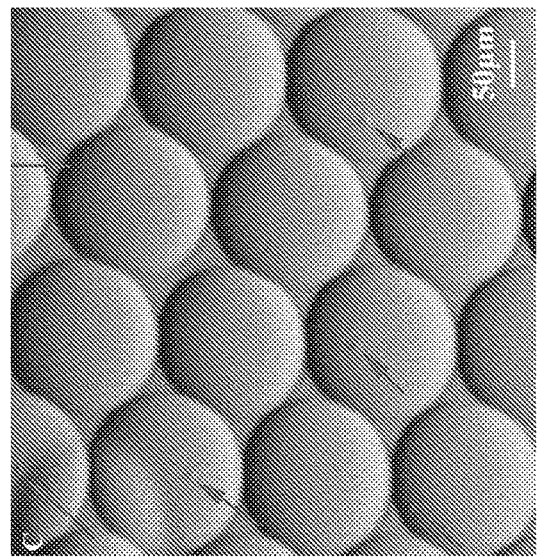
FIG. 8C is a magnified image of the squared region in FIG. 8B.
Figure 8A:
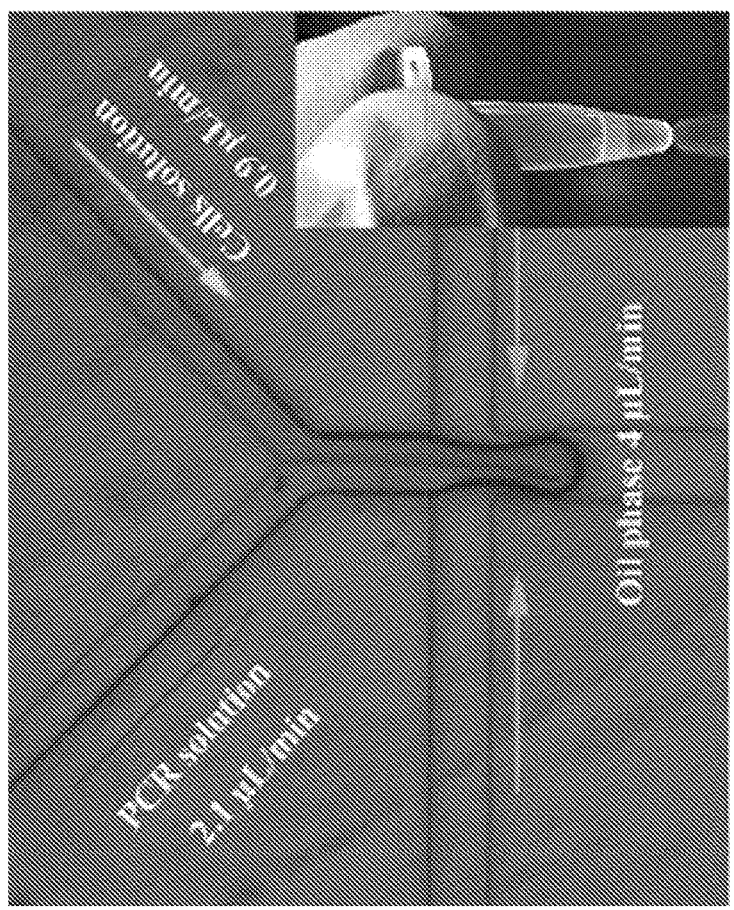
FIG. 8A is a microscope image of a flow channel to encapsulate a single cell and PCR reagents into emulsion droplets for downstream PCR analysis, in accordance with an embodiment of the disclosure (inset is a picture of generated emulsion droplets collected in an Eppendorf tube)

Attention is directed to FIGS. 8A-8C, in which fluid sources in accordance with an embodiment of the disclosure are illustrated. As shown, the fluid source includes a first fluidic channel flowing a first liquid including cells in solution and a second fluidic channel in fluidic communication with the first fluidic channel and flowing a second liquid, shown here as an oil, immiscible with the first liquid. In the illustrated embodiment, flow of the second liquid generates a droplet or discrete partition within a downstream portion of the first fluidic channel, wherein the droplet includes aqueous liquid from the first fluidic channel.

In the illustrated embodiment, the fluid source includes a third fluidic channel in fluid communication with the first fluidic channel and a third liquid comprising reagents reactive with a component of the first liquid. Such reagents may react with components of the first liquid, which may be analyzed downstream, such as in a multi-well plate into which droplets containing discrete partitions of the first and third liquids and the second liquid are dispensed and sorted.

In an embodiment, the reagents include reagents configured to perform a nucleic acid amplification reaction. Such reagents can include, for example, PCR and RT-PCR solutions, isothermal amplification solutions, such as for LAMP or NASBA, and the like. As shown, the third liquid includes a polymerase chain reaction (PCR) solution, including reagents suitable to perform a PCR reaction with components of the first liquid. In an embodiment, the PCR solution is configured to amplify nucleic acid of the cells in the cell suspension. In this regard, droplets ejected from the second end of the capillary can include amplified nucleic acid of a cell disposed in the droplet. Such amplified nucleic acid can be analyzed downstream to interrogate, for example, nucleic acids expressed by the cell in the ejected droplet.

In an embodiment, the reagents include a reagent configured to bind with a component of the first liquid, such as a cell, a portion of a cell, a biological particle, and amplified nucleic acid. Further, such binding reagent may be configured to generate a signal, such as a fluorescent light signal, in response to absorbing light, such as light from the light source.

As above, in an embodiment, the first liquid can include a suspension of cells. FIGS. 8B and 8C illustrate droplets generated by the fluid source illustrated in FIG. 8A. As indicated with arrows, some of the droplets carry a cell from the cell suspension of the first liquid.

In an embodiment, the systems of the present disclosure are configured to eject a droplet containing a single cell. As discussed further herein, analysis of a single cell, such as analysis molecules secreted by the cell, may be performed by isolating such a single cell in a droplet, such as in a double emulsion droplet.

FIGS. 20A and 20B illustrate a chance of a droplet ejected by a system, in accordance with an embodiment of the disclosure, containing more than one cell for different numbers of sorted cells and different droplet volumes. As shown by increasing a volume of droplets ejected by the system the chance of an ejected droplet including more than one cell increases. Accordingly, in certain embodiments, it may be advantageous to adjust the operating parameters of the system, as discussed further herein with respect to FIGS. 18A-18E and 19A-19C, to eject droplets of smaller sizes, such as in a range of about 0.1 µl to about 1 µl.

As discussed further herein, the device of the present disclosure may be configured to sort droplets ejected by the device based on contents of the droplet. In an embodiment, the device is configured to move the stage relative to the second end of the capillary based upon electrical signals, such as electrical signals generated by one or more photodetectors.

As discussed further herein with respect to FIGS. 3A-3D, the systems of the present disclosure are suitable to sort, for example, double emulsion droplets based on the presence or absence of amplified nucleic acid disposed within an aqueous core of the double emulsion droplets. Likewise, as discussed further herein with respect to FIGS. 4A-4C, the systems of the present disclosure are suitable to sort, for example, double emulsions into wells of a 96-well plate based on the presence or absence of a cell in an aqueous core of the double emulsions.

Methods

In another aspect, the present disclosure provides a method of producing a droplet. In an embodiment, the method includes flowing a fluid through a capillary; emitting light from a light source into a lumen of the capillary; and applying, with a power source, a voltage to an electrode conductively coupled to a distal end of the capillary to eject a droplet from the distal end of the capillary. In an embodiment, the methods of the present disclosure can be performed using a device and/or a system described herein.

In an embodiment, the method further includes generating, with a photodetector, an electrical signal in response to light from within the lumen. As discussed further herein, such light from within the lumen can be scattered light scattered off of a scattering source, such as a cell, in the lumen of the capillary. In that regard, the electrical signal may be based upon the scattered light. As also discussed further herein, in an embodiment, the light is fluorescent light emitted from within the lumen of the capillary, such as fluorescent light emitted by a fluorophore excited by the light from the light source. In that regard, the electrical signal may be based upon fluorescent light.

In an embodiment, the method includes generating two or more electrical signals in response to light from within the lumen. As discussed further herein, in an embodiment, the electrical signals are generated by two or more photodetectors, such as where one photodetector absorbs scattered light from within the capillary and another photodetector absorbs fluorescent light from within the lumen of the capillary. In an embodiment, the method includes generating two, three, four, or more electrical signals based upon fluorescent light of different wavelength ranges. In that regard, such multiple electrical signals based upon fluorescent light absorbed by multiple photodetectors configured to generate different respective electrical signals based on fluorescent light having different wavelength ranges.

In an embodiment, a viewing portion of the capillary is configured to be viewed by a user. In that regard, a user may view contents of the lumen of the capillary, such as with the naked eye or through magnifying optics, such as a microscope. In an embodiment, timing of applying the voltage is based upon a user input, such as a user input based upon interrogation of the contents of the lumen. In that regard, a user can inspect the lumen and apply voltage to the capillary to eject a droplet from the capillary by generating a user input.

As above, a voltage is applied to an electrode conductively coupled to a distal end of the capillary to eject a droplet therefrom. In an embodiment, such a voltage is applied constantly to eject, for example, a steady stream of droplets from the capillary. In an embodiment, the voltage is applied periodically, such as based one or more electrical signals from one or more photodetectors or based on a user input. Accordingly, in an embodiment, timing of applying the voltage is based on an electrical signal. In another embodiment, timing of applying the voltage to the electrode is based on an input from a user.

In an embodiment, the method includes moving, with a source of motion, a stage relative to the distal end of the capillary. In an embodiment, the stage carries a multi-well plate comprising two or more wells such that the droplet is received by one of the two or more wells. In an embodiment, moving the stage is based upon an electrical signal, such as an electrical signal from a photodetector. In an embodiment, moving the stage is based upon a user input. As discussed further herein, such stage movement based upon electrical signals and/or user inputs can form the basis of sorting droplets ejected from the capillary.

In an embodiment, the method further includes moving the stage with the source of motion relative to the second end of the capillary such that a second droplet ejected from the distal end of the capillary is received by another of the two or more wells. In an embodiment, the second droplet is ejected from the capillary and received by another of the two or more wells of the multi-well plate when, for example, a second electrical signal, based on contents of the lumen of the capillary, is below a threshold. As discussed further herein, such a second electrical signal may be based upon contents of the capillary lumen that later comprise the second droplet. In that regard, the second droplet may be separated from the first droplet, for example, when the second droplet does not contain an analyte of interest.

In an embodiment, flowing the fluid through the capillary comprises flowing a plurality of discrete partitions comprising a first liquid at least partially surrounded by a second liquid immiscible with the first liquid through the capillary, as discussed further herein with respect to, for example, FIGS. 3A, 4A, 7A-7G. Accordingly, in an embodiment, the droplet ejected from the capillary comprises double emulsion comprising the first liquid and the second liquid, as discussed further herein with respect to FIGS. 2A-2I.

As above, in an embodiment, the fluid includes one or more analytes of interest. In an embodiment, the fluid includes one or more cell, one or more portions of cells, one or more biological particles, and the like. Accordingly, in an embodiment, the droplet ejected by the capillary comprises one or more cells, one or more portions of cells, one or more biological particles, and the like. In an embodiment, the droplet is a double emulsion, wherein an aqueous core of the double emulsion carries a cell, a portion of a cell, a biological particle, and the like. In an embodiment, the portion of the cell is selected from the group consisting of an organelle, a vesicle, a virus, a bacterium, an organoid, and a spheroid. As discussed further herein with respect to FIGS. 20A-20C, in an embodiment, the droplet carries a single cell, a single portion of a cell, a single biological particle, or the like. This is in contrast to a droplet carrying, for example, two or more cells. As discussed further herein, by isolating a single cell in a droplet, such as a double emulsion droplet, and individually sorting such a droplet into a well of a multi-well plate, the contents of the cell can be analyzed, amplified, and the like in isolation from other cells. In an embodiment, nucleic acids disposed in the droplet are amplified. Such nucleic acid amplification may be performed prior to ejection from the capillary, such as upstream of the second end of the capillary. Such nucleic acid amplification may be performed prior to introducing the droplets into the capillary, such as in a separate container or eppendorf tube, prior to their introduction into the capillary. In an embodiment, nucleic acid amplification is performed on the contents of a single lysed cell. In an embodiment, nucleic acid amplification is performed on the contents of a small group of cells, such as a group of cells selected based on one or more properties of the cells in the group of cells.

In an embodiment, the fluid flowing through the capillary includes a reagent. In an embodiment, such a reagent is reactive with one or more cells, one or more portions of cells, one or more biological particles, and the like disposed in the fluid. In that regard, the reagent is configured to react with such contents of the fluid, the products of which may be analyzed downstream, such as in a multi-well plate into which the droplets are ejected.

In an embodiment, the reagent includes a reagent for a nucleic acid amplification reaction. In this regard, the reagents may be configured to generate amplified nucleic acid based on nucleic acid of, for example, a cell in a droplet ejected by the capillary. Accordingly, in an embodiment, a droplet ejected from the capillary includes amplified nucleic acid of a cell.

EXAMPLES

Example 1

Materials

QX200™ Droplet Generation Oil and SsoAdvanced Universal Probes Supermix were purchased from Bio-Rad (Hercules, CA). DNA primers were purchased from Integrated DNA Technologies (Coralville, IA). Bovine serum albumin (BSA) was purchased from Roche Diagnostics (Risch-Rotkreuz, Switzerland). EvaGreen was purchased from Biotium (Fremont, CA). Nuclease-free water was purchased from Thermo Fischer Scientific (Waltham, MA). Polydimethylsiloxane (PDMS) and catalyst agent were purchased from Dow Corning (Midland, MI). SU-8 2050 Epoxy Negative Photoresist was purchased from MicroChem (Westborough, MA). Trichloro(1H,1H,2H,2H-perfluorooctyl) silane (97%) was purchased from Sigma-Aldrich (St. Louis, MO). High voltage power supplies were purchased from Bertan High Voltage (Hicksville, NY). A 488 nm laser with a CDRH LP 1041441 AG power supply was purchased from Coherent (Santa Clara, CA). APDs (SPCM-AQRH-11-FC) were purchased from Excelitas Technologies (Waltham, MA). The CFX96 Real-Time PCR Detection system was purchased from Bio-Rad. FM 1-43 dye was purchased from Thermo Fisher Scientific; 100 µg of dye was diluted with 46 µl of dimethyl sulfoxide (Sigma-Aldrich). The Typhoon FLA 9000 system was purchased from GE Healthcare (Chicago, IL). The GC640 CCD and GX1920 cameras were purchased from Allied Vision Technologies (Burnaby, BC, Canada). 96-well plates were purchased from Bio-Rad. Calbiochem-brand Tween 20 was purchased from Sigma-Aldrich. The AZ 100 Microscope was purchased from Nikon (Tokyo, Japan). A Pump 33 DDS was purchased from Harvard Apparatus (Holliston, MA). The K562 chronic myelogenous leukemia cell line was purchased from American Type Culture Collection (Manassas, VA). Buffer solution was comprised of 8.0% sucrose (Sigma-Aldrich), 0.3% dextrose (Sigma-Aldrich), and 0.1% BSA in 1 mM Tris-buffer pH 8.3 (Sigma-Aldrich). Paraformaldehyde aqueous solution (PDA, 4%, EM grade) was purchased from Electron Microscopy Sciences (Hatfield, PA).

Example 2

Chip Fabrication

Soft lithography was used for PDMS chip fabrication. Briefly, SU-8 2050 Epoxy Negative Photoresist was spin-coated onto a 3-inch silicon wafer to form a film of ~50 µm thickness, measured using an interferometer. 10% (w/w) of catalyst agent was used for PDMS curing. After degassing by vacuum, the samples were cured at 70° C. for 4 h. The PDMS chip was peeled off the master and inlet and outlet holes were punched and exposed to oxygen plasma along with a glass slide substrate. The PDMS channel was then sealed irreversibly against the glass substrate. Finally, the chips were stored in a 115° C. oven for 24 h to change the inner surface of the channels from hydrophilic to hydrophobic.

Example 3

Cell Culture

K562 cells were cultured in RPMI 1640 medium supplemented with 10% FBS and 1% penicillin/streptomycin at 37° C. at 5% $CO_2$. Exponential phase cells were centrifuged at 250 rpm for 5 min and resuspended in buffer twice before experiments.

Example 4

PCR Experiments

On-chip single cell encapsulation was achieved using a flow-focusing method in a T-junction microchannel by injecting cell solution ($4 \times 10^5$/ml) and PCR reagents in two separate channels. A mini stir bar was placed in the syringe to prevent cell aggregation. PCR reagents were prepared by mixing 100 µl of SsoAdvanced Universal Probes Supermix (Bio-Rad), 10 µl of primers, 20 µl of 20× EvaGreen dye (Biotium), and 10 µl of BSA. Droplets were collected off-chip, and single cell PCR amplification was performed in a 96-well plate using 10 μL of the PCR mixture described above in each well, using a CFX96 Real-Time PCR Detection System (Bio-Rad). Amplification was performed using the following conditions: hot start at 95° C. for 4 min, 60 cycles of denaturation at 95° C. for 5 s, and annealing/extension at 60° C. for 45 s.

Example 5

Imaging

An AZ 100 Microscope with a GX1920 camera was used to acquire brightfield and fluorescence images of cells and droplets. A high-speed GC640 CCD camera was used to record the formation of double emulsion droplets and aqueous droplets. Multi-well plate screening experiments were performed using a Typhoon FLA 9000 imaging system. Images were analyzed using ImageJ software (http://rsbweb.nih.gov). Goldwave software (http://www.goldwave.com/) was used to analyse sound data collected during stage movement.

Example 6

Exemplary System Configuration

The automated fluorescence-activated single-droplet dispenser (FIG. 1A) employs a programmable combination of capillary-based fluorescence monitoring, high-voltage-triggered single droplet generation, and a mechanical stage with two-dimensional motion. A fluorescence signal from a droplet is sensed by an avalanche photodiode detector (APD), triggering movement of the mechanical stage to collect the droplet in a multi-well plate. Precise control of the formation of an oil droplet containing one aqueous droplet of interest at the open end of the capillary is the key step in dispensing single droplets and cells into individual wells of a well plate for downstream analysis. To achieve this, we used electrohydrodynamic actuation and applied high voltage to the capillary holder to exert a controllable force on the emulsion droplets, thereby forming a double emulsion (aqueous-in-oil-in-air droplet) for dispensing into the well plate.

Figure 1D:
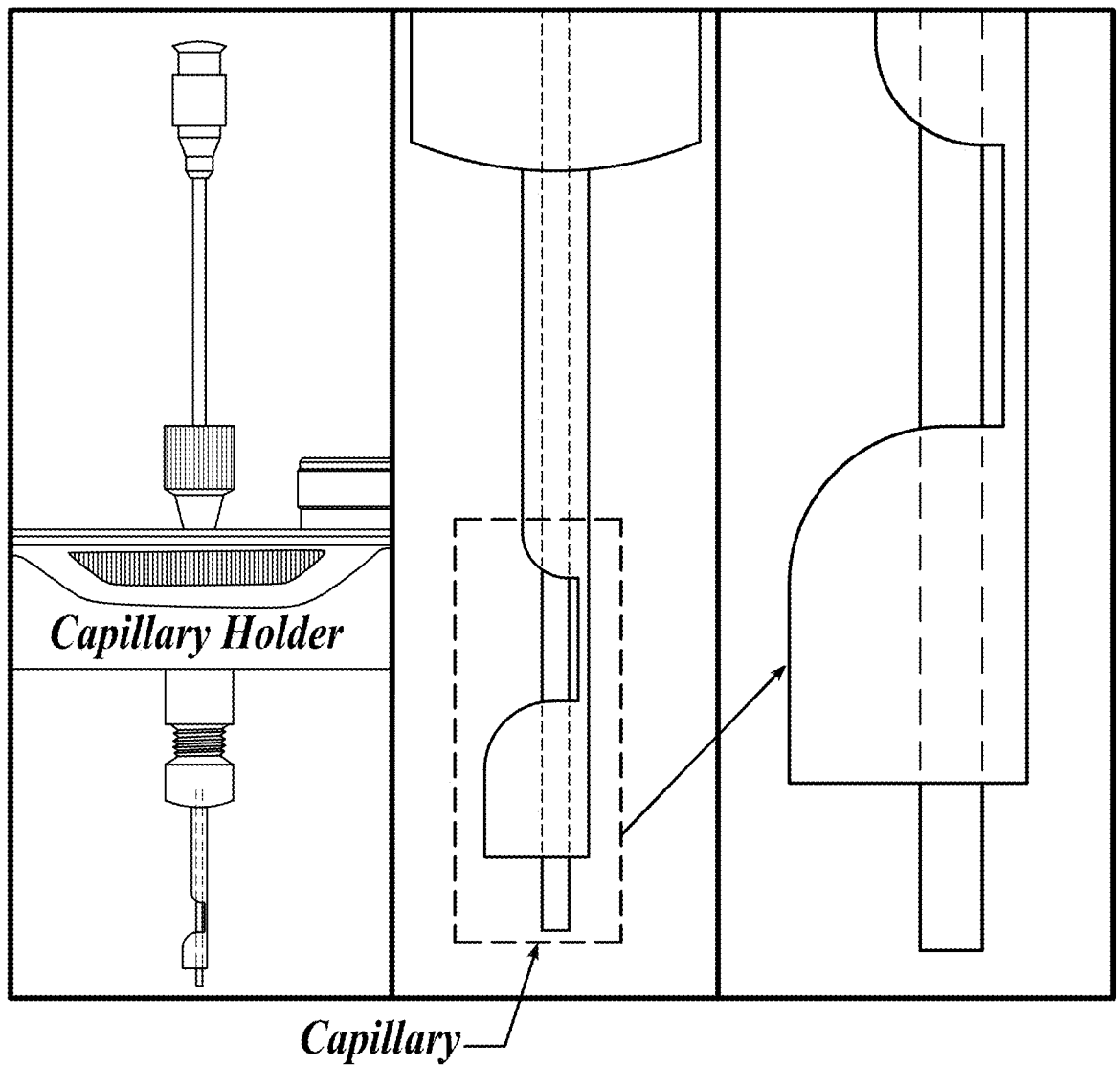
FIG. 1D is a series of images showing details of a capillary holder and a capillary of a device, in accordance with an embodiment of the disclosure.
Figure 2A:
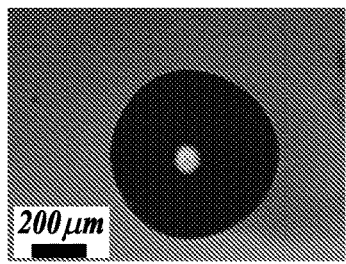
FIGS. 2A-2I are a series micrographs showing the high-voltage controlled formation of oil droplets with different sizes ejected from a capillary of a device, in accordance with an embodiment of the disclosure (scale bar is 200 μm)
Figure 2B:
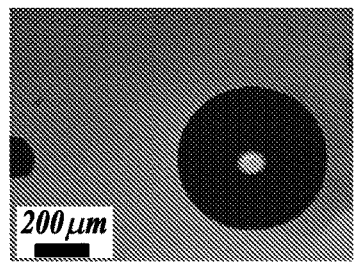
Figure 2C:
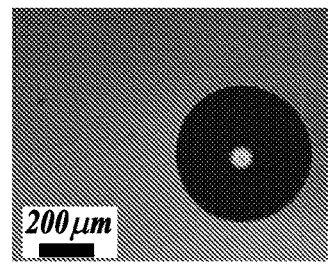
Figure 2D:
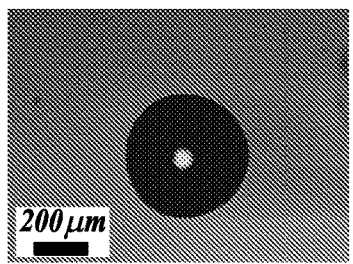
Figure 2E:
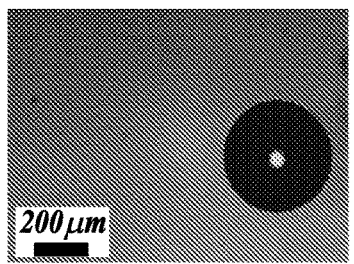
Figure 2F:
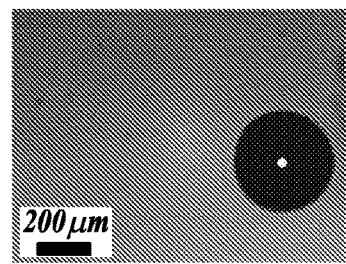
Figure 2G:
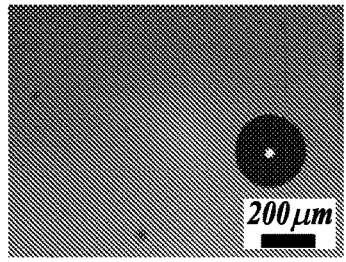
Figure 2H:
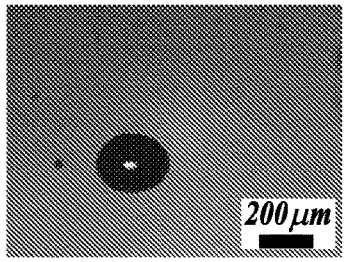
Figure 2I:
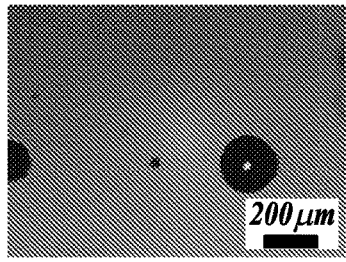

The optical setup of the FASD system (FIG. 1B) is similar to flow cytometry by much simplified. We used a 488 nm laser to excite EvaGreen dye (a DNA Intercalating dye for real-time qPCR fluorescence detection) in experiments to test the system, and two fiber-coupled APDs—one to collect fluorescence and one to collect a light scattering signal. Nanoliter single-droplet precision was achieved using a capillary-based electrohydrodynamic actuation method (FIGS. 1C and 1D). The FASD nozzle consisted of a capillary, a capillary holder made of a modified needle tube, a detection window for laser irradiation, and a copper plate as the ground electrode. The capillary holder was manufactured using commercially available needle tubes of two gauges fixed together using conductive silver paint, which served as the electrode to apply high voltage. The outer tube (N1) was 18 gauge (G), with an inner diameter (ID) of 0.84 mm and an outer diameter (OD) of 1.27 mm; the inner tube (N2) was 22 G, with an ID of 0.41 mm and an OD of 0.71 mm. The purpose of the outer tube in this double layer design was to enlarge the gap between the walls of the capillary and needle tube to minimize the light scatter by the needle tube, and to fix the capillary firmly at the center of the holder. The length of the capillary tip outside the capillary holder (L3 in FIG. 1C) was optimized to obtain the smallest droplets possible without deformation of droplets by the capillary holder. The size of the droplets was affected mainly by the inner and outer capillary diameters, the applied voltage, and the length between the open end of the capillary tip and the electrode (L3). The capillary used for fluorescence-activated single-cell or single-droplet sorting had a circular cross-section with an ID of 0.1 mm and an OD of 0.15 mm. Since a larger L3 caused a larger droplet size, the detection window was positioned on the electrode instead of at the end of the capillary tip to minimize L3.

Application of an electric field to the capillary polarized the oil, resulting in an electric force between the droplets and grounded electrode (copper plate). When the strength of electric field was increased to a certain level, an oil droplet with a specific size was formed and ejected toward the grounded electrode. The process of electric field-controlled droplet formation is shown in FIGS. 6A-6D. FIG. 2 shows a series of images captured using a high-speed camera, illustrating the relationship between droplet size and voltage. Droplet volume was attenuated by increasing the strength of the electric field, demonstrating the use of an electric field to enhance control of droplet formation, which may be useful in other flow-focusing devices.

Example 7

Cell Sorting

To test the capability of the FASD system in droplet microfluidics-based single-cell analysis, we used the system to sort and dispense droplets containing single K562 cells (a myelogenous leukemia cell line), based on the fluorescence signal from a PCR reaction amplifying the FLT3 (FMS-like tyrosine kinase 3) gene. Nucleic acid cytometry is an emerging field built on droplet microfluidics that allows robust identification, sorting and further downstream analysis of cells based on specific nucleic acid biomarkers, which expanded the fluorescent biomarkers from surface to inside of the cell. Since nucleic acids encode the information of life, programming cellular functions, and dictating lots of biological information, identifying cells based on their nucleic acids content is a powerful way to unravel the underlying biology of cells, such as the genetic information of many phenotypes. Existing flow cytometry techniques, however, are unable to reliably recover specific cells based on nucleic acid content. Given the important roles of nucleic acids played in all living things, a tool for dispensing single cell based on nucleic acids is important. Recent developments in nucleic acid cytometry have used barcoding to achieve single-cell resolution, allowing a library of ~$10^9$ droplets to be handled in a single microtube. In contrast, our FASD system takes advantage of the spatial screening possible using two-dimensional microwell arrays, by connecting the voltage-controlled microdrop dispensing nozzle to a well plate.

Figure 3C:
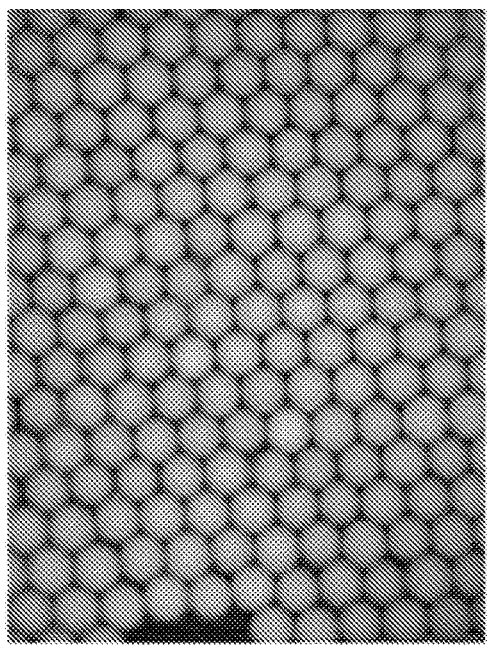
FIGS. 3C and 3D are micrographs of sorted PCR-positive emulsion droplets (C) and PCR-negative droplets (D)
Figure 3D:
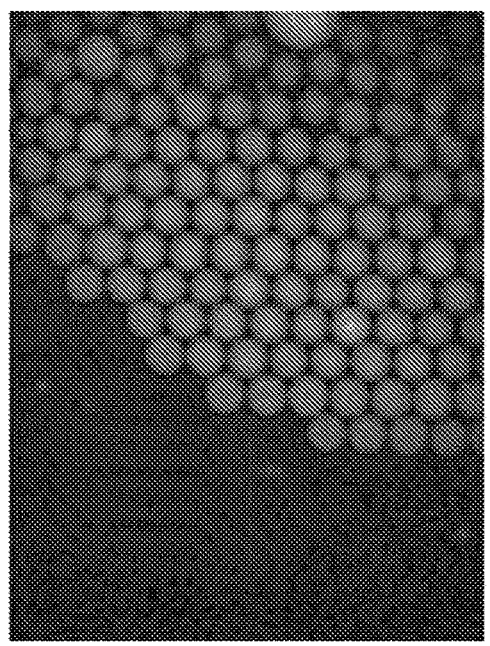
Figure 3B:
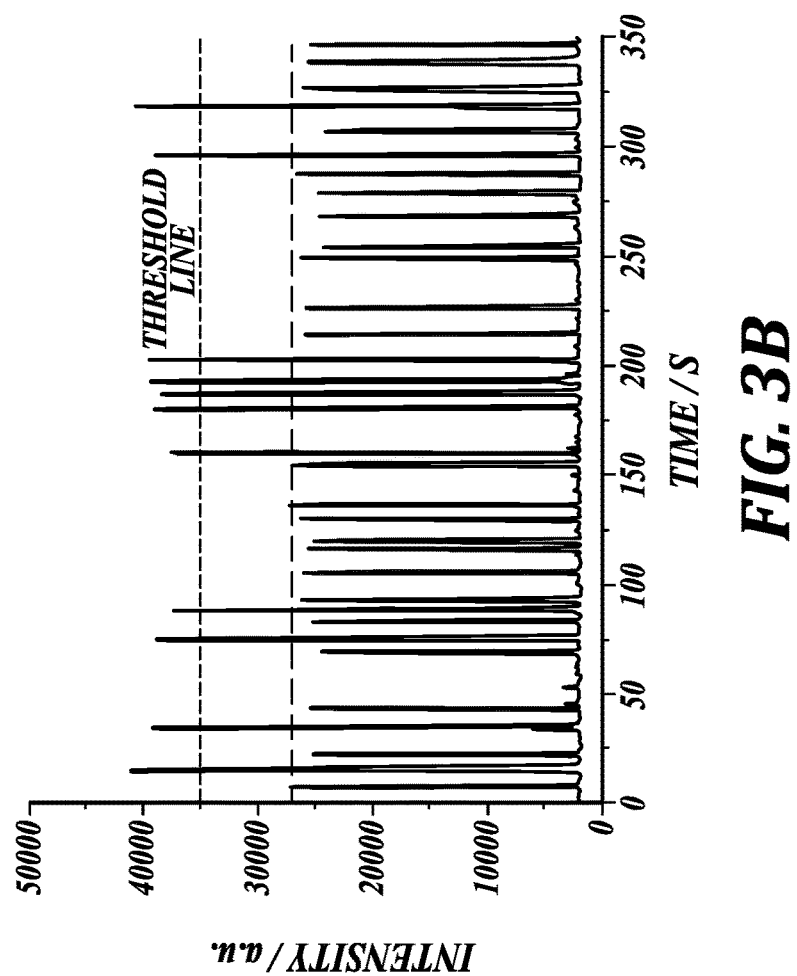
FIG. 3B illustrates a segment of an avalanche photodiode (APD) trace from the emulsion droplets showing the PCR amplification results of Flt3 gene in single K562 cell (A threshold fluorescence intensity, shown as a dashed line, was set to trigger the sorting events)

Surfactant-stabilized droplets containing single cells and PCR reagents were first produced using a flow-focusing T-junction microfluidic device (FIGS. 7A-7G and FIG. 8A), using Bio-Rad Droplet Generation Oil as the continuous phase. The flow rates of the oil and aqueous phases were adjusted to achieve a small and precisely confined droplet volume sufficient to encapsulate a single cell (~2 nL). Emulsion droplets showed a uniform size distribution (FIG. 8B), facilitating subsequent quantitative analysis. Droplets were collected off-chip for PCR amplification and were reinjected into a microfluidic device connected to the FASD system (FIG. 3A). The connected microfluidic device served to introduce additional oil into the emulsion to space out the droplets for subsequent detection and sorting. Two distinct fluorescence intensity clusters for sample droplets were observed, corresponding to PCR-positive and PCR-negative reactions (FIGS. 3A and B). A threshold value was set to trigger movement of the mechanical stage for collection of the PCR-positive and PCR-negative droplets in two separate wells (FIGS. 3C and 3D). A voltage of 1.4 kV was applied to generate an oil droplet with a size sufficient to encapsulate one aqueous droplet. In addition, a negative voltage was applied to an electrode positioned beneath the collection container to guide falling droplets straight toward the center of the container. Cells containing the "keyword" sequence amplified by above PCR-reaction are enriched by the sorting step, discarding unwanted reads from abundant and uninteresting populations, providing far deeper coverage of interesting ones. Isolated PCR-positive droplets were reinjected into the T-junction microfluidic chip and were well separated by the injected oil (FIG. 4A). Movement of the 96-well plate on the 2D mechanical stage was triggered by the fluorescence signal from the droplets, allowing collection of a single droplet in each well (FIGS. 4B and C) of the 96-well plate. The well plate was covered by a grounded metallic board and placed on an electrode connected to negative voltage to shield the electrostatic interaction between the plate and droplets and to achieve successful collection of droplets at the center of each well (FIGS. 9A-9C). The FASD system takes advantage of microtitreplate screening, which is convenient to obtain the results using traditional well-plate imaging platform, such as Typhoon.

Example 8

Droplet Dispensing Frequency

The frequency of single droplet dispensing was determined by the time required to generate and collect a droplet and the response time of the mechanical stage. The response time of the stage, calculated by analyzing the sound of the movement, was 160 ms for a step in the X direction, and 300 ms for a step in the Y direction (FIGS. 10A-10D). The time for droplet manipulation was adjusted to match the response time of the stage. The total time to dispense a droplet was ~850 ms: ~67 ms for droplet generation (FIGS. 11A-11D), ~75 ms for collection (FIGS. 12A-12G), and ~700 ms for transit time (traveling from detection window to the end of the capillary tip). Based on this calculation, the interval time between the detection and trigger events was set to 850 ms to ensure successful collection of the target droplet in a specific well. Single-droplet resolution was achieved by adjusting the flow rate of oil used to separate adjacent aqueous droplets.

While illustrative embodiments have been illustrated and described, it will be appreciated that various changes can be made therein without departing from the spirit and scope of the invention.

The embodiments of the invention in which an exclusive property or privilege is claimed are defined as follows:

1. A device for producing a droplet, the device comprising:
    a capillary defining a lumen, the capillary comprising:
    a first end coupleable to a fluid source; and
    a second end opposite the first end;
    an electrode in conductive communication with the second end of the capillary and a power source, wherein the electrode further comprises a capillary holder configured to carry the capillary and defining an illumination window shaped to expose an illumination portion of the capillary to light, and wherein the capillary holder comprises an outer tube; an inner tube coaxially carried by the outer tube; and a conductive spacer conductively coupling the inner tube and the outer tube;
    a light source positioned to illuminate the illumination portion of the lumen of the capillary through the illumination window;
    a photodetector positioned to absorb light from within the lumen and configured to generate an electrical signal in response to the light from within the lumen; and
    a controller operatively coupled to the power source and the photodetector, the controller including logic that when executed by the controller, causes the device to perform operations including:
    detecting the light from within the lumen based on the electrical signal from the photodetector; and
    applying, with the power source, a voltage to the electrode sufficient to eject a droplet from the second end of the capillary, wherein timing of applying the voltage is based on timing of the electrical signal and whether the electrical signal is above or below a threshold.

2. The device of claim 1, further comprising:
    a stage configured to carry a multi-well plate comprising two or more wells configured to accept the droplet; and
    a source of motion configured to move the stage relative to the second end of the capillary.

3. The device of claim 2, wherein the controller is operatively coupled to the source of motion and the photodetector, the controller further including logic that when executed by the controller, causes the device to perform operations including:
    moving the stage with the source of motion relative to the second end of the capillary based upon whether the electrical signal is above or below the threshold.

4. The device of claim 2, wherein the controller is operatively coupled to the source of motion and the photodetector, the controller further including logic that when executed by the controller, causes the device to perform operations including:
    moving the stage with the source of motion relative to the second end of the capillary such that the second end of the capillary is positioned to eject the droplet for receipt by one of the two or more wells when the electrical signal is at or above a threshold.

5. The device of claim 4, wherein the threshold is a predetermined threshold.

6. The device of claim 2, wherein the controller further includes logic that when executed by the controller, causes the device to perform operations including:
    moving the stage with the source of motion relative to the second end of the capillary such that droplets ejected from the second end of the capillary are individually received by the two or more wells.

7. The device of claim 2, further comprising a multi-well plate cover being electrically conductive and defining two or more apertures configured to allow passage of droplets ejected from the second end of the capillary to the two or more wells of the multi-well plate.

8. The device of claim 7, wherein the multi-well plate cover is conductively coupled to an electrical ground.

9. The device of claim 2, further comprising a second electrode coupled to the power source and disposed on the stage to contact a surface of the multi-well plate when the multi-well plate is carried by the stage.

10. The device of claim 9, wherein the controller is operatively coupled to the second electrode and further includes logic that when executed by the controller, causes the device to perform operations including:

applying a voltage to the second electrode different than the voltage applied to electrode.

11. The device of claim 1, further comprising an electrically conductive plate defining an aperture configured to receive a droplet ejected from the second end of the capillary, wherein the electrically conductive plate is in conductive communication with the power source, or wherein the electrically conductive plate is in conductive communication with an electrical ground.

12. The device of claim 11, wherein the electrically conductive plate is in conductive communication with the power source.

13. The device of claim 11, wherein the electrically conductive plate is in conductive communication with an electrical ground.

14. The device of claim 1, further comprising:
a stage configured to carry a multi-well plate comprising two or more wells configured to accept the droplet;
wherein the power source configured to generate an electric field that deflects a droplet or otherwise directs a trajectory of a droplet ejected from the second end of the capillary into a well of a multi-well plate carried by the stage.

15. The device of claim 1, wherein the photodetector is positioned to absorb fluorescent light emitted from within the lumen of the capillary, and wherein the electrical signal is based on the fluorescent light.

16. The device of claim 1, wherein timing of applying the voltage is based on the electrical signal.

17. The device of claim 1, wherein the electrode comprises a transparent conductive film.

18. The device of claim 1, further comprising a pump configured to flow fluid through the capillary.

19. The device of claim 18, wherein the pump is operatively coupled to controller, the controller further including logic that when executed by the controller, causes the device to perform operations including:
flowing fluid through the capillary at a flow rate based on the electrical signal.

20. The device of claim 1, wherein the device is configured to eject a double emulsion comprising a core comprising a first liquid at least partially surrounded by a shell of a second liquid.

21. The device of claim 1, wherein the device is configured to eject an aqueous droplet from the second end of the capillary as a single emulsion.

22. A device for producing a droplet, the device comprising:
a capillary defining a lumen, the capillary comprising:
a first end coupleable to a fluid source; and
a second end opposite the first end, wherein a viewing portion of the lumen of the capillary is configured for visual inspection by a user;
an electrode in conductive communication with the second end of the capillary and a power source, wherein the electrode further comprises a capillary holder configured to carry the capillary and defining an illumination window shaped to expose an illumination portion of the capillary to light, and wherein the capillary holder comprises an outer tube; an inner tube coaxially carried by the outer tube; and a conductive spacer conductively coupling the inner tube and the outer tube;
a light source positioned to illuminate the viewing portion of the lumen of the capillary through the illumination window; and a controller operatively coupled to the power source, the controller including logic that when executed by the controller, causes the device to perform operations including:
applying, with the power source, a voltage to the electrode sufficient to eject a droplet from the second end of the capillary.

23. The device of claim 22, further comprising:
a stage configured to carry a multi-well plate comprising two or more wells configured to accept the droplet; and
a source of motion configured to move the stage relative to the second end of the capillary,
wherein the controller further includes logic that when executed by the controller, causes the device to perform operations including:
moving the stage with the source of motion relative to the second end of the capillary based upon an input from the user.

24. The device of claim 22, further comprising:
a stage configured to carry a multi-well plate comprising two or more wells configured to accept the droplet; and
a source of motion configured to move the stage relative to the second end of the capillary.

25. The device of claim 24, wherein the controller is operatively coupled to the source of motion and the photodetector, the controller further including logic that when executed by the controller, causes the device to perform operations including:
moving the stage with the source of motion relative to the second end of the capillary based upon the electrical signal.

26. The device of claim 24, wherein the controller is operatively coupled to the source of motion and the photodetector, the controller further including logic that when executed by the controller, causes the device to perform operations including:
moving the stage with the source of motion relative to the second end of the capillary such that the second end of the capillary is positioned to eject the droplet for receipt by one of the two or more wells when the electrical signal is at or above a threshold, wherein the threshold is a predetermined threshold.

27. The device of claim 24, wherein the controller further includes logic that when executed by the controller, causes the device to perform operations including:
moving the stage with the source of motion relative to the second end of the capillary based upon a user input.

28. The device of claim 22, wherein the device is configured to apply the voltage to the electrode based on an input from the user.

29. The device of claim 22, further comprising a microscope positioned to magnify the viewing portion of the lumen to generate a magnified image for receipt by the user.

30. The device of claim 22, wherein the electrode comprises a transparent conductive film.

31. The device of claim 22, further comprising an electrically conductive plate defining an aperture configured to receive a droplet ejected from the second end of the capillary.

32. The device of claim 31, wherein the electrically conductive plate is in conductive communication with the power source.

33. The device of claim 31, wherein the electrically conductive plate is in conductive communication with an electrical ground.

34. The device of claim 24, further comprising a multi-well plate cover being electrically conductive and defining two or more apertures configured to allow passage of droplets ejected from the second end of the capillary to the two or more wells of the multi well plate.

35. The device of claim 34, wherein the multi-well plate cover is conductively coupled to an electrical ground.

36. The device of claim 24, further comprising a second electrode coupled to the power source and disposed on the stage to contact a surface of the multi-well plate when the multi-well plate is carried by the stage.

37. The device of claim 36, wherein the controller is operatively coupled to the electrode and further includes logic that when executed by the controller, causes the device to perform operations including:
applying a voltage to the second electrode different than the voltage applied to electrode.

38. The device of claim 22, further comprising a pump configured to flow fluid through the capillary.

39. The device of claim 38, wherein the pump is operatively coupled to controller, the controller further including logic that when executed by the controller, causes the device to perform operations including:
flowing fluid through the capillary at a flow rate based on the electrical signal.

40. The device of claim 22, wherein the device is configured to eject a double emulsion comprising a core comprising a first liquid at least partially surrounded by a shell of a second liquid.

41. The device of claim 22, wherein the device is configured to eject an aqueous droplet from the second end of the capillary as a single emulsion.

42. The device of claim 22, further comprising:
a stage configured to carry a multi-well plate comprising two or more wells configured to accept the droplet; and
a power source configured to generate an electric field that deflects a droplet or otherwise directs a trajectory of a droplet ejected from the second end of the capillary into a well of a multi-well plate carried by the stage.

43. A system for generating droplets comprising:
a fluid source; and
a device comprising:
a capillary defining a lumen in fluidic communication with the fluid source, the capillary comprising:
a first end coupled to the fluid source; and
a second end opposite the first end;
an electrode in conductive communication with the second end of the capillary and a power source, wherein the electrode further comprises a capillary holder configured to carry the capillary and defining an illumination window shaped to expose an illumination portion of the capillary to light, and wherein the capillary holder comprises an outer tube; an inner tube coaxially carried by the outer tube; and a conductive spacer conductively coupling the inner tube and the outer tube;
a light source positioned to illuminate the illumination portion of the lumen of the capillary through the illumination window;
a photodetector configured to generate an electrical signal in response to light emitted by the light source; and
a controller operatively coupled to the power source, the photodetector, and the light source, the controller including logic that when executed by the controller, causes the device to perform operations including:
detecting the light from within the lumen based on the electrical signal from the photodetector; and
applying, with the power source, a voltage to the electrode sufficient to eject a droplet from the second end of the capillary, wherein timing of applying the voltage is based on timing of the electrical signal and whether the electrical signal is above a threshold.

44. The system of claim 43, wherein the fluid source comprises: a first fluidic channel comprising:
a proximal end in fluidic communication with a first liquid; and
a distal end in fluidic communication with the capillary; and a second fluidic channel in fluidic communication with the first fluidic channel and with a second liquid immiscible with the first liquid.

45. The system of claim 44, wherein the fluid source is configured to generate a discrete partition of the first liquid surrounded at least in part by the second liquid.

46. The system of claim 45, wherein the droplet ejected by the second end of the capillary is a double emulsion comprising a core comprising the first liquid at least partially surrounded by a shell of the second liquid.

47. The system of claim 46, wherein the core comprises a cell, a portion of a cell, or an amplified nucleic acid of a cell.

48. The system of claim 45, wherein the fluid source further comprises a third fluidic channel in fluid communication with the first fluidic channel and a third liquid comprising reagents reactive with a component of the first liquid.

49. The system of claim 48, wherein the reagents include reagents configured to perform a nucleic acid amplification reaction.

50. The system of claim 49, wherein the droplet ejected by the second end of the capillary comprises amplified nucleic acid of a cell or portion thereof.

51. The system of claim 43, wherein the fluid source comprises an aqueous liquid.

52. The system of claim 51, wherein the system is configured to eject an aqueous droplet from the second end of the capillary as a single emulsion.

53. The system of claim 52, wherein the aqueous liquid comprises one or more cells, and the system is configured to eject the droplet containing one of the one or more cells.

54. The system of claim 43, further comprising:
a stage configured to carry a multi-well plate comprising two or more wells configured to accept the droplet; and
a source of motion configured to move the stage relative to the second end of the capillary.

55. The system of claim 54, wherein the controller is operatively coupled to the source of motion and the second photodetector, the controller further including logic that when executed by the controller, causes the device to perform operations including:
moving the stage with the source of motion relative to the second end of the capillary such that the second end of the capillary is positioned to eject the droplet for receipt by one of the two or more wells when the electrical signal is at or above a threshold.

56. The system of claim 55, wherein the controller further includes logic that when executed by the controller, causes the device to perform operations including:
moving the stage with the source of motion relative to the second end of the capillary such that droplets ejected from the second end of the capillary are individually received by the two or more wells.

57. The system of claim 43, wherein the photodetector is positioned to absorb fluorescent light emitted from within the lumen of the capillary, and wherein the electrical signal is based upon the absorbed fluorescent light.

58. The system of claim 43, wherein the photodetector is positioned to absorb scattered light scattered off of a scattering source within the lumen of the capillary, and wherein the photodetector is configured to generate the electrical signal based upon the absorbed scattered light.

59. The system of claim 43, further comprising a second photodetector positioned to absorb fluorescent light emitted from within the lumen of the capillary and configured to generate a second electrical signal based upon the absorbed fluorescent light, wherein the second photodetector is selected from the group consisting of an avalanche photodiode, a silicon photomultiplier, a photomultiplier tube, a complementary-metal-oxide-semiconductor sensor, a charge-coupled device sensor, and combinations thereof.

60. The system of claim 43, further comprising an electrically conductive plate defining an aperture configured to receive a droplet ejected from the second end of the capillary.

61. The system of claim 60, wherein the electrically conductive plate is in conductive communication with the power source.

62. The system of claim 60, wherein the electrically conductive plate is in conductive communication with an electrical ground.

63. A system for generating droplets comprising:
a fluid source; and
a device comprising:
a capillary defining a lumen, the capillary comprising:
a first end coupled to the fluid source; and
a second end opposite the first end, wherein a viewing portion of the lumen of the capillary is configured for visual inspection by a user;
an electrode in conductive communication with the second end of the capillary and a power source, wherein the electrode further comprises a capillary holder configured to carry the capillary and defining an illumination window shaped to expose an illumination portion of the capillary to light, and wherein the capillary holder comprises an outer tube; an inner tube coaxially carried by the outer tube; and a conductive spacer conductively coupling the inner tube and the outer tube;
a light source positioned to illuminate the viewing portion of the lumen of the capillary through the illumination window; and
a controller operatively coupled to the power source, the controller including logic that when executed by the controller, causes the device to perform operations including:
applying, with the power source, a voltage to the electrode sufficient to eject a droplet from the second end of the capillary, wherein the device is configured to apply the voltage to the electrode based on an input from the user.

64. The system of claim 63, further comprising a microscope configured to magnify the viewing portion of the lumen to generate a magnified image for receipt by the user.

65. The system of claim 63, wherein the fluid source comprises an aqueous liquid.

66. The system of claim 63, further comprising:
a stage configured to carry a multi-well plate comprising two or more wells configured to accept the droplet; and
a source of motion configured to move the stage relative to the second end of the capillary.

67. The system of claim 63, further comprising an electrically conductive plate defining an aperture configured to receive a droplet ejected from the second end of the capillary.

68. The system of claim 63, wherein the fluid source comprises: a first fluidic channel comprising:
a proximal end in fluidic communication with a first liquid; and
a distal end in fluidic communication with the capillary; and a second fluidic channel in fluidic communication with the first fluidic channel and with a second liquid immiscible with the first liquid.

69. A method of producing a droplet:
flowing a fluid through a capillary;
emitting light from a light source into a lumen of the capillary; and
applying, with a power source, a voltage to an electrode conductively coupled to a distal end of the capillary to eject a droplet from the distal end, wherein the electrode further comprises a capillary holder configured to carry the capillary and defining an illumination window shaped to expose an illumination portion of the capillary to light, and wherein the capillary holder comprises an outer tube; an inner tube coaxially carried by the outer tube; and a conductive spacer conductively coupling the inner tube and the outer tube,
wherein timing of applying the voltage is based on timing of the electrical signal and whether the electrical signal is above a threshold.

70. The method of claim 69, further comprising moving, with a source of motion, a stage carrying a multi-well plate comprising two or more wells relative to the distal end of the capillary such that the droplet is received by one of the two or more wells.

71. The method of claim 70, further comprising generating, with a photodetector, an electrical signal in response to light from within the lumen.

72. The method of claim 71, wherein the method further comprises moving the stage is based on the electrical signal.

73. The method of claim 72, wherein the electrical signal is based on scattered light scattered off of a scattering source disposed in the lumen of the capillary.

74. The method of claim 72, wherein the electrical signal is based on fluorescent light emitted from a fluorophore within the lumen of the capillary.

75. The method of claim 72, wherein timing of applying the voltage is based on the electrical signal.

76. The method of claim 69, wherein a viewing portion of the capillary is configured to be viewed by a user.

77. The method of claim 76, wherein timing of applying the voltage to the electrode is based on an input from the user.

78. The method of claim 76, wherein moving the stage is based upon a user input.

79. The method of claim 69, wherein flowing the fluid through the capillary comprises flowing a plurality of discrete partitions comprising a first liquid at least partially surrounded by a second liquid immiscible with the first liquid through the capillary.

80. The method of claim 79, wherein the droplet comprises double emulsion comprising the first liquid and the second liquid.

81. The method of claim 79, wherein a discrete partition of the plurality of the discrete partitions further comprises a cell or portion thereof disposed in the first liquid.

82. The method of claim 79, wherein the discrete partition further comprises a reagent reactive with the cell or portion thereof disposed in the first liquid.

83. The method of claim 82, wherein the reagent includes a reagent for a nucleic acid amplification reaction.

84. The method of claim 79, wherein the first fluid comprises one or more cells.

85. The method of claim 84, wherein the droplet comprises a cell of the one or more cells, a portion thereof, or an amplified nucleic acid of the cell.

86. The method of claim 85, wherein the portion of the one or more cells is selected from the group consisting of an organelle, a vesicle, a virus, a bacterium, an organoid, and a spheroid.

* * * * *

UNITED STATES PATENT AND TRADEMARK OFFICE
CERTIFICATE OF CORRECTION

Page 1 of 1

PATENT NO. : 12,280,376 B2
APPLICATION NO. : 17/424397
DATED : April 22, 2025
INVENTOR(S) : Daniel Chiu et al.

It is certified that error appears in the above-identified patent and that said Letters Patent is hereby corrected as shown below:

In the Claims

| Column | Line(s) | |
| --- | --- | --- |
| 33 | 3 | Claim 34, delete "multi well plate." and insert -- multi-well plate. -- |

Signed and Sealed this
Third Day of February, 2026

John A. Squires
*Director of the United States Patent and Trademark Office*